US008030346B2

(12) United States Patent
Allen et al.

(10) Patent No.: US 8,030,346 B2
(45) Date of Patent: Oct. 4, 2011

(54) HETEROCYCLIC QUINOLONE DERIVATIVES THAT INHIBIT PROLYL HYDROXYLASE ACTIVITY

(75) Inventors: Jennifer R. Allen, Newbury Park, CA (US); Roland Burli, Bishop's Shortford (GB); Michael J. Frohn, Thousand Oaks, CA (US); Randall W. Hungate, Camarillo, CA (US); Susana C. Neira, Thousand Oaks, CA (US); Anthony B. Reed, Oxnard, CA (US)

(73) Assignee: Amgen Inc., Thousand Oaks, CA (US)

( * ) Notice: Subject to any disclaimer, the term of this patent is extended or adjusted under 35 U.S.C. 154(b) by 827 days.

(21) Appl. No.: 12/150,675

(22) Filed: Apr. 29, 2008

(65) Prior Publication Data

US 2009/0156633 A1    Jun. 18, 2009

Related U.S. Application Data

(60) Provisional application No. 60/927,772, filed on May 4, 2007.

(51) Int. Cl.
| | |
|---|---|
| A61K 31/385 | (2006.01) |
| A01N 43/42 | (2006.01) |
| A01N 43/78 | (2006.01) |
| C07D 221/22 | (2006.01) |
| C07D 515/02 | (2006.01) |

(52) U.S. Cl. ........ 514/439; 514/291; 514/301; 514/366; 514/367; 514/440; 546/26; 546/114

(58) Field of Classification Search .................... 546/26, 546/114; 514/291, 301, 366, 367, 439, 440
See application file for complete search history.

(56) References Cited

U.S. PATENT DOCUMENTS

| | | | |
|---|---|---|---|
| 3,954,733 | A | 5/1976 | Tobiki et al. |
| 3,992,371 | A | 11/1976 | Tobiki et al. |
| 4,215,123 | A | 7/1980 | Scotese et al. |
| 4,374,138 | A | 2/1983 | Haskell et al. |
| 4,382,089 | A | 5/1983 | Haskell et al. |
| 4,404,201 | A | 9/1983 | Haskell et al. |
| 4,468,394 | A | 8/1984 | Machida et al. |
| 4,710,473 | A | 12/1987 | Morris |
| 5,037,826 | A | 8/1991 | Blythin et al. |
| 5,126,341 | A | 6/1992 | Suzuki et al. |
| 5,378,679 | A | 1/1995 | Nuebling et al. |
| 5,502,035 | A | 3/1996 | Haviv et al. |
| 5,620,995 | A | 4/1997 | Weidmann et al. |
| 5,719,164 | A | 2/1998 | Weidmann et al. |
| 5,798,451 | A | 8/1998 | von Deyn et al. |
| 5,972,841 | A | 10/1999 | von Deyn et al. |
| 6,093,730 | A | 7/2000 | Weidmann et al. |
| 6,593,343 | B2 | 7/2003 | Björk et al. |
| 6,787,326 | B1 | 9/2004 | Ratcliffe et al. |
| 2003/0153503 | A1 | 8/2003 | Klaus et al. |
| 2004/0235082 | A1 | 11/2004 | Fourney et al. |
| 2004/0254215 | A1 | 12/2004 | Arend et al. |
| 2005/0020487 | A1 | 1/2005 | Klaus et al. |
| 2005/0107364 | A1 | 5/2005 | Hutchinson et al. |
| 2006/0216295 | A1 | 9/2006 | Crabtree et al. |
| 2006/0251638 | A1 | 11/2006 | Guenzler-Pukall et al. |
| 2006/0276477 | A1 | 12/2006 | Klaus et al. |
| 2007/0004627 | A1 | 1/2007 | Seeley et al. |
| 2007/0203174 | A1 | 8/2007 | Klimko et al. |
| 2007/0249605 | A1 | 10/2007 | Allen et al. |
| 2008/0171756 | A1 | 7/2008 | Shaw et al. |
| 2009/0082357 | A1 | 3/2009 | Fitch et al. |

FOREIGN PATENT DOCUMENTS

| | | |
|---|---|---|
| AT | 328085 | 3/1976 |
| EP | 0 500 297 A1 | 8/1992 |
| EP | 0 503 844 A1 | 9/1992 |
| EP | 0 937 459 A2 | 8/1999 |
| EP | 0 547 708 B1 | 2/2003 |
| EP | 1 541 558 A1 | 8/2003 |
| EP | 1 538 160 A1 | 6/2005 |
| GB | 1 449 256 | 9/1976 |
| JP | 49 35392 | 4/1974 |
| JP | 7224040 A2 | 8/1995 |
| SU | 1735288 | 5/1992 |
| WO | WO 01/85732 A1 | 11/2001 |
| WO | WO 02/24679 A1 | 3/2002 |
| WO | WO 02/076396 A2 | 10/2002 |
| WO | WO 03/053997 A2 | 7/2003 |
| WO | WO 2004/037853 A2 | 5/2004 |
| WO | WO 2004/103974 A1 | 12/2004 |
| WO | WO 2004/104000 A1 | 12/2004 |
| WO | WO 2004/108121 A1 | 12/2004 |
| WO | WO 2004/108681 A1 | 12/2004 |
| WO | WO 2005/011696 A1 | 2/2005 |
| WO | WO 2005/021546 A1 | 3/2005 |
| WO | WO 2005/047285 A1 | 5/2005 |
| WO | WO 2005/077050 A2 | 8/2005 |
| WO | WO 2005/111044 A1 | 11/2005 |
| WO | WO 2006/088246 A1 | 8/2006 |
| WO | WO 2006/094292 A2 | 9/2006 |
| WO | WO 2007/038571 A2 | 4/2007 |
| WO | WO 2007/070359 A2 | 6/2007 |
| WO | WO 2007/097929 A1 | 8/2007 |
| WO | WO 2007/103905 A2 | 9/2007 |
| WO | WO 2007/136990 A2 | 11/2007 |
| WO | WO 2007/150011 A2 | 12/2007 |
| WO | WO 2008/040002 A2 | 4/2008 |

OTHER PUBLICATIONS

U.S. Appl. No. 12/002,537, filed Dec. 17, 2007, Allen et al.

(Continued)

Primary Examiner — Sreeni Padmanabhan
Assistant Examiner — Svetlana M Ivanova
(74) Attorney, Agent, or Firm — Bernard P. Friedrichsen

(57) ABSTRACT

Compounds of Formula I are useful inhibitors of HIF prolyl hydroxylases. Compounds of Formula I have the following structure:

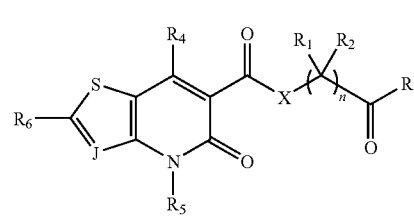

where the definitions of the variables are provided herein.

74 Claims, 3 Drawing Sheets

OTHER PUBLICATIONS

U.S. Appl. No. 12/002,538, filed Dec. 17, 2007, Allen et al.
U.S. Appl. No. 12/082,263, filed Apr. 9, 2008, Allen et al.
U.S. Appl. No. 12/148,179, filed Apr. 16, 2008, Allen et al.
U.S. Appl. No. 12/150,998, filed May 2, 2008, Allen et al.
International Search Report from co-pending PCT Application No. PCT/US2008/005664 (WO 2008/137060 A1 cover page and ISR) published on Nov. 13, 2008.
He, L. et al., "Probabilistic Neural Network Multiple Classifier System for Predicting the Genotoxicity of Quinolones and Quinoline Derivatives," Chem. Res. Toxicol. 18, pp. 428-440 (2005).
Ukrainets, I.V. et al., "4-Hydroxy-2-Quinolines. XXI. 1H-2-Oxo-4-Hydroxyquinoline-3-Carboxylic Alkylamides as a Novel Group of Antithyroid Drugs," Farmatsevtichnii Zhurnal (Kiev) 6, pp. 54-55 (1995).
Bezuglyi, P.A., "Amides of 4-Hydroxyquinoline-2-oxo-3-carboxylic Acid: Synthesis and Anticoagulant Activity," Khimiko-Farmatsevticheskii Zhurnal, 24(4) pp. 31-32 (1990). This document is in the Russian language-an English language abstract is included.
Schofield, C.J. et al., "Oxygen Sensing by HIF Hydroxylases", Nature Reviews, Molecular Cell Biology, 5(5), pp. 243-254 (2004).
McDowell, R. S. et al., "From Peptide to Non-Peptide. 2. The De Novo Design of Potent, Non-peptidal Inhibitors of Platelet Aggregation Based on a Benzodiazepinedione Scaffold," J. Am. Chem. Soc. 116(12) pp. 5077-5083 (1994).
Bohnert et al., "Redox Reactions with Cyclopeptide-Like Quinoline Derivatives as Lipophilic, Masked NAD Model Compounds," Zeitschrift für Naturforschung, B.: Chemical Sciences, 42(9) pp. 1159-1166 (1987). This document is in the German language-an English language abstract is included.
Kath, J.C. et al., Potent Small Molecule CCR1 Antagonists, Bioorg & Med. Chem. Letters, 14(9), pp. 2169-2173 (2004).
Ukrainets, I.V. et al., "4-Hydroxy-2-Quinolones. 4. Selection of the Optimum Path for Synthesis of N-R-Substituted 4-Hydroxy-2-Quinolone-3-Carboxylic Acid Amides." Chemistry of Heterocyclic Compounds 28(5), pp. 538-540 (1992).
Warshakoon, N.C. et al., "Design and Synthesis of a Series of Novel Pyrazolopyridines as HIF 1-α Prolyl Hydroxylase Inhibitors," Bioorg & Med. Chem. Letters, 16, pp. 5687-5690 (2006).
Warshakoon, N.C. et al., "Structure-Based Design, Synthesis, and SAR Evaluation of a New Series of 8-Hydroxyquinolinse as HIF-1α Prolyl Hydroxylase Inhibitors," Bioorg & Med. Chem. Letters, 16, pp. 5517-5522 (2006).
Warshakoon, N.C. et al., "A Novel Series of Imidazo[1,2-a]pyridine Derivatives as HIF-1α Prolyl Hydroxylase Inhibitors," Bioorg & Med. Chem. Letters, 16, pp. 5598-5601 (2006).
McDonough, M.A. et al., "Cellular Oxygen Sensing: Crystal Structure of Hypoxia-Inducible Factor Prolyl Hydroxylase (PHD2)," Proc. Natl. Acad. Sci., 103(26) pp. 9814-9819 (2006).
Jönssen, S. et al., "Synthesis and Biological Evaluation of New 1,2-Dihydro-4-hydroxy-2-oxo-3-quinolinecarboxamides for Treatment of Autoimmune Diorders: Structure-Activity Relationship," J. Med. Chem. 47, pp. 2075-2088 (2004).
Buckle, D.R. et al., "Synthesis and Antiallergic Activity of 2-Hydroxy-3-nitro-1,4-naphthoquinones," J. Med. Chem. 20(8), pp. 1059-1064 (1977).
Franklin, T.J. et al., "Approaches to the Design of Anti-Fibrotic Drugs," Biochem. Soc. Trans. 19, pp. 812-815 (1991).
Vippagunta, S.R. et al. "Crystalline Solids," Advanced Drug Delivery Reviews, 48, pp. 3-26 (2001).
Lala, P. K. et al. "Role of nitric oxide in tumor progression: Lessons from experimental tumors," Cancer and Metastasis Reviews, 17, pp. 91-106, (1998).
Golub, T. R. et al. "Molecular Classification of Cancer: Class Discovery and Class Prediction by Gene Expression Monitoring", Science, 286, pp. 531-537 (1999).
Prosecution History of U.S. Appl. No. 12/002,538 Without Cited References, From Dec. 17, 2007 to Jun. 17, 2011.
Prosecution History of U.S. Appl. No. 11/635,683 Without Cited References, From Dec. 8, 2006 to Aug. 2, 2010.
Prosecution History of U.S. Appl. No. 12/703,496 Without Cited References, From Feb. 10, 2010 to May 16, 2011.
Prosecution History of U.S. Appl. No. 12/703,716 Without Cited References, From Feb. 10, 2010 to May 17, 2011.
Prosecution History of U.S. Appl. No. 12/002,537 Without Cited References, From Dec. 17, 2007 to Dec. 22, 2009.
Prosecution History of U.S. Appl. No. 12/612,465 Without Cited References, From Nov. 4, 2009 to Apr. 19, 2011.
Prosecution History of U.S. Appl. No. 12/082,263 Without Cited References, From Apr. 9, 2008 to Aug. 4, 2009.
Prosecution History of U.S. Appl. No. 12/148,179 Without Cited References, From Apr. 16, 2008 to May 24, 2011.
Prosecution History of U.S. Appl. No. 13/109,877 Without Cited References, From May 17, 2011 to Jun. 9, 2011.
Prosecution History of U.S. Appl. No. 12/150,998 Without Cited References, From May 2, 2008 to May 5, 2011.

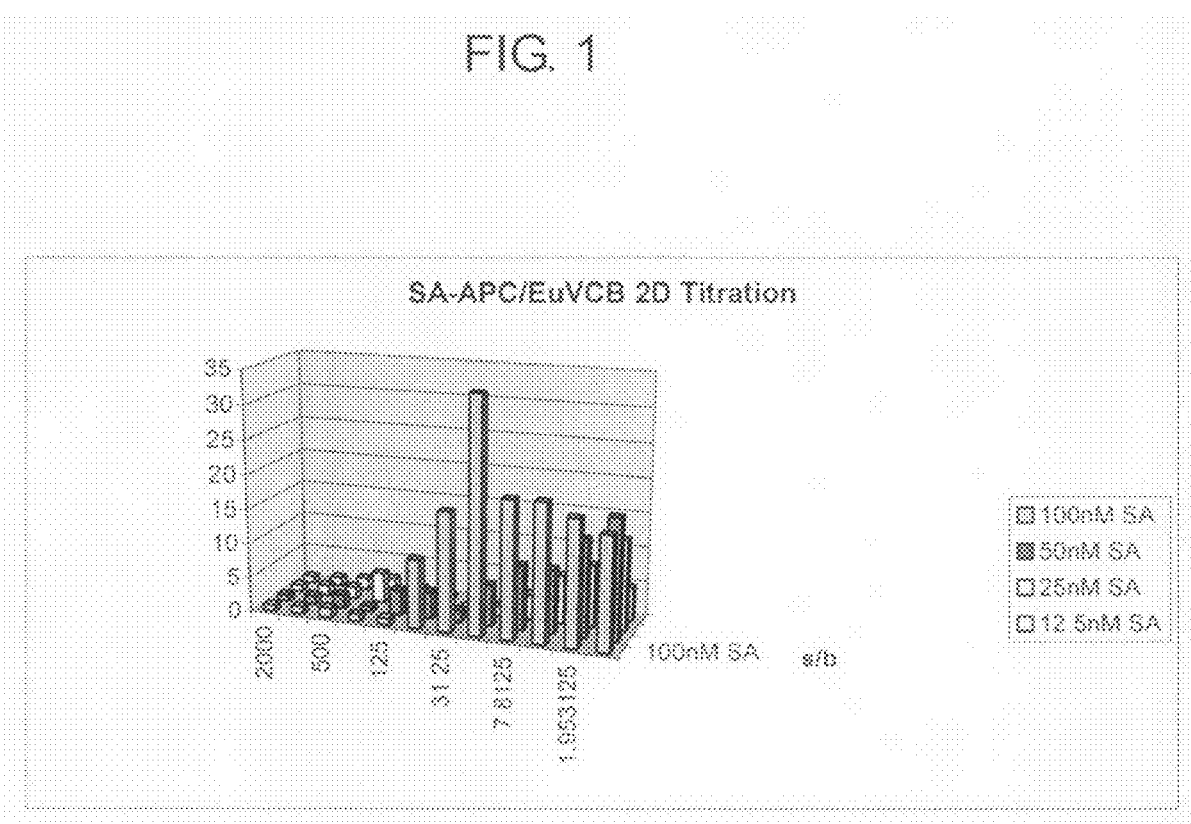

HETEROCYCLIC QUINOLONE DERIVATIVES THAT INHIBIT PROLYL HYDROXYLASE ACTIVITY

CROSS REFERENCES TO RELATED APPLICATIONS

This application claims the benefit of U.S. Provisional Application No. 60/927,772, filed on May 4, 2007, which is hereby incorporated by reference in its entirety and for all purposes as if fully set forth herein.

FIELD OF THE INVENTION

The present invention relates to compounds capable of inhibiting prolyl hydroxylases such as HIF prolyl hydroxylases, compounds that modulate HIF levels, compounds that stabilize HIF, compositions comprising the compounds, and methods for their use for controlling HIF levels. The compounds and compositions may be used to treat diseases or conditions modulated by HIF such as ischemia, anemia, wound healing, auto-transplantation, allo-transplantation, xeno-transplantation, systemic high blood pressure, thalassemia, diabetes, cancer, and inflammatory disorders.

BACKGROUND OF THE INVENTION

The cellular transcription factor HIF (Hypoxia Inducible Factor) occupies a central position in oxygen homeostasis in a wide range of organisms and is a key regulator of responses to hypoxia. The genes regulated by HIF transcriptional activity can play critical roles in angiogenesis, erythropoiesis, hemoglobin F production, energy metabolism, inflammation, vasomotor function, apoptosis and cellular proliferation. HIF can also play a role in cancer, in which it is commonly upregulated, and in the pathophysiological responses to ischemia and hypoxia.

The HIF transcriptional complex comprises an a heterodimer: HIF-β is a constitutive nuclear protein that dimerizes with oxygen-regulated HIF-α subunits. Oxygen regulation occurs through hydroxylation of the HIF-α subunits, which are then rapidly destroyed by the proteasome. In oxygenated cells, the von Hippel-Lindau tumor suppressor protein (pVHL) binds to hydroxylated HIF-α subunits, thereby promoting their ubiquitin dependent proteolysis. This process is suppressed under hypoxic conditions, stabilizing HIF-α and promoting transcriptional activation by the HIF αβ complex. See, e.g., U.S. Pat. No. 6,787,326.

Hydroxylation of HIF-α subunits can occur on proline and asparagine residues and can be mediated by a family of 2-oxoglutarate dependent enzymes. This family includes the HIF prolyl hydroxylase isozymes (PHDs), which hydroxylate Pro 402 and Pro 564 of human HIF1α, as well as Factor Inhibiting HIF (FIH), which hydroxylates Asn 803 of human HIF1α. Inhibition of FIH or the PHDs leads to HIF stabilization and transcriptional activation. See, e.g., Schofield and Ratcliffe, Nature Rev. Mol. Cell. Biol., Vol 5, pages 343-354 (2004).

SUMMARY OF THE INVENTION

In one aspect, the invention provides a composition of matter that includes at least one compound of Formula I:

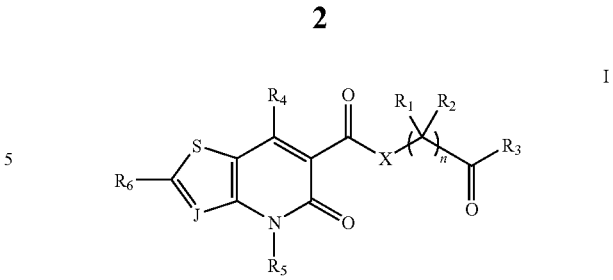

a pharmaceutically acceptable salt thereof, a tautomer thereof, or a pharmaceutically acceptable salt of the tautomer; or a solvate thereof, a chelate thereof, a non-covalent complex thereof, a prodrug thereof, or a mixture of any of the foregoing, wherein:

J is selected from $CR_7$ or N;

n is 1 to 6;

$R_1$ and $R_2$ are independently selected in each instance from H, lower alkyl, substituted lower alkyl, lower haloalkyl, or substituted lower haloalkyl, or $R_1$ and $R_2$ can join together to form a 3 to 6 membered ring or a substituted 3 to 6 membered ring;

X is selected from —$NR_a$—, —O—, —S—, or —($CR_b R_c$)—, wherein $R_a$ is selected from H or lower alkyl, and $R_b$ and $R_c$ are independently selected from H, lower alkyl, substituted lower alkyl, lower haloalkyl, or substituted lower haloalkyl, or $R_b$ and $R_c$ can join together to form a 3 to 6 membered ring or a substituted 3 to 6 membered ring;

$R_3$ is selected from OH, SH, $NH_2$, lower alkyl, substituted lower alkyl, lower alkoxy, substituted lower alkoxy, or sulfanyl;

$R_4$ is selected from H, OH, lower alkoxy, SH, $NH_2$, $NHSO_2R_8$, or sulfonyl;

$R_5$ is selected from H, lower alkyl, or substituted lower alkyl;

$R_6$ and $R_7$ are independently selected from H, F, Cl, Br, I, alkyl, substituted alkyl, haloalkyl, perhaloalkyl, alkenyl, substituted alkenyl, alkynyl, substituted alkynyl, $NR_d R_e$, C(O)$R_8$, C(O)O$R_9$, O$R_9$, S$R_9$, $SO_2R_9$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, or —Y—$R_{10}$; or, $R_6$ and $R_7$ may join to form an optionally substituted 5 or 6 membered ring when J is $CR_7$, wherein:

Y is selected from —N($R_{11}$)—Z— or —Z—N($R_{11}$)—;

Z is selected from C(O), $SO_2$, alkylene, substituted alkylene, alkenylene, substituted alkenylene, alkynylene, or substituted alkynylene;

$R_8$ is selected from H, alkyl, substituted alkyl, alkenyl, substituted alkenyl, alkynyl, substituted alkynyl heterocyclyl, substituted heterocyclyl, aryl, substituted aryl, heteroaryl, or substituted heteroaryl;

$R_9$ is selected from H, alkyl, substituted alkyl, alkenyl, substituted alkenyl, alkynyl, or substituted alkynyl;

$R_{10}$ is selected from H, heterocyclyl, substituted heterocyclyl, aryl, substituted aryl, heteroaryl, or substituted heteroaryl;

$R_{11}$ is selected from H, lower alkyl, or substituted lower alkyl; and $R_d$ and $R_e$ are independently selected from H, lower alkyl, substituted lower alkyl, lower haloalkyl, or substituted lower haloalkyl, or $R_d$ and $R_d$ can join together to form a 3 to 6 membered ring or a substituted 3 to 6 membered ring.

In some embodiments, X is —($CR_b R_c$)—, and $R_b$ and $R_c$ are independently selected from H, lower alkyl, substituted lower alkyl, lower haloalkyl, or substituted lower haloalkyl, or $R_b$ and $R_c$ can join together to form a 3 to 6 membered ring or a substituted 3 to 6 membered ring. In some such embodiments, $R_b$ and $R_c$ are independently selected from H, lower alkyl, substituted lower alkyl, lower haloalkyl, or substituted lower haloalkyl. In still other such embodiments, $R_b$ and $R_c$ are independently selected from H and lower alkyl. In still further such embodiments, $R_b$ and $R_c$ are both H. In some such embodiments, n is 1. In some such embodiments, $R_1$ and $R_2$ are independently selected in each instance from H, lower alkyl, substituted lower alkyl, lower haloalkyl, or substituted lower haloalkyl. In still other such embodiments, $R_1$ and $R_2$ are independently selected in each instance from H, lower alkyl, or substituted lower alkyl. In still other such embodiments, $R_1$ and $R_2$ are both H. In some embodiments, J is $CR_7$, n is 1; $R_1$ is H or lower alkyl; $R_2$ is H; $R_3$ is OH; $R_4$ is OH; and $R_b$ and $R_c$ are both H. In other embodiments, J is N, n is 1; $R_1$ is H or lower alkyl; $R_2$ is H; $R_3$ is OH; $R_4$ is OH; and $R_b$ and $R_c$ are both H.

In some embodiments where X is —$(CR_bR_c)$—, the CPH1 $IC_{50}$ value divided by the PHD2 $IC_{50}$ value is greater than 5, greater than 10, greater than 15, greater than 20, greater than 25, or greater than 30. In some such embodiments, the CPH1 $IC_{50}$ value divided by the PHD2 $IC_{50}$ value is greater than 10.

In some embodiments, $R_1$ and $R_2$ are not both H if X is —$NR_a$—; $R_a$ is H; and n is 1.

In some embodiments, n is 1, and $R_1$ and $R_2$ are both H.

In some embodiments, at least one of $R_1$ and $R_2$ is not H. In some such embodiments, at least one of $R_1$ and $R_2$ is a lower alkyl such as a $(C_1-C_4)$alkyl. In some such embodiments, one of $R_1$ and $R_2$ is H and the other of $R_1$ and $R_2$ is a lower alkyl. In some such embodiments, at least one of $R_1$ and $R_2$ is a methyl group, and in some such embodiments, the other of $R_1$ and $R_2$ is a methyl group.

In some embodiments, J is $CR_7$. In other embodiments, J is N.

In some embodiments, $R_3$ is OH.

In some embodiments, $R_4$ is OH.

In some embodiments, X is —$NR_a$—. In some such embodiments, X is —NH—.

In other embodiments, X is —$(CR_bR_cC)$—. In some embodiments, $R_b$ and $R_c$ are independently chosen from H and lower alkyl. In some such embodiments, $R_b$ and $R_c$ are independently selected from H and methyl. In some such embodiments, $R_b$ and $R_c$ are both H.

In some embodiments, at least one of $R_6$ or $R_7$ is a substituted or unsubstituted aryl, a substituted or unsubstituted heteroaryl, a substituted or unsubstituted cycloalkyl, or a substituted or unsubstituted heterocyclyl group. In some such embodiments, at least one of $R_6$ or $R_7$ is a heterocyclyl group. In other such embodiments, at least one of $R_6$ or $R_7$ is a heteroaryl group. In other such embodiments, at least one of $R_6$ or $R_7$ is a phenyl or substituted phenyl group.

In some embodiments, at least one of $R_6$ or $R_7$ is independently selected from halo or a moiety substituted with at least one halo. For example, in some embodiments, at least one of $R_6$ or $R_7$ is haloalkyl. In some embodiments, at least one of $R_6$ or $R_7$ is a perhaloalkyl. In some embodiments, the perhaloalkyl is a perfluoroalkyl group such as $CF_3$.

In some embodiments, n is 1.

In some embodiments, $R_1$ and $R_2$ are independently chosen from H and lower alkyl. In some such embodiments, $R_1$ and $R_2$ are both H. In some such embodiments, n is 1. In still other such embodiments, X is —$(CR_bR_c)$— and $R_b$ and $R_c$ are selected from H and lower alkyl, and in some such embodiments, $R_b$ and $R_c$ are both H. Therefore, in some embodiments $R_1$, $R_2$, $R_b$, and $R_c$ are all H and n is 1.

In some embodiments, J is $CR_7$, n is 1; $R_1$ is H or lower alkyl; $R_2$ is H; $R_3$ is OH; $R_4$ is OH; X is —$NR_a$— wherein $R_a$ is H, or X is —$(CR_bR_c)$— wherein $R_b$ and $R_c$ are both H.

In some embodiments, J is N, n is 1; $R_1$ is H or lower alkyl; $R_2$ is H; $R_3$ is OH; $R_4$ is OH; X is —$NR_a$— wherein $R_a$ is H, or X is —$(CR_bR_c)$— wherein $R_b$ and $R_c$ are both H.

In some embodiments, $R_5$ is H. In other embodiments, $R_5$ is a lower alkyl group. In some such embodiments, $R_5$ is a methyl. In still other embodiments, $R_5$ is a substituted lower alkyl selected from an arylalkyl, a heteroarylalkyl, a heterocyclylalkyl, a cycloalkylalkyl, a hydroxyalkyl, an alkoxyalkyl, or a haloalkyl.

In some embodiments, J is $CR_7$ and $R_6$ and $R_7$, together with the carbon atoms to which they are attached, join to form a 6-membered carbocyclic aromatic ring that may be optionally substituted with up to three substituents.

In some embodiments, the composition of matter is a salt. Such salts may be anhydrous or associated with water as a hydrate.

In some embodiments, the composition of matter is a prodrug. In some such embodiments, the composition of matter is a $(C_1-C_6)$alkyl ester such as a methyl, ethyl, propyl, butyl, pentyl, or hexyl ester.

Also provided herein are pharmaceutical formulations that include at least one pharmaceutically acceptable carrier, excipient or diluent and a therapeutically effective amount of the composition of matter of any of the embodiments described herein. In such embodiments, the composition of matter is present in an amount effective for the treatment of at least one disease selected from ischemia, anemia, wound healing, auto-transplantation, allo-transplantation, xeno-transplantation, systemic high blood pressure, thalassemia, diabetes, cancer, or an inflammatory disorder.

Further provided are pharmaceutical formulations that include at least one pharmaceutically acceptable carrier, and a therapeutically effective amount of the composition of matter of any of the embodiments described herein in combination with at least one additional compound such as an erythropoiesis stimulating agent or a chemotherapeutic agent.

Additionally provided is a method of increasing or stabilizing HIF levels or activity in a subject by administering to the subject the composition of matter of any of the embodiments described herein.

Further provided is a method of treating a condition where it is desired to modulate HIF activity comprising administering to a subject the composition of matter of any of the embodiments described herein. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

Also provided is a method of treating a hypoxic or ischemic related disorder in a subject comprising administering to a subject the composition of matter of any of the embodiments described herein.

Also provided is a method of treating anemia in a subject comprising administering to a subject the composition of matter of any of the embodiments described herein.

Further provided is a method of modulating the amount of HIF in a cell comprising contacting the cell with the composition of matter of any of the embodiments described herein.

Additionally provided is a method of increasing the amount of hemoglobin F in a subject comprising administering to the subject the composition of matter of any of the embodiments described herein.

Also provided is a method of modulating angiogenesis in a subject comprising administering to the subject the composition of matter of any of the embodiments described herein.

Additionally provided is a method of treating at least one disease in a patient in need of such treatment comprising administering to the patient a therapeutically effective amount of the composition of matter of any of the embodiments described herein. In some such embodiments, the at least one disease is selected from ischemia, anemia, wound healing, auto-transplantation, allo-transplantation, xeno-transplantation, systemic high blood pressure, thalassemia, diabetes, cancer, or an inflammatory disorder.

Also provided is a method of inhibiting HIF hydroxylation in a subject comprising administering to the subject the composition of matter n of any of the embodiments described herein.

In some embodiments, the HIF PHD inhibitory activity $IC_{50}$ value of the composition of matter is 40 µM or less. In other embodiments, the HIF PHD inhibitory activity $IC_{50}$ value of the composition of matter is 10 µM or less.

In some embodiments, the composition of matter of any of the embodiments is used in the preparation of a medicament.

In some such embodiments, the composition of matter of any of the embodiments is used in the preparation of a medicament for increasing or stabilizing HIF levels or activity in a subject.

In some such embodiments, the composition of matter of any of the embodiments is used in the preparation of a medicament for treating a condition where it is desired to modulate HIF activity. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

In some embodiments, the composition of matter of any of the embodiments is used in the preparation of a medicament for treating a hypoxic or ischemic related disorder in a subject.

In some embodiments, the composition of matter of any of the embodiments is used in the preparation of a medicament for modulating the amount if HIF in a cell. In some embodiments, the composition of matter according to any of the embodiments is used to modulate the amount of HIF in a cell.

In some embodiments, the composition of matter of any of the embodiments is used in the preparation of a medicament for modulating angiogenesis in a subject.

In some embodiments, the composition of matter of any of the embodiments is used in the preparation of a medicament for inhibiting HIF hydroxylation in a subject.

In some embodiments, the composition of matter of any of the embodiments is used in the preparation of a medicament for treating anemia.

In some embodiments, the composition of matter of any of the embodiments is used in a method for increasing the level of erythropoietin in the blood of a subject.

Other objects, features and advantages of the invention will become apparent to those skilled in the art from the following description and claims.

BRIEF DESCRIPTION OF THE DRAWINGS

FIG. 1 is a graph illustrating the ratio of fluorescence signal to background generated by the interaction of Eu-VCB with streptavidin-APC-hydroxyprolyl HIF1α peptide.

FIG. 2A illustrates a 0-125 nM peptide range and FIG. 2B illustrates a 0-10 nM peptide range.

FIG. 3A illustrates a time course for the hydroxylation of the HIF1α peptide with increasing amounts of HIF PHD2 enzyme. FIG. 3B illustrates initial rates with increasing enzyme concentrations.

DETAILED DESCRIPTION OF THE INVENTION

Figure 2A:
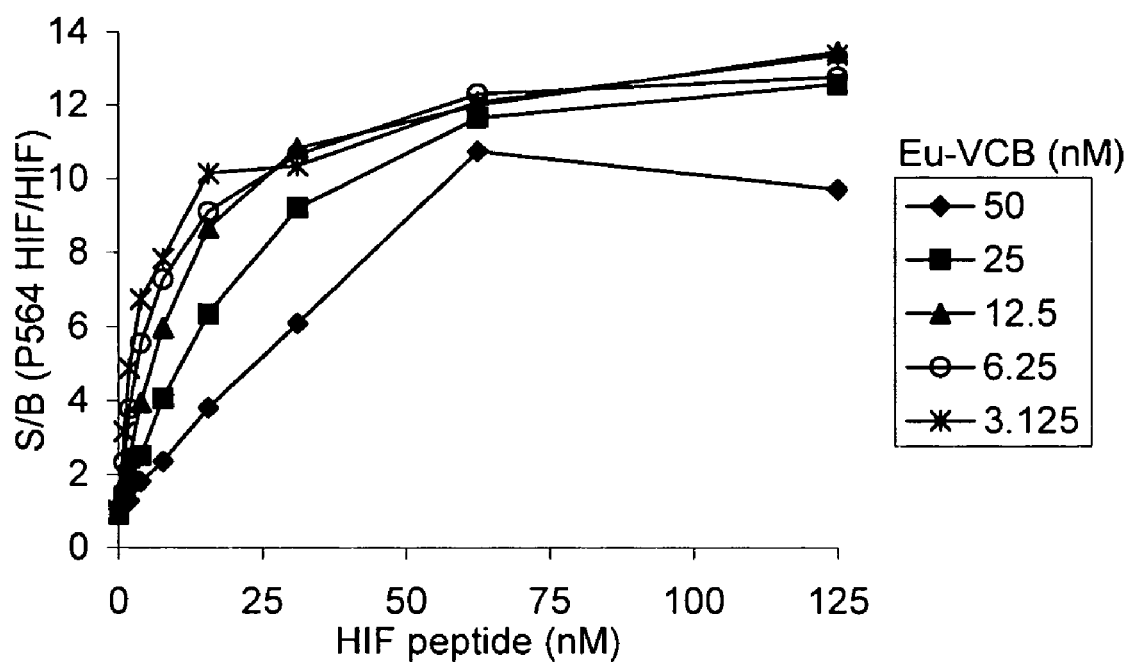
FIGS. 2A and 2B are graphs illustrating the ratio of TR-FRET signal generated by the interaction of Eu-VCB with streptavidin-APC-hydroxyprolyl HIF1α peptide over background signal generated by the interaction of Eu-VCB with streptavidin-APC-HIF1α peptide (nonhydroxylated).

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

Compounds of Formula I include, but are not limited to, optical isomers of compounds of Formula I, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula I include Z- and E-forms (or cis- and trans-forms) of compounds with double bonds.

Compounds of the invention may exist in multiple tautomeric forms. These forms are illustrated below as "Tautomer A", "Tautomer B", and "Tautomer C":

Tautomer A

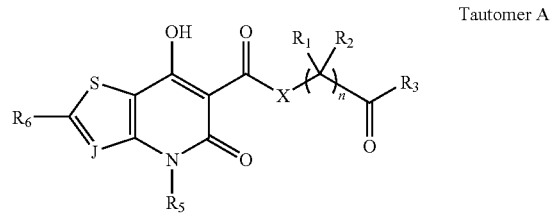

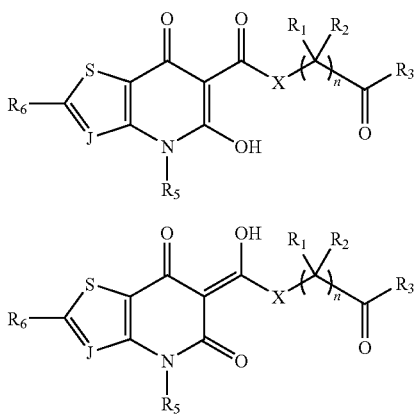

Compounds of the invention are depicted structurally and named as compounds in the "Tautomer A" form. However, it is specifically contemplated that the compounds may also exist in "Tautomer B" or "Tautomer C" form and compounds in "Tautomer B" form or "Tautomer C" form or another tautomeric form are expressly considered to be part of the invention.

Compounds of the present disclosure include, but are not limited to, compounds of Formula I and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. As used herein, the term "compound" encompasses not only the compound itself, but also a pharmaceutically acceptable salt thereof, a solvate thereof, a chelate thereof, a non-covalent complex thereof, a prodrug thereof, and mixtures of any of the foregoing. In some embodiments, the term "compound" encompasses the compound itself, pharmaceutically acceptable salts thereof, tautomers of the compound, pharmaceutically acceptable salts of the tautomers, and ester prodrugs such as ($C_1$-$C_4$)alkyl esters. In other embodiments, the term "compound: encompasses the compound itself, pharmaceutically acceptable salts thereof, tautomers of the compound, pharmaceutically acceptable salts of the tautomers.

As noted above, prodrugs also fall within the scope of chemical entities, for example, ester or amide derivatives of the compounds of Formula I. The term "prodrugs" includes any compounds that become compounds of Formula I when administered to a patient, e.g., upon metabolic processing of the prodrug. Examples of prodrugs include, but are not limited to, acetate, formate, benzoate, carbomethoxy, carboethoxy and like derivatives of functional groups (such as alcohol, carboxylic acid, ether, ester, or amine groups) in the compounds of Formula I. In some embodiments, the prodrugs of the compounds of Formula I are esters such as methyl, ethyl, propyl, butyl, pentyl, and hexyl esters.

The term "solvate" refers to the compound formed by the interaction of a solvent and a compound. Suitable solvates are pharmaceutically acceptable solvates, such as hydrates, including monohydrates and hemi-hydrates.

"Alkyl" refers to a saturated, branched, straight-chain, or cyclic monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and cyclopropan-1-yl, butyls such as butan-1-yl, butan-2-yl, 2-methyl-propan-1-yl, 2-methyl-propan-2-yl, cyclobutan-1-yl, tert-butyl, and the like. In certain embodiments, an alkyl group comprises from 1 to 20 carbon atoms. As used herein the term "lower alkyl" refers to an alkyl group comprising from 1 to 6 carbon atoms.

"Alkenyl" refers to an unsaturated branched, straight-chain, or cyclic hydrocarbon group having at least one carbon-carbon double bond derived by the removal of one hydrogen atom from a single carbon atom of a parent alkene. The group may be in either the Z- or E-form (cis or trans) about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. In certain embodiments, an alkenyl group has from 2 to 20 carbon atoms and in other embodiments, from 2 to 6 carbon atoms, i.e. "lower alkenyl."

"Alkynyl" refers to an unsaturated branched or straight-chain hydrocarbon having at least one carbon-carbon triple bond derived by the removal of one hydrogen atom from a single carbon atom of a parent alkyne. Typical alkynyl groups include, but are not limited to, ethynyl; propynyl; butynyl, 2-pentynyl, 3-pentynyl, 2-hexynyl, 3-hexynyl and the like. In certain embodiments, an alkynyl group has from 2 to 20 carbon atoms and in other embodiments, from 2 to 6 carbon atoms, i.e. "lower alkynyl."

"Alkoxy" refers to a radical —OR where R represents an alkyl group as defined herein. Representative examples include, but are not limited to, methoxy, ethoxy, propoxy, butoxy, cyclohexyloxy, and the like. Typical alkoxy groups include from 1 to 10 carbon atoms, from 1 to 6 carbon atoms or from 1 to 4 carbon atoms in the R group. Lower alkoxy groups include ($C_{1-6}$) alkyl groups and, in some embodiments, may include ($C_{1-4}$) alkyl groups.

"Alkylene" refers to a divalent saturated hydrocarbon group derived from a parent alkane by removal of two hydrogen atoms. Examples of alkylene group include, but are not limited to, —$CH_2$—, —$CH_2CH_2$—, —$CH(CH_3)$—, —$CH_2CH_2CH_2$—, —$CH_2C(CH_3)(H)$—, and the like.

"Alkenylene" refers to a divalent unsaturated hydrocarbon group having at least one carbon-carbon double bond derived by the removal of two hydrogen atoms from a parent alkene. The group may be in either the Z- or E-form (cis or trans) about the double bond(s). Examples of alkenylene groups, include, but are not limited to, —CH═CH—, —CH═C(H)$CH_2$—, —$CH_2$C(H)═C(H)$CH_2$—, and the like.

"Alkynylene" refers to a divalent unsaturated hydrocarbon group having at least one carbon-carbon triple bond derived by the removal of two hydrogen atoms from a parent alkyne. Example of alkynylene groups, include, but are not limited to, —C≡C—, —$CH_2$C≡C—, —$CH_2$C≡$CCH_2$—.

"Aryl" refers to a monovalent aromatic hydrocarbon group derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. For example, aryl includes 5- and 6-membered carbocyclic aromatic rings fused to a 5- to 7-membered heterocyclic ring containing 1 or more heteroatoms chosen from N, O, and S. In certain embodiments, an aryl group can comprise from 6 to 10 carbon atoms. Aryl, however, does not encompass or overlap in any way with heteroaryl, separately defined below. Hence, if one or more carbocyclic aromatic rings is fused with a heterocyclic aromatic ring, the resulting ring system is heteroaryl, not aryl, as defined herein.

"Arylalkyl" or "aralkyl" refers to an acyclic alkyl group in which one of the hydrogen atoms bonded to a carbon atom, typically, but not necessarily, a terminal carbon atom, is replaced with an aryl group. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. In certain embodiments, an arylalkyl group can be ($C_{6-30}$) arylalkyl, e.g., the alkyl group of the arylalkyl group can be ($C_{1-10}$) and the aryl moiety can be ($C_{5-20}$).

"Arylalkenyl" refers to an alkenyl group in which a bond to one of the hydrogen atoms of the alkenyl group is replaced with a bond to an aryl group.

"Arylalkynyl" refers to an alkynyl group in which a bond to one of the hydrogen atoms of the alkynyl group is replaced with a bond to an aryl group.

"Carbonyl" refers to the radical —C(O) group.

"Carboxy" refers to the radical —C(O)OH.

"Cyano" refers to the radical —CN.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In certain embodiments, the cycloalkyl group can be $C_{3-10}$ cycloalkyl, such as, for example, $C_{3-6}$ cycloalkyl.

"Heterocyclic", "heterocyclo" or "heterocyclyl" refer to a saturated or unsaturated, but non-aromatic, cyclic hydrocarbon group in which one or more carbon atoms (and any associated hydrogen atoms) are independently replaced with the same or different heteroatom and its associated hydrogen atoms, where appropriate. Typical heteroatoms to replace the carbon atom(s) include, but are not limited to, N, O, and S. Typical heterocyclyl groups include, but are not limited to, groups derived from epoxides, imidazolidine, morpholine, piperazine, piperidine, pyrazolidine, pyrrolidine, quinuclidine, tetrahydrofuran, tetrahydropyran and the like. Substituted heterocyclyl also includes ring systems substituted with one or more oxo (=O) or oxide (—O—) substituents, such as piperidinyl N-oxide, morpholinyl-N-oxide, 1-oxo-1-thiomorpholinyl and 1,1-dioxo-1-thiomorpholinyl.

"Heterocyclylalkyl" refers to an alkyl group in which one of the hydrogen atoms of the alkyl is replaced with a bond to a heterocyclyl group. Examples of heterocyclylalkyl groups, include, but are not limited to, morpholinylmethyl, morpholinylethyl, tetrahydrofuranylmethyl, piperidinylmethyl, and the like.

"Disease" refers to any disease, disorder, condition, symptom, or indication.

"Halo" or "halogen" refers to a fluoro, chloro, bromo, or iodo group.

"Haloalkyl" refers to an alkyl group in which at least one hydrogen is replaced with a halogen. Thus, the term "haloalkyl" includes monohaloalkyl(alkyl substituted with one halogen atom) and polyhaloalkyl (alkyl substituted with two or more halogen atoms). The term "perhaloalkyl" means, unless otherwise stated, an alkyl group in which each of the hydrogen atoms is replaced with a halogen atom. For example, the term "perhaloalkyl", includes, but is not limited to, trifluoromethyl, pentachloroethyl, 1,1,1-trifluoro-2-bromo-2-chloroethyl, and the like.

"Heteroaryl" refers to a monovalent heteroaromatic group derived by the removal of one hydrogen atom from a single atom of a parent heteroaromatic ring system. Heteroaryl encompasses 5- to 7-membered aromatic, monocyclic rings containing one or more, for example, from 1 to 4, or in certain embodiments, from 1 to 3, heteroatoms chosen from N, O, and S, with the remaining ring atoms being carbon; and polycyclic ring systems containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heteroaromatic ring fused to a 5- to 7-membered cycloalkyl ring or a carbocyclic aromatic ring and a 5- to 7-membered heteroaromatic ring fused to a 5- to 7-membered heterocyclic ring. For fused, bicyclic heteroaryl ring systems wherein only one of the rings contains one or more heteroatoms, the point of attachment may be at the heteroaromatic ring or the carbocyclic ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group can be between 5 to 20 membered heteroaryl, such as, for example, a 5 to 10 membered heteroaryl. In certain embodiments, heteroaryl groups can be those derived from thiophene, pyrrole, benzothiophene, benzofuran, indole, pyridine, quinoline, imidazole, oxazole, and pyrazine.

"Heteroarylalkyl" or "heteroaralkyl" refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl, and/or heteroarylalkynyl is used. In certain embodiments, the heteroarylalkyl group can be a 6 to 30 membered heteroarylalkyl, e.g., the alkyl moiety of the heteroarylalkyl can include 1 to 10 members and the heteroaryl moiety of the heteroarylalkyl can include from 5 to 20-members.

"Sulfonyl" refers to a radical —S(O)$_2$R where R is an alkyl, substituted alkyl, substituted cycloalkyl, substituted heterocyclyl, substituted aryl, or substituted heteroaryl group as defined herein. Representative examples include, but are not limited to, methylsulfonyl, ethylsulfonyl, propylsulfonyl, butylsulfonyl, and the like.

"Sulfanyl" refers to a radical —SR where R is an alkyl, substituted alkyl, substituted cycloalkyl, substituted heterocyclyl, substituted aryl, or substituted heteroaryl group as defined herein that may be optionally substituted as defined herein. Representative examples include, but are not limited to, methylthio, ethylthio, propylthio, butylthio, and the like.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereomers."

"Subject" includes mammals and humans. The terms "human" and "subject" are used interchangeably herein.

"Substituted" refers to a group in which one or more hydrogen atoms are each independently replaced with the same or different substituent(s). Typical substituents include, but are not limited to, —X, —$R_{11}$, —OH, =O, —OR, —$SR_{11}$, —SH, =S, —$NR_{11}R_{12}$, =$NR_{11}$, —$CX_3$, —$CF_3$, —CN, —$NO_2$, —$S(O)_2R_{11}$, —$OS(O_2)OH$, —$OS(O)_2R_{11}$, —$OP(O)(OR_{11})(OR_{12})$, —$C(O)R_{11}$, —$C(S)R_{11}$, —$C(O)OR_{11}$, —$C(O)NR_{11}R_{12}$, —C(O)OH, —$C(S)OR_{11}$, —$NR_{13}C(O)NR_{11}R_{12}$, —$NR_{13}C(S)NR_{11}R_{12}$, —$NR_{13}C(NR_1)NR_{11}R_{12}$, —$C(NR_{11})NR_{11}R_{12}$, —$S(O)_2NR_{11}R_{12}$, —$NR_{13}S(O)_2R_{11}$, —$NR_{13}C(O)R_{11}$, and —$S(O)R_{11}$ where each X is independently a halo; each $R_{11}$ and $R_{12}$ are independently hydrogen, alkyl, substituted alkyl, alkyl interrupted by one or more —O— or —S— groups, aryl, substituted aryl, arylalkyl, substituted arylalkyl, cycloalkyl, substituted cycloalkyl, heterocyclyl, substituted heterocyclyl, heteroaryl, substituted heteroaryl, heteroarylalkyl, substituted heteroarylalkyl, —$NR_{13}R_{14}$, $C(O)R_{13}$ or —$S(O)_2R_{13}$ or optionally $R_{11}$ and $R_{12}$ together with the atom to which $R_{11}$ and $R_{12}$ are attached form one or more heterocyclyl, substituted heterocyclyl, heteroaryl, or substituted heteroaryl rings; and $R_{13}$ and $R_{14}$ are independently hydrogen, alkyl, substituted alkyl, aryl, substituted aryl, arylalkyl, substituted arylalkyl, cycloalkyl, substituted cycloalkyl, heterocyclyl, substituted heterocyclyl, heteroaryl, substituted heteroaryl, heteroarylalkyl or substituted heteroarylalkyl, or optionally $R_{13}$ and $R_{14}$ together with the nitrogen atom to which $R_{13}$ and $R_{14}$ are attached form one or more heterocyclyl, substituted heterocyclyl, heteroaryl, or substituted heteroaryl rings. In certain embodiments, a tertiary amine or aromatic nitrogen may be substituted with on or more oxygen atoms to form the corresponding nitrogen oxide.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

In one aspect, the invention provides a composition of matter that includes at least one compound of Formula I:

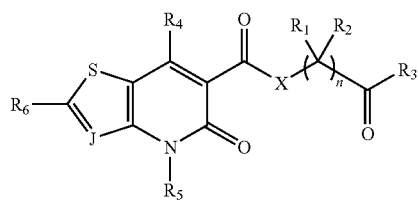

a pharmaceutically acceptable salt thereof, a tautomer thereof, or a pharmaceutically acceptable salt of the tautomer; or a solvate thereof, a chelate thereof, a non-covalent complex thereof, a prodrug thereof, or a mixture of any of the foregoing, wherein:

J is selected from $CR_7$ or N;

n is 1 to 6;

$R_1$ and $R_2$ are independently selected in each instance from H, lower alkyl, substituted lower alkyl, lower haloalkyl, or substituted lower haloalkyl, or $R_1$ and $R_2$ can join together to form a 3 to 6 membered ring or a substituted 3 to 6 membered ring;

X is selected from —$NR_a$—, —O—, —S—, or —($CR_b$ $R_c$)—, wherein $R_a$ is selected from H or lower alkyl, and $R_b$ and $R_c$ are independently selected from H, lower alkyl, substituted lower alkyl, lower haloalkyl, or substituted lower haloalkyl, or $R_b$ and $R_c$ can join together to form a 3 to 6 membered ring or a substituted 3 to 6 membered ring;

$R_3$ is selected from OH, SH, $NH_2$, lower alkyl, substituted lower alkyl, lower alkoxy, substituted lower alkoxy, or sulfanyl;

$R_4$ is selected from H, OH, lower alkoxy, SH, $NH_2$, $NHSO_2R_8$, or sulfonyl;

$R_5$ is selected from H, lower alkyl, or substituted lower alkyl;

$R_6$ and $R_7$ are independently selected from H, F, Cl, Br, I, alkyl, substituted alkyl, haloalkyl, perhaloalkyl, alkenyl, substituted alkenyl, alkynyl, substituted alkynyl, $NR_dR_e$, C(O) $R_8$, C(O)$OR_9$, $OR_9$, $SR_9$, $SO_2R_9$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, or —Y—$R_{10}$; or, $R_6$ and $R_7$ may join to form an optionally substituted 5 or 6 membered ring when J is $CR_7$, wherein:

Y is selected from —N($R_{11}$)—Z— or —Z—N($R_{11}$)—;

Z is selected from C(O), $SO_2$, alkylene, substituted alkylene, alkenylene, substituted alkenylene, alkynylene, or substituted alkynylene;

$R_8$ is selected from H, alkyl, substituted alkyl, alkenyl, substituted alkenyl, alkynyl, substituted alkynyl heterocyclyl, substituted heterocyclyl, aryl, substituted aryl, heteroaryl, or substituted heteroaryl;

$R_9$ is selected from H, alkyl, substituted alkyl, alkenyl, substituted alkenyl, alkynyl, or substituted alkynyl;

$R_{10}$ is selected from H, heterocyclyl, substituted heterocyclyl, aryl, substituted aryl, heteroaryl, or substituted heteroaryl;

$R_{11}$ is selected from H, lower alkyl, or substituted lower alkyl; and $R_d$ and $R_e$ are independently selected from H, lower alkyl, substituted lower alkyl, lower haloalkyl, or substituted lower haloalkyl, or $R_d$ and $R_e$ can join together to form a 3 to 6 membered ring or a substituted 3 to 6 membered ring.

In some embodiments, X is —($CR_bR_c$)—, and $R_b$ and $R_c$ are independently selected from H, lower alkyl, substituted lower alkyl, lower haloalkyl, or substituted lower haloalkyl, or $R_b$ and $R_c$ can join together to form a 3 to 6 membered ring or a substituted 3 to 6 membered ring. In some such embodiments, $R_b$ and $R_c$ are independently selected from H, lower alkyl, substituted lower alkyl, lower haloalkyl, or substituted lower haloalkyl. In still other such embodiments, $R_b$ and $R_c$ are independently selected from H and lower alkyl. In still further such embodiments, $R_b$ and $R_c$ are both H. In some such embodiments, n is 1. In some such embodiments, $R_1$ and $R_2$ are independently selected in each instance from H, lower alkyl, substituted lower alkyl, lower haloalkyl, or substituted lower haloalkyl. In still other such embodiments, $R_1$ and $R_2$ are independently selected in each instance from H, lower alkyl, or substituted lower alkyl. In still other such embodiments, $R_1$ and $R_2$ are both H. In some embodiments, J is $CR_7$, n is 1; $R_1$ is H or lower alkyl; $R_2$ is H; $R_3$ is OH; $R_4$ is OH; and $R_b$ and $R_c$ are both H. In other embodiments, J is N, n is 1; R is H or lower alkyl; $R_2$ is H; $R_3$ is OH; $R_4$ is OH; and $R_b$ and $R_c$ are both H.

In some embodiments where X is —($CR_bR_c$)—, the CPH1 $IC_{50}$ value divided by the PHD2 $IC_{50}$ value is greater than 5, greater than 10, greater than 15, greater than 20, greater than 25, or greater than 30. In some such embodiments, the CPH1 $IC_{50}$ value divided by the PHD2 $IC_{50}$ value is greater than 10.

In some embodiments, $R_1$ and $R_2$ are not both H if X is —$NR_a$—; $R_a$ is H; and n is 1.

In some embodiments, n is 1, $R_1$ and $R_2$ are both H.

In some embodiments, at least one of $R_1$ and $R_2$ is not H. In some such embodiments, at least one of $R_1$ and $R_2$ is a lower alkyl such as a ($C_1$-$C_4$)alkyl. In some such embodiments, one of $R_1$ and $R_2$ is H and the other of $R_1$ and $R_2$ is a lower alkyl. In some such embodiments, at least one of $R_1$ and $R_2$ is a methyl group, and in some such embodiments, the other of $R_1$ and $R_2$ is a methyl group.

In some embodiments, J is $CR_7$. In other embodiments, J is N. In some such embodiments, the compound of Formula I is a compound of Formula IA where the variable have any of the definitions provided in any of the embodiments.

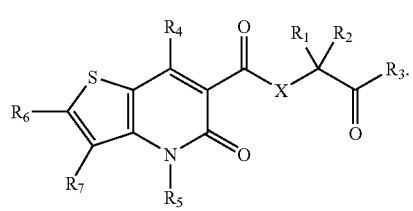

IA

In other such embodiments, the compound of Formula I is a compound of Formula IB where the variables have any of the definitions provided in any of the embodiments

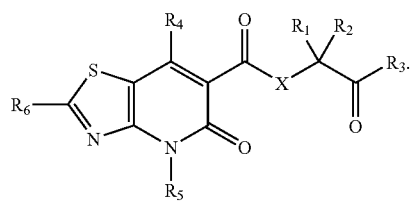

IB

In some embodiments, $R_3$ is OH.
In some embodiments, $R_4$ is OH.
In some embodiments, X is —$NR_a$—. In some such embodiments, X is —NH—.
In other embodiments, X is —($CR_bR_c$)—. In some embodiments, $R_b$ and $R_c$ are independently chosen from H and lower alkyl. In some such embodiments, $R_b$ and $R_c$ are independently selected from H and methyl. In some such embodiments, $R_b$ and $R_c$ are both H.

In some embodiments, at least one of $R_6$ or $R_7$ is a substituted or unsubstituted aryl, a substituted or unsubstituted heteroaryl, a substituted or unsubstituted cycloalkyl, or a substituted or unsubstituted heterocyclyl group. In some such embodiments, at least one of $R_6$ or $R_7$ is a heterocyclyl group. In other such embodiments, at least one of $R_6$ or $R_7$ is a heteroaryl group. In other such embodiments, at least one of $R_6$ or $R_7$ is a phenyl or substituted phenyl group.

In some embodiments, $R^6$ is selected from an aryl or a substituted aryl group. In some embodiments, aryl and substituted aryl groups include phenyl, or phenyl substituted with from one to three substituents independently selected from —F, —Cl, —Br, —$CF_3$, —$CO_2H$, —C(=O)O—($C_1$-$C_4$)

alkyl, —CN, —OH, —O—($C_1$-$C_4$)alkyl, —($C_1$-$C_4$)alkyl, —C(=O)—$NH_2$, —C(=O)NH—($C_1$-$C_4$)alkyl, —C(=O)N—(($C_1$-$C_4$)alkyl)$_2$, —$NH_2$, —NH—($C_1$-$C_4$)alkyl, or —N(($C_1$-$C_4$)alkyl)$_2$. In some embodiments, aryl groups include phenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-trifluoromethylphenyl, 3-trifluoromethylphenyl, 4-trifluoromethylphenyl, phenyl substituted in the 2-, 3-, or 4-position with a $CO_2H$ group, 2-methylphenyl, 3-methylphenyl, 4-methylphenyl, 2-methoxyphenyl, 3-methoxyphenyl, 4-methoxyphenyl, 2-hydroxyphenylm 3-hydroxyphenyl, or 4-hydroxyphenyl.

In some embodiments, $R^6$ is selected from —H, —Br, —$CF_3$, —($C_1$-$C_4$)alkyl, aryl, substituted aryl, heteroaryl, substituted heteroaryl, heterocyclyl, cycloalkyl, or —$CO_2H$. In some embodiments where $R^6$ is a heteroaryl group or a substituted heteroaryl group, the heteroaryl is selected from pyridine, pyrimidine, thiophene, thiazole, quinoline, isoquinoline, oxazole, isoxazole, or furan.

In some embodiments, at least one of $R_6$ or $R_7$ is independently selected from halo or a moiety substituted with at least one halo. For example, in some embodiments, at least one of $R_6$ or $R_7$ is haloalkyl. In some embodiments, at least one of $R_6$ or $R_7$ is a perhaloalkyl. In some such embodiments, the perhaloalkyl is a perfluoroalkyl group such as $CF_3$.

In some embodiments, n is 1.

In some embodiments, $R_1$ and $R_2$ are independently chosen from H and lower alkyl. In some such embodiments, $R_1$ and $R_2$ are both H. In some such embodiments, n is 1. In still other such embodiments, X is —($CR_bR_c$)— and $R_b$ and $R_c$ are selected from H and lower alkyl, and in some such embodiments, $R_b$ and $R_c$ are both H. Therefore, in some embodiments $R_1$, $R_2$, $R_b$, and $R_c$ are all H and n is 1.

In some embodiments, J is $CR_7$, n is 1; $R_1$ is H or lower alkyl; $R_2$ is H; $R_3$ is OH; $R_4$ is OH; X is —$NR_a$— wherein $R_a$ is H, or X is —($CR_bR_c$)— wherein $R_b$ and $R_c$ are both H.

In some embodiments, J is N, n is 1; $R_1$ is H or lower alkyl; $R_2$ is H; $R_3$ is OH; $R_4$ is OH; X is —$NR_a$— wherein $R_a$ is H, or X is —($CR_bR_c$)— wherein $R_b$ and $R_c$ are both H.

In some embodiments, $R_5$ is H. In other embodiments, $R_5$ is a lower alkyl group. In some such embodiments, $R_5$ is a methyl. In still other embodiments, $R_5$ is a substituted lower alkyl selected from an arylalkyl, a heteroarylalkyl, a heterocyclylalkyl, a cycloalkylalkyl, a hydroxyalkyl, an alkoxyalkyl, or a haloalkyl.

In some embodiments, J is $CR_7$ and $R_6$ and $R_7$, together with the carbon atoms to which they are attached, join to form a 6-membered carbocyclic aromatic ring that may be optionally substituted with up to three substituents. In some such embodiments, the compound has the Formula IC

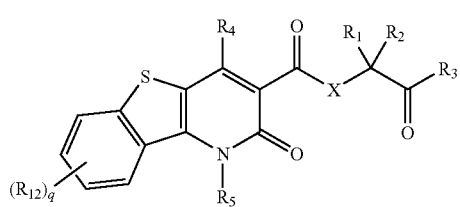

IC where $R_1$-$R_5$ have any of the values of any of the embodiments, q is 0, 1, or 2, and $R_{12}$ is selected from H, F, Cl, Br, I, alkyl, substituted alkyl, haloalkyl, perhaloalkyl, alkenyl, substituted alkenyl, alkynyl, substituted alkynyl, C(O)$R_{13}$, C(O)

$OR_{14}$, $OR_{14}$, $SR_{14}$, $SO_2R_{14}$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, or substituted heterocyclylalkyl; $R_{13}$ is selected from H, alkyl, substituted alkyl, alkenyl, substituted alkenyl, alkynyl, substituted alkynyl heterocyclyl, substituted heterocyclyl, aryl, substituted aryl, heteroaryl, or substituted heteroaryl; and $R_{14}$ is selected from H, alkyl, substituted alkyl, alkenyl, substituted alkenyl, alkynyl, or substituted alkynyl.

In other embodiments, the compound is selected from any one or all of those listed below or is a salt thereof, a tautomer thereof, or a salt of the tautomer:

N-((2-(4-chlorophenyl)-7-hydroxy-4-methyl-5-oxo-4,5-dihydro[1,3]thiazolo[4,5-b]pyridin-6-yl)carbonyl)glycine;

N-((7-hydroxy-2,4-dimethyl-5-oxo-4,5-dihydro[1,3]thiazolo[4,5-b]pyridin-6-yl)carbonyl)glycine;

2-(7-hydroxy-4-methyl-5-oxo-4,5-dihydrothieno[3,2-b]pyridine-6-carboxamido)acetic acid;

2-(7-hydroxy-3,4-dimethyl-5-oxo-4,5-dihydrothieno[3,2-b]pyridine-6-carboxamido)acetic acid;

2-(2-(4-chlorophenyl)-7-hydroxy-4-methyl-5-oxo-4,5-dihydrothieno[3,2-b]pyridine-6-carboxamido)acetic acid;

2-(2-bromo-7-hydroxy-4-methyl-5-oxo-4,5-dihydrothieno[3,2-b]pyridine-6-carboxamido)acetic acid;

(S)-2-(7-hydroxy-3,4-dimethyl-5-oxo-4,5-dihydrothieno[3,2-b]pyridine-6-carboxamido)propanoic acid;

2-(7-hydroxy-4-methyl-5-oxo-3-phenyl-2-(trifluoromethyl)-4,5-dihydrothieno[3,2-b]pyridine-6-carboxamido)acetic acid;

N-((4-hydroxy-1-methyl-2-oxo-1,2-dihydro[1]benzothieno[3,2-b]pyridin-3-yl)carbonyl)glycine;

N-((4-hydroxy-1-methyl-2-oxo-1,2-dihydro[1]benzothieno[3,2-b]pyridin-3-yl)carbonyl)-L-alanine;

2-(2-(4-fluorophenyl)-7-hydroxy-4-methyl-5-oxo-4,5-dihydrothieno[3,2-b]pyridine-6-carboxamido)acetic acid;

2-(7-hydroxy-4-methyl-5-oxo-2-(pyrimidin-5-yl)-4,5-dihydrothieno[3,2-b]pyridine-6-carboxamido)acetic acid;

2-(7-hydroxy-4-methyl-2-(2-methylpyridin-3-yl)-5-oxo-4,5-dihydrothieno[3,2-b]pyridine-6-carboxamido)acetic acid;

2-(7-hydroxy-4-methyl-2-(3-methylthiophen-2-yl)-5-oxo-4,5-dihydrothieno[3,2-b]pyridine-6-carboxamido)acetic acid;

2-(7-hydroxy-4-methyl-5-oxo-2-phenyl-4,5-dihydrothieno[3,2-b]pyridine-6-carboxamido)acetic acid;

2-(2-bromo-7-hydroxy-3,4-dimethyl-5-oxo-4,5-dihydrothieno[3,2-b]pyridine-6-carboxamido)acetic acid; or 4-(2-bromo-7-hydroxy-4-methyl-5-oxo-4,5-dihydrothieno[3,2-b]pyridin-6-yl)-4-oxobutanoic acid.

In other embodiments, the compound is selected from any one or all of those listed below or is a salt thereof, a tautomer thereof, or a salt of the tautomer:

2-(2-(3,6-dihydro-2H-pyran-4-yl)-7-hydroxy-4-methyl-5-oxo-4,5-dihydrothieno[3,2-b]pyridine-6-carboxamido)acetic acid;

4-(6-((carboxymethyl)carbamoyl)-7-hydroxy-4-methyl-5-oxo-4,5-dihydrothieno[3,2-b]pyridin-2-yl)benzoic acid;

2-(2-(2-chlorophenyl)-7-hydroxy-4-methyl-5-oxo-4,5-dihydrothieno[3,2-b]pyridine-6-carboxamido)acetic acid;

2-(2-cyclopropyl-7-hydroxy-4-methyl-5-oxo-4,5-dihydrothieno[3,2-b]pyridine-6-carboxamido)acetic acid;

4-(7-hydroxy-4-methyl-5-oxo-2-phenyl-4,5-dihydrothieno[3,2-b]pyridin-6-yl)-4-oxobutanoic acid;

2-(2-(2-chlorophenyl)-7-hydroxy-3,4-dimethyl-5-oxo-4,5-dihydrothieno[3,2-b]pyridine-6-carboxamido)acetic acid;

6-((carboxymethyl)carbamoyl)-7-hydroxy-3,4-dimethyl-5-oxo-4,5-dihydrothieno[3,2-b]pyridine-2-carboxylic acid;

2-(2-(2-chlorophenyl)-7-hydroxy-4-methyl-5-oxo-4,5-dihydrothiazolo[4,5-b]pyridine-6-carboxamido)acetic acid;

2-(2-cyclopropyl-7-hydroxy-4-methyl-5-oxo-4,5-dihydrothiazolo[4,5-b]pyridine-6-carboxamido)acetic acid;

2-(7-hydroxy-4-methyl-5-oxo-2-(thiophen-2-yl)-4,5-dihydrothiazolo[4,5-b]pyridine-6-carboxamido)acetic acid;

2-(7-hydroxy-4-methyl-5-oxo-2-(pyridin-3-yl)-4,5-dihydrothiazolo[4,5-b]pyridine-6-carboxamido)acetic acid;

2-(4-benzyl-2-bromo-7-hydroxy-5-oxo-4,5-dihydrothieno[3,2-b]pyridine-6-carboxamido)acetic acid; or 2-(4-benzyl-7-hydroxy-2-methyl-5-oxo-4,5-dihydrothiazolo[4,5-b]pyridine-6-carboxamido)acetic acid.

Compounds of the present disclosure can contain one or more chiral centers. Such compounds can be prepared or isolated as pure stereoisomers, i.e., as individual enantiomers or diastereomers, or as stereoisomer-enriched mixtures. All such stereoisomers, and enriched mixtures thereof, are included within the scope of the present disclosure. Pure stereoisomers, and enriched mixtures thereof, can be prepared using, for example, optically active starting materials or stereoselective reagents well-known in the art. Alternatively, racemic mixtures of such compounds can be separated using, for example, chiral column chromatography, chiral resolving agents and the like.

In some embodiments, the composition of matter is a salt. Such salts may be anhydrous or associated with one or more molecules of water as a hydrate.

In some embodiments, the composition of matter is a prodrug. In some such embodiments, the composition of matter is a ($C_1$-$C_6$)alkyl ester such as a methyl, ethyl, propyl, butyl, pentyl, or hexyl ester.

Also provided herein are pharmaceutical formulations that include at least one pharmaceutically acceptable carrier, excipient, or diluent, and a therapeutically effective amount of the composition of matter any of the embodiments described herein. In such embodiments, the composition of matter is present in an amount effective for the treatment of at least one disease selected from ischemia, anemia, wound healing, auto-transplantation, allo-transplantation, xeno-transplantation, systemic high blood pressure, thalassemia, diabetes, cancer, or an inflammatory disorder.

Further provided are pharmaceutical formulations that include at least one pharmaceutically acceptable carrier, and a therapeutically effective amount of the composition of matter of any of the embodiments described herein in combination with at least one additional compound such as an erythropoiesis stimulating agent or a chemotherapeutic agent.

Additionally provided is a method of increasing or stabilizing HIF levels or activity in a subject by administering to the subject the composition of matter of any of the embodiments described herein.

Further provided is a method of treating a condition where it is desired to modulate HIF activity comprising administering to a subject the composition of matter of any of the embodiments described herein. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

Also provided is a method of treating a hypoxic or ischemic related disorder in a subject comprising administering to a subject the composition of matter of any of the embodiments described herein.

Also provided is a method of treating anemia in a subject comprising administering to a subject the composition of matter of any of the embodiments described herein.

Further provided is a method of modulating the amount of HIF in a cell comprising contacting the cell with the composition of matter of any of the embodiments described herein.

The compounds of the invention may also be used to prepare medicaments or in methods for stimulating erythropoiesis in a subject. Such methods and medicaments utilize a compound of any of the embodiments of the invention. In such methods, a compound of any of the embodiments is typically administered to a subject such as a human subject in a therapeutically effective amount.

Additionally provided is a method of increasing the amount of hemoglobin F in a subject comprising administering to the subject the composition of matter of any of the embodiments described herein.

Also provided is a method of modulating angiogenesis in a subject comprising administering to the subject the composition of matter of any of the embodiments described herein.

Additionally provided is a method of treating at least one disease in a patient in need of such treatment comprising administering to the patient a therapeutically effective amount of the composition of matter of any of the embodiments described herein. In some such embodiments, the at least one disease is selected from ischemia, anemia, wound healing, auto-transplantation, allo-transplantation, xeno-transplantation, systemic high blood pressure, thalassemia, diabetes, cancer, or an inflammatory disorder.

Also provided is a method of inhibiting HIF hydroxylation in a subject comprising administering to the subject the composition of matter of any of the embodiments described herein.

In some embodiments, the HIF PHD inhibitory activity $IC_{50}$ value of the composition of matter is 40 μM or less. In other embodiments, the HIF PHD inhibitory activity $IC_{50}$ value of the composition of matter is 10 μM or less. In still other embodiments, the HIF PHD inhibitory activity $IC_{50}$ value of the composition of matter is 100 nM or less, whereas in others it is 10 nM or less.

In some embodiments, the composition of matter of any of the embodiments is used in the preparation of a pharmaceutical formulation or medicament.

In some such embodiments, the composition of matter of any of the embodiments is used in the preparation of a medicament for increasing or stabilizing HIF levels or activity in a subject.

In some such embodiments, the composition of matter of any of the embodiments is used in the preparation of a medicament for treating a condition where it is desired to modulate HIF activity. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

In some embodiments, the composition of matter of any of the embodiments is used in the preparation of a medicament for treating a hypoxic or ischemic related disorder in a subject.

In some embodiments, the composition of matter of any of the embodiments is used in the preparation of a medicament for modulating the amount if HIF in a cell. In some embodiments, the composition of matter according to any of the embodiments is used to modulate the amount of HIF in a cell.

In some embodiments, the composition of matter of any of the embodiments is used in the preparation of a medicament for modulating angiogenesis in a subject.

In some embodiments, the composition of matter of any of the embodiments is used in the preparation of a medicament for inhibiting HIF hydroxylation in a subject.

In some embodiments, the composition of matter of any of the embodiments is used in the preparation of a medicament for treating anemia.

In some embodiments, the composition of matter of any of the embodiments is used in a method for increasing the level of erythropoietin in the blood of a subject.

The phrase "composition of matter" as used herein is intended to encompass the compounds of the invention, pharmaceutically acceptable salts thereof, tautomers thereof, and pharmaceutically acceptable salts of the tautomer. It may also includes solvates, chelates, non-covalent complexes, prodrugs and mixtures of these in addition to a product comprising the specified ingredients (and in the specified amounts, if indicated), as well as any product which results, directly or indirectly, from combination of the specified ingredients in the specified amounts. By "pharmaceutically acceptable" it is meant that the carrier, excipient, or diluent is compatible with the other ingredients of the formulation and is not deleterious to the recipient thereof.

Composition formulation may improve one or more pharmacokinetic properties (e.g., oral bioavailability, membrane permeability) of a compound of the invention (herein referred to as the active ingredient).

The pharmaceutical compositions or formulations for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The compounds of the invention can be prepared using the general synthetic route shown below in Scheme 1 and described more fully in the Examples.

The invention is further described by reference to the following examples, which are intended to exemplify the claimed invention but not to limit it in any way.

EXAMPLES

Unless otherwise stated, all compounds were obtained from commercial sources or were prepared using the methods and experimental procedures described herein. The following Abbreviations are used to refer to various reagents and solvents:

| AcOH | Acetic Acid |
|---|---|
| DCM | Dichloromethane |
| DIPEA | Diisopropylethylamine |
| DMF | N,N-Dimethylformamide |
| DMSO | Dimethylsulfoxide |
| EtOAc | Ethyl Acetate |
| EtOH | Ethanol |
| MeOH | Methanol |
| TEA | Triethylamine |
| TFA | Trifluoroacetic acid |
| TFAA | Trifluoroacetic anhydride |
| THF | Tetrahydrofuran |
| TR-FRET | Time Resolved-Fluorescence Resonance Energy Transfer |

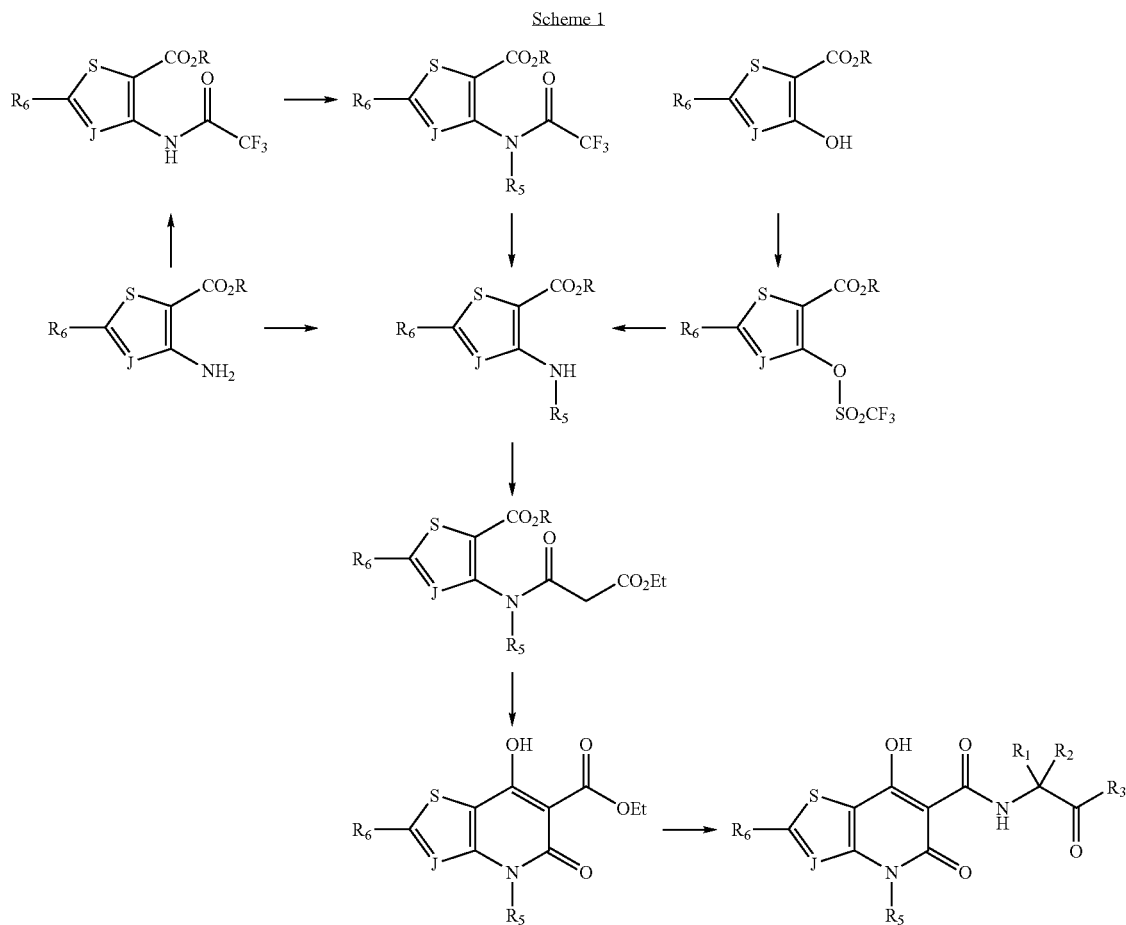

Scheme 1

Method 1

Preparation of N-((7-Hydroxy-2,4-dimethyl-5-oxo-4,5-dihydro[1,3]thiazolo[4,5-b]pyridin-6-yl)carbonyl)glycine

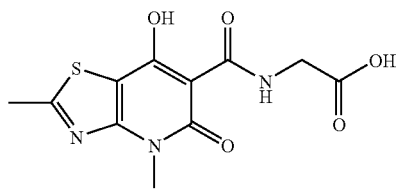

(a) Ethyl 4-hydroxy-2-methylthiazole-5-carboxylate. This compound was prepared according to the procedure of Baasner, B. et al. EP 0422470A2: Thiazolecarboxylic acid amide derivatives in 23% yield. MS (ESI) m/z: Calculated; 187.0: Observed; 188.1.

(b) Ethyl 2-methyl-4-(trifluoromethylsulfonyloxy)thiazole-5-carboxylate. Triflic anhydride (2.26 g, 8.01 mmol) was added to a solution of TEA (1.12 mL, 8.01 mmol) and ethyl 4-hydroxy-2-methylthiazole-5-carboxylate (1.00 g, 5.34 mmol) in DCM (20 mL) at 0° C. and the mixture was stirred for 1 hour at 0° C. Water was added, and the resulting layers were separated. The organic layer was dried over $MgSO_4$ and evaporated. Purification by column chromatography (EtOAc/hexane) gave the title compound. MS (ESI) m/z: Calculated; 319.0: Observed; 320.0. $^1$H NMR (400 MHz, $CDCl_3$) δ ppm 4.39 (2H, q, J=7.0 Hz), 2.71 (3H, s), 1.39 (3H, t, J=7.1 Hz).

(c) Ethyl 2-methyl-4-(methylamino)thiazole-5-carboxylate. Methylamine (0.75 g, 24.0 mmol) was added to a solution of ethyl 2-methyl-4-(trifluoromethylsulfonyloxy)thiazole-5-carboxylate (2.55 g, 8.0 mmol) in 1,4-dioxane (20 mL). The mixture was heated in a sealed tube to 90° C. for 6 hours, then cooled to room temperature. The solid that formed was filtered off, the filtrate was washed with water once, dried over $MgSO_4$ and evaporated. Purification by column chromatography (EtOAc/hexane) gave the title compound. $^1$H NMR (400 MHz, $CDCl_3$) δ ppm 6.65 (1H, br. s.), 4.25 (2H, q, J=7.0 Hz), 3.14 (3H, d, J=5.1 Hz), 2.61 (3H, s), 1.31 (3H, t, J=7.0 Hz).

(d) Ethyl 7-hydroxy-2,4-dimethyl-5-oxo-4,5-dihydrothiazolo[4,5-b]pyridine-6-carboxylate. Ethyl 3-chloro-3-oxopropanoate (1.28 g, 8.50 mmol) was slowly added to a solution of N,N-diisopropylethylamine (1.10 g, 8.50 mmol) and ethyl 2-methyl-4-(methylamino)thiazole-5-carboxylate (0.85 g, 4.25 mmol), and the mixture was stirred at room temperature for 3 hours. Water was added, and the mixture was extracted with EtOAc three times. The combined organic layers were dried over $MgSO_4$ and evaporated to give an oil (0.75 g). The oil was dissolved in EtOH (10 mL) and sodium methoxide (8.50 mmol, 1 M in EtOH, 8.5 mL) was added. The mixture was stirred at room temperature for 2 hours, and the resulting suspension was filtered and washed with $Et_2O$ once, MeOH once, and water to give the title compound. MS (ESI) m/z: Calculated; 268.1: Observed; 269.1.

(e) tert-Butyl 2-(7-hydroxy-2,4-dimethyl-5-oxo-4,5-dihydrothiazolo[4,5-b]pyridine-6-carboxamido)acetate. N,N-diisopropylethylamine (0.25 g, 2.0 mmol), tert-butyl glycine ester hydrochloride (0.33 g, 2.0 mmol) and ethyl 7-hydroxy-2,4-dimethyl-5-oxo-4,5-dihydrothiazolo[4,5-b]pyridine-6-carboxylate (0.35 g, 1.31 mmol) were heated at 90° C. for 5 hours in 1,4-dioxane (5 mL). The mixture was cooled to room temperature and concentrated to about ¼ of the original volume. $Et_2O$ (5 mL) was added, and the resulting suspension was filtered and washed with $Et_2O$ to give a solid. This material was washed with cold MeOH (0.5 mL) to give the title compound. MS (ESI) m/z: Calculated; 353.1: Observed; 298.1 (M-tert-butyl+H$^+$). $^1$H NMR (400 MHz, $CDCl_3$) δ ppm 10.52-10.83 (1H, m), 4.11 (2H, d, J=5.3 Hz), 3.81 (3H, s), 2.83 (3H, s), 1.52 (9H, s)

(f) N-((7-Hydroxy-2,4-dimethyl-5-oxo-4,5-dihydro[1,3]thiazolo[4,5-b]pyridin-6-yl)carbonyl)glycine. tert-Butyl 2-(7-hydroxy-2,4-dimethyl-5-oxo-4,5-dihydrothiazolo[4,5-b]pyridine-6-carboxamido)acetate (0.035 g, 0.10 mmol) was stirred in TFA (1 mL) for 30 minutes and then water was added (5 mL). The resulting suspension was filtered and washed with water several times to give the title compound in 71% yield. MS (ESI) m/z: Calculated; 297.0: Observed; 298.1. $^1$H NMR (400 MHz, DMSO-$d_6$) δ ppm 10.35-10.59 (1H, m), 4.11 (2H, d, J=5.5 Hz), 3.69 (3H, s), 2.85 (3H, s).

Method 2

Preparation of N-((2-(4-Chlorophenyl)-7-hydroxy-4-methyl-5-oxo-4,5-dihydro[1,3]thiazolo[4,5-b]pyridin-6-yl)carbonyl)glycine

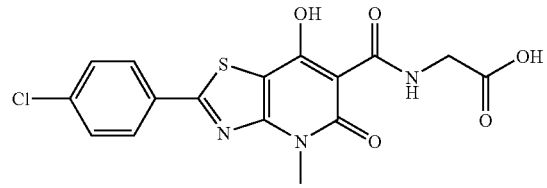

(a) Methyl 2-(methylthio)-4-(2,2,2-trifluoroacetamido)thiazole-5-carboxylate. Trifluoroacetic anhydride (7.35 g, 35.0 mmol) was added to a solution of 4-amino-2-methylthio-5-thiazolecarboxylic acid methyl ester (6.50 g, 31.8 mmol, commercially available from Fluorochem Products, West Columbia, S.C.) and N,N-diisopropylethylamine (4.52 g, 35.0 mmol) at 0° C. and the ice bath was removed. The mixture was then stirred for 1 hour, diluted with water, and the layers were separated. The organic layer was dried over $MgSO_4$, concentrated in vacuo, and purified by column chromatography (EtOAc/hexane) to give the title compound in 94% yield. $^1$H NMR (400 MHz, $CDCl_3$) δ ppm 10.78 (1H, s), 3.91 (3H, s), 2.76 (3H, s).

(b) Methyl 4-(methylamino)-2-(methylthio)thiazole-5-carboxylate. Iodomethane (4.61 g, 32.5 mmol) was added to a suspension of potassium carbonate (6.90 g, 50.0 mmol) and methyl 2-(methylthio)-4-(2,2,2-trifluoroacetamido)thiazole-5-carboxylate (7.50 g, 25.0 mmol) in DMF (60 mL) in a heavy-walled reaction vessel. The tube was sealed, and the reaction was heated at 60° C. for 2 hours. The mixture was cooled to room temperature, diluted with EtOAc (150 mL) and washed with water three times and brine once. The organic layer was dried over $MgSO_4$ and concentrated in vacuo. The resulting solid was dissolved in MeOH (20 mL) and treated with NaOMe (1.0M in MeOH, 35 mL, 35.0 mmol), and the mixture was stirred for 1 hour. Water (100 mL) was added, and the mixture was extracted with DCM three times. The combined organic layers were dried over $MgSO_4$ and concentrated in vacuo to give the title compound in 99% yield. MS (ESI) m/z: Calculated; 218.0: Observed;

219.0. ¹H NMR (400 MHz, CDCl₃) δ ppm 6.68 (1H, br s), 3.77 (3H, s), 3.14 (3H, d, J=5.1 Hz), 2.66 (3H, s).

(c) Ethyl 7-hydroxy-4-methyl-2-(methylthio)-5-oxo-4,5-dihydrothiazolo[4,5-b]pyridine-6-carboxylate. This compound was prepared as in Method 1, step c in 73% yield. MS (ESI) m/z: Calculated; 300.0: Observed; 301.1. ¹H NMR (400 MHz, DMSO-d₆) δ ppm 13.24 (1H, s), 4.31 (2H, q, J=7.0 Hz), 3.56 (3H, s), 2.82 (3H, s), 1.29 (3H, t, J=7.1 Hz).

(d) tert-Butyl 2-(7-hydroxy-4-methyl-2-(methylthio)-5-oxo-4,5-dihydrothiazolo[4,5-b]pyridine-6-carboxamido)acetate. This compound was prepared as described in Method 1, step d in 82% yield. MS (ESI) m/z: Calculated; 385.1: Observed; 330.0 (M-tert-butyl+H⁺). ¹H NMR (400 MHz, DMSO-d₆) δ ppm 10.41 (1H, br s), 4.08 (2H, d, J=5.7 Hz), 3.65 (3H, s), 2.83 (3H, s), 1.44 (9H, s).

(e) N-((2-(4-Chlorophenyl)-7-hydroxy-4-methyl-5-oxo-4,5-dihydro[1,3]thiazolo[4,5-b]pyridin-6-yl)carbonyl)glycine. Copper(I) thiophene-2-carboxylate (55 mg, 0.3 mmol), 4-chlorophenylboronic acid (75 mg, 0.5 mmol), tris(dibenzylideneacetone)dipalladium (9 mg, 0.010 mmol), tri(2-furyl)phosphine (18 mg, 0.08 mmol), and tert-butyl 2-(7-hydroxy-4-methyl-2-(methylthio)-5-oxo-3a,4,5,7a-tetrahydrothiazolo[4,5-b]pyridine-6-carboxamido)acetate (94 mg, 0.24 mmol) were mixed in THF (1 mL), and then placed under argon atmosphere. The mixture was heated at 65° C. overnight, silica gel was added, and the solvent was removed in vacuo. Purification of the fused silica gel by column chromatography provided an impure solid, which was taken directly to the next step. MS (ESI) m/z: Calculated; 449.1: Observed; 394.0 (M-tert-butyl+H⁺). This material was dissolved in TFA (1 mL) and stirred for 15 minutes. Water (5 mL) was added, and the resulting suspension was filtered and washed with water several times, then once with MeOH to give the title compound. MS (ESI) m/z: Calculated; 393.0: Observed; 394.0. ¹H NMR (400 MHz, DMSO-d₆) δ ppm 10.41-10.54 (1H, m), 8.17 (2H, d, J=8.4 Hz), 7.68 (2H, d, J=8.6 Hz), 4.15 (2H, d, J=5.9 Hz), 3.78 (3H, s).

Method 3

Preparation of Ethyl 7-hydroxy-4-methyl-5-oxo-4,5-dihydrothieno[3,2-b]pyridine-6-carboxylate

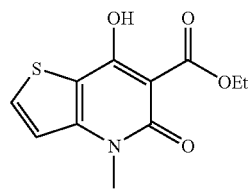

(a) Methyl 3-(3-ethoxy-N-methyl-3-oxopropanamido)thiophene-2-carboxylate. At room temperature under Argon, a solution of methyl 3-aminothiophene-2-carboxylate (11.79 g, 75.0 mmol, commercially available from Aldrich, Milwaukee, Wis.) in 70 mL DMF was treated with K₂CO₃ (3.87 g). The resulting suspension was treated dropwise with iodomethane (4.90 mL, 78.8 mmol), stirred for 1 hour, heated to 60° C. for 12 hours, treated with additional iodomethane (4.90 mL, 78.8 mmol), and stirred for 5 hours at 60° C. The mixture was cooled to room temperature, diluted with EtOAc, washed with water (1×), 0.1M aqueous HCl (1×), and brine (1×), dried over MgSO₄ and evaporated to give a beige solid (7.10 g). A solution of this crude material (6.73 g, 39.3 mmol) in 30 mL DMF and 3 mL DIEA at 24° C. was treated dropwise with ethyl malonoyl chloride (5.20 mL, 41.3 mmol) and stirred (strongly exothermic) for 30 minutes. The mixture was diluted with EtOAc and washed with water (1×), brine (1×), dried over MgSO₄ and evaporated. A brown oil resulted (10.78 g), which was used in the next step without further purification. MS (ESI) m/z: Calculated; 285.3: Observed; 286.1.

(b) Ethyl 7-hydroxy-4-methyl-5-oxo-4,5-dihydrothieno[3,2-b]pyridine-6-carboxylate. Crude methyl 3-(3-ethoxy-N-methyl-3-oxopropanamido)thiophene-2-carboxylate (1.00 g, 3505 µmol) was dissolved in THF (6 mL), treated with 6 mL of a NaOEt in EtOH solution (freshly prepared from 161 mg Na in 6 mL EtOH). During the addition, a yellow precipitate formed. The mixture was stirred for 30 minutes, and the resulting precipitate was collected by filtration, washed with Et₂O, and dried in vacuo. The slightly yellow solid was triturated in MeOH, collected by filtration, and dried in vacuo, which provided in the title compound as a white solid (450 mg). MS (ESI) m/z: Calculated; 253.3: Observed; 254.1. ¹H NMR (300 MHz, DMSO-d₆) δ ppm 7.56 (1H, br. s), 7.05 (1H, br. d, J=5.3 Hz), 4.01 (2H, q, J=7.1 Hz), 3.34 (3H, s), 1.18 (3H, t, J=7.0 Hz).

Method 4

Preparation of 2-(7-Hydroxy-4-methyl-5-oxo-4,5-dihydrothieno[3,2-b]pyridine-6-carboxamido)acetic Acid

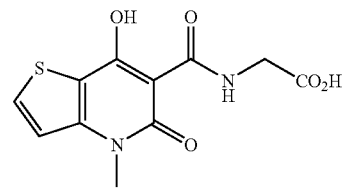

(a) Methyl 2-(7-hydroxy-4-methyl-5-oxo-4,5-dihydrothieno[3,2-b]pyridine-6-carboxamido)acetate. A mixture of methyl 2-aminoacetate hydrochloride (291 mg, 2317 µmol) and ethyl 7-hydroxy-4-methyl-5-oxo-4,5-dihydrothieno[3,2-b]pyridine-6-carboxylate (489 mg, 1931 µmol) in 15 mL dioxane was heated to 100° C. in a sealed tube and stirred for 15 hours. The mixture was cooled to room temperature, and the resulting suspension was added dropwise to 100 mL ice-water. The precipitate was collected by filtration, washed with H₂O, and dried in vacuo. The solids were triturated with Et₂O, collected by filtration, and dried to give a beige solid. Purification of the crude product by flash chromatography (Gradient from hexanes to hexanes/EtOAc=1:1) gave the title compound as a white solid (301 mg). MS (ESI) m/z: Calculated; 296.3: Observed; 297.1. ¹H NMR (300 MHz, CDCl₃) δ ppm 10.73 (1H, br. s), 7.78 (1H, d, J=5.3 Hz), 7.08 (1H, d, J=5.3 Hz), 4.24 (2H, br. s), 3.79 (3H, s), 3.69 (3H, s)

(b) 2-(7-Hydroxy-4-methyl-5-oxo-4,5-dihydrothieno[3,2-b]pyridine-6-carboxamido)acetic acid. A suspension of methyl 2-(7-hydroxy-4-methyl-5-oxo-4,5-dihydrothieno[3,2-b]pyridine-6-carboxamido)acetate (241 mg, 813 µmol) in MeOH (2 mL) and THF (6 mL) was treated at 24° C. with 1 mL 1M aqueous NaOH and stirred for 4 hours. The mixture was acidified to pH 1 using 1M aqueous HCl, and the precipitated material was collected by filtration and dried in vacuo to give the title compound as a white solid.

Method 5

Preparation of 2-(7-hydroxy-3,4-dimethyl-5-oxo-4,5-dihydrothieno[3,2-b]pyridine-6-carboxamido)acetic Acid

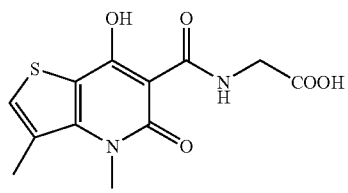

(a) tert-Butyl 2-(7-hydroxy-3,4-dimethyl-5-oxo-4,5-dihydrothieno[3,2-b]pyridine-6-carboxamido)acetate. A mixture of ethyl 7-hydroxy-3,4-dimethyl-5-oxo-4,5-dihydrothieno [3,2-b]pyridine-6-carboxylate (0.477 g, 1.78 mmol, prepared analogously to Method 3 utilizing commercially available methyl 3-amino-4-methylthiophene-2-carboxylate (Aldrich, Milwaukee, Wis.)) and tert-butyl 2-aminoacetate hydrochloride (0.598 g, 3.57 mmol) in dioxane and DIEA was stirred at 90° C. for 12 hours. The mixture was cooled to room temperature, diluted with CHCl$_3$, washed with water (1×) and brine (1×), dried over MgSO$_4$, and evaporated. Purification by flash chromatography (hexanes to hexanes/EtOAc=1:1) UV gave the title compound as a white solid (27 mg). MS (ESI) m/z: Calculated; 352.4: Observed; 353.1. $^1$H NMR (300 MHz, CDCl$_3$) δ ppm 10.73 (1H, br. s), 7.36 (1H, s), 4.12 (2H, d, J=5.4 Hz), 3.88 (3H, s), 2.62 (3H, s), 1.50 (9H, s).

(b) 2-(7-Hydroxy-3,4-dimethyl-5-oxo-4,5-dihydrothieno [3,2-b]pyridine-6-carboxamido)acetic acid. A solution of tert-butyl 2-(7-hydroxy-3,4-dimethyl-5-oxo-4,5-dihydrothieno[3,2-b]pyridine-6-carboxamido)acetate (20 mg, 57 μmol) in 1 mL TFA was stirred at 24° C. for 2 hours. The solvent was evaporated, and the residue was suspended in H$_2$O, collected by filtration and dried in vacuo to give the title compound as a white solid.

Method 6

Preparation of methyl 5-bromo-3-(methylamino)thiophene-2-carboxylate

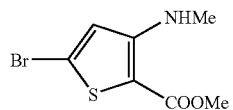

(a) Methyl 5-bromo-3-(2,2,2-trifluoroacetamido) thiophene-2-carboxylate. A mixture of methyl 3-aminothiophene-2-carboxylate (13.9 g, commercially available from Aldrich, Milwaukee, Wis.) in DCM (140 mL) and MeOH (140 mL) was treated at 24° C. with trimethylphenylammonium tribromide (100 g) followed by calcium carbonate (35.6 g). The mixture was left stirring at 24° C. for 16 hours and filtered. The cake was washed with ~100 mL EtOAc. The filtrate was concentrated under reduced pressure, and the residue was diluted with 300 mL H$_2$O and 1 L EtOAc. The layers were separated, and the organic layer was washed with H$_2$O, saturated aqueous Na$_2$S$_2$O$_3$, saturated aqueous NaHCO$_3$, and brine (each ~100 mL). The organic layer was dried (MgSO$_4$) and evaporated to give a dark oil. This material was dissolved in DCM (200 mL), cooled to 0° C., and treated with DIEA (20 mL) followed by dropwise addition of TFAA (15 mL, 106 mmol). The mixture was stirred at 0° C. to 24° C. for 3 hours and diluted with H$_2$O (~150 mL). The mixture was extracted twice with CHCl$_3$ (each ~200 mL), and the combined organic layers were dried over MgSO$_4$ and evaporated to give a brown oil. Purification by flash chromatography (hexanes to hexanes/EtOAc=9:1) resulted in light yellow solids (7.10 g). MS (ESI) m/z: Calculated; 332.1: Observed; 331.9, 333.9. $^1$H NMR (300 MHz, CDCl$_3$) δ ppm 8.75 (1H, br. s), 7.56 (1H, s), 3.91 (3H, s).

(b) Methyl 5-bromo-3-(methylamino)thiophene-2-carboxylate. A mixture of methyl 5-bromo-3-(2,2,2-trifluoroacetamido)thiophene-2-carboxylate (7.01 g, 21.1 mmol) and K$_2$CO$_3$ (5.83 g, 42.2 mmol) in DMF (50 mL) was treated with iodomethane (1.58 mL, 25.3 mmol) under Argon and heated at 65° C. for 3 hours. The mixture was cooled to room temperature, diluted with EtOAc, washed with water and brine (each 1×, 50 mL), dried (MgSO$_4$) and evaporated to give a dark oil. This residue was dissolved in MeOH (70 mL) and treated at 24° C. with NaOMe in MeOH (prepared from 0.48 g Na in 20 mL MeOH). The mixture was stirred for 15 hours, diluted with H$_2$O, and extracted with CHCl$_3$ (2×). The combined organic layers were evaporated, co-evaporated with toluene and dried in vacuo. The crude material was used in the next step without further purification.

Method 7

Preparation of Ethyl 2-bromo-7-hydroxy-3,4-dimethyl-5-oxo-4,5-dihydrothieno[3,2-b]pyridine-6-carboxylate

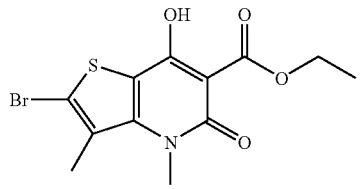

(a) Methyl 3-amino-5-bromo-4-methylthiophene-2-carboxylate. A solution of methyl 3-amino-4-methylthiophene-2-carboxylate (10.8 g, 63 mmol, commercially available from Aldrich, Milwaukee, Wis.) in AcOH (11 mL) and DCM (100 mL) was treated dropwise with a solution of Br$_2$ (6.50 mL, 126 mmol) in DCM (10 mL), stirred for 1 hour, heated to 50° C., and stirred for 18 hours. The mixture cooled to room temperature, diluted with CHCl$_3$, washed with water, dried over MgSO$_4$ and evaporated. The crude product was purified by flash chromatography using EtOAc/hexanes to give the title compound. MS (ESI) m/z: Calculated; 250.11: Observed; 249.9. $^1$H NMR (300 MHz, CDCl$_3$) δ ppm 3.81 (3H, s), 2.03 (3H, s).

(b) Methyl 5-bromo-4-methyl-3-(2,2,2-trifluoroacetamido)thiophene-2-carboxylate. At 0° C., DIEA (4.32 mL, 24.8 mmol) was added dropwise to a solution of methyl 3-amino-5-bromo-4-methylthiophene-2-carboxylate (6.20 g, 24.8 mmol) in DCM (100 mL), followed by dropwise addition of TFAA (3.45 mL, 24.8 mmol). The mixture was stirred at room temperature for 18 hours, diluted with CHCl$_3$, washed with water, dried over MgSO$_4$, and evaporated. The crude product was purified by flash chromatography using EtOAc/hexanes to give the title compound. MS (ESI) m/z: Calculated; 346.1: Observed; 345.9. $^1$H NMR (300 MHz, CDCl$_3$) δ ppm 9.62 (1H, br. s.), 3.89 (3H, s), 2.15 (3H, m).

(c) Methyl 5-bromo-4-methyl-3-(2,2,2-trifluoro-N-methylacetamido)thiophene-2-carboxylate. A suspension of methyl 5-bromo-4-methyl-3-(2,2,2-trifluoroacetamido)thiophene-2-carboxylate (0.750 g, 2.17 mmol), $K_2CO_3$ (4.33 mmol) in DMF (10 mL), was treated with iodomethane (0.162 mL, 2.60 mmol), heated to 65° C. for 1 hour, and then stirred at room temperature for 2 days. The mixture was diluted with EtOAc, washed with brine, dried over $MgSO_4$, and evaporated. The crude product was used in the next step without further purification. MS (ESI) m/z: Calculated; m/z 360.1; Observed; 361.9. $^1$H NMR (300 MHz, $CDCl_3$) δ ppm 3.86 (3H, s), 3.24 (3H, s), 2.09 (3H, s).

(d) Methyl 5-bromo-4-methyl-3-(methylamino)thiophene-2-carboxylate. Sodium methanolate (3.9 mL, 1.9 mmol) was added to a suspension of methyl 5-bromo-4-methyl-3-(2,2,2-trifluoro-N-methylacetamido)thiophene-2-carboxylate (0.70 g, 1.9 mmol) in MeOH (5 mL) and stirred for 1 hour. The solvent was removed, and the residue was dissolved in $CHCl_3$, washed with water, brine, dried over $MgSO_4$, and evaporated. The residue was purified by flash chromatography using EtOAc/hexanes to give the title compound. MS (ESI) m/z: Calculated 264.1; Observed; 265.9. $^1$H NMR (300 MHz, $CDCl_3$) δ ppm 6.85 (1H, br. s.), 3.79 (3H, s), 3.06 (3H, s), 2.28 (3H, s).

(e) Methyl 5-bromo-3-(3-ethoxy-N-methyl-3-oxopropanamido)-4-methylthiophene-2-carboxylate. A solution of methyl 5-bromo-4-methyl-3-(methylamino)thiophene-2-carboxylate (0.28 g, 1.1 mmol), DIEA (0.22 mL, 1.3 mmol), N,N-dimethylpyridin-4-amine (0.020 g, 0.16 mmol) in DMF (4 mL) was treated at room temperature with ethyl 3-chloro-3-oxopropanoate (0.16 mL, 1.3 mmol) and stirred for 18 hours. The mixture was diluted with EtOAc, washed with water, brine, dried over $MgSO_4$, and evaporated. The residue was purified by flash chromatography using EtOAc/hexanes to give the title compound. MS (ESI) m/z: Calculated 378.2; Observed; 379.0. $^1$H NMR (300 MHz, $CDCl_3$) δ ppm 4.12-4.11 (2H, m), 3.86 (3H, s), 3.16 (3H, s), 3.12 (2H, s), 2.10 (3H, s), 1.23 (3H, t, J=7.1 Hz).

(f) Ethyl 2-bromo-7-hydroxy-3,4-dimethyl-5-oxo-4,5-dihydrothieno[3,2-b]pyridine-6-carboxylate. Sodium ethanolate (0.65 mL, 0.65 mmol) was added to a solution of methyl 5-bromo-3-(3-ethoxy-N-methyl-3-oxopropanamido)-4-methylthiophene-2-carboxylate (0.12 g, 0.33 mmol) in EtOH (1 mL). During the addition, a precipitate formed. The mixture was stirred for 30 minutes, and the resulting precipitate was collected by filtration and washed with $Et_2O$ to give the title compound. MS (ESI) m/z: Calculated 346.2; Observed; 347.0. $^1$H NMR (400 MHz, DMSO-$d_6$) δ ppm 4.03-4.02 (2H, m), 3.56 (3H, br. s), 2.51 (3H, br. s), 1.20-1.18 (3H, m).

Method 8

Preparation of 2-(2-(4-fluorophenyl)-7-hydroxy-4-methyl-5-oxo-4,5-dihydrothieno[3,2-b]pyridine-6-carboxamido)acetic Acid

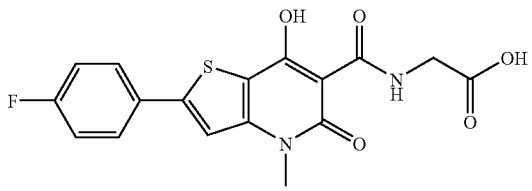

(a) tert-Butyl 2-(2-(4-fluorophenyl)-7-hydroxy-4-methyl-5-oxo-4,5-dihydrothieno[3,2-b]pyridine-6-carboxamido)acetate. A mixture of ethyl 2-(2-bromo-7-hydroxy-4-methyl-5-oxo-4,5-dihydrothieno[3,2-b]pyridine-6-carboxamido)acetate (0.20 g, 0.48 mmol, Method 7), 4-fluorophenylboronic acid (0.134 g, 0.959 mmol, commercially available from Aldrich), $Pd(Ph_3)_4$ (0.055 g, 0.048 mmol) in 1,2-dimethoxyethane (4 mL) and aqueous $Na_2CO_3$ (2M, 0.72 mL) was heated under $N_2$ at 100° C. for 2 hours. The suspension was cooled to room temperature, poured into water, extracted with $CHCl_3$, dried over $MgSO_4$ and evaporated. The residue was rinsed with $Et_2O$ and dried in vacuo to give the title compound. MS (ESI) m/z: Calculated 432.4; Observed; 431.1. $^1$H NMR (400 MHz, $CDCl_3$) δ ppm 10.72-10.672 (1H, m), 7.53 (1H, s), 7.35-7.30 (2H, m), 7.14 (2H, t, J=8.5 Hz), 4.12 (2H, d, J=5.3 Hz), 3.23 (3H, s), 1.50 (9H, s).

(b) 2-(2-(4-Fluorophenyl)-7-hydroxy-4-methyl-5-oxo-4,5-dihydrothieno[3,2-b]pyridine-6-carboxamido)acetic acid. This compound was prepared according to method 5(b). $^1$H NMR (400 MHz, $CDCl_3$) δ 12.68 (1H, br. s.), 10.28 (1H, br. s.), 7.85 (1H, s), 7.31 (2H, br. s.), 7.06-7.12 (2H, m), 3.89-3.92 (2H, m), 2.92 (3H, s).

Method 9

Preparation of 4-(2-bromo-7-hydroxy-4-methyl-5-oxo-4,5-dihydrothieno[3,2-b]pyridin-6-yl)-4-oxobutanoic Acid

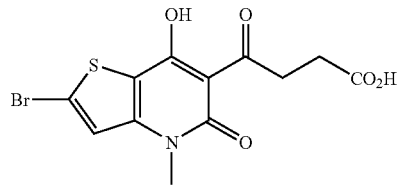

(a) 6-(3-(1,3-Dioxan-2-yl)propanoyl)-2-bromo-7-hydroxy-4-methylthieno[3,2-b]pyridin-5(4H)-one. To ethyl 2-bromo-7-hydroxy-4-methyl-5-oxo-4,5-dihydrothieno[3,2-b]pyridine-6-carboxylate (800 mg, 2408 μmol, prepared in a manner similar to that described in Method 7 using methyl 5-bromo-3-(methylamino)thiophene-2-carboxylate (Method 6(b))) was added THF (24 mL) and sodium hydride (60% in oil; 963 mg, 24084 μmol). The resulting mixture was stirred for 1 hour at ambient temperature. 2-[2-(1,3-Dioxanyl)]ethylmagnesium bromide in THF (4.81 mL, 2408 μmol) was then added dropwise at ambient temperature, and the resulting mixture was stirred for 3 hours before it was quenched with water, acidified with 5 N HCl, filtered, washed with water, and dried in a vacuum oven. The crude product was purified via HPLC to give the title compound.

(b) 4-(2-Bromo-7-hydroxy-4-methyl-5-oxo-4,5-dihydrothieno[3,2-b]pyridin-6-yl)-4-oxobutanal. To 6-(3-(1,3-dioxan-2-yl)propanoyl)-2-bromo-7-hydroxy-4-methylthieno[3,2-b]pyridin-5(4H)-one (155 mg, 385 μmol) was added 80% aqueous acetic acid (7.7 mL), and the resulting mixture was stirred for 2 hours at 100° C. The reaction product precipitated on addition of water, and was filtered and then dried in a vacuum oven to give the title compound.

(c) 4-(2-Bromo-7-hydroxy-4-methyl-5-oxo-4,5-dihydrothieno[3,2-b]pyridin-6-yl)-4-oxobutanoic acid. To 4-(2-bromo-7-hydroxy-4-methyl-5-oxo-4,5-dihydrothieno[3,2-b]pyridin-6-yl)-4-oxobutanal (215 mg, 625 μmol) was added DMF (3123 μL, 625 μmol) and Oxone (384 mg, 625 μmol). The resulting mixture was then stirred at ambient temperature for 2 hours. The reaction product precipitated on addition of water, and was filtered, washed with water, and dried in a vacuum oven to give the title compound as a light yellow solid. MS (m/z)=360, 362(M+H)$^+$. Calculated for the title compound: 360.

TABLE 1

The following table lists compounds which were prepared by the methods described above.

| Ex. | Structure | Name | $^1$H NMR (δ ppm) or MS Data | Method |
|---|---|---|---|---|
| 1 | 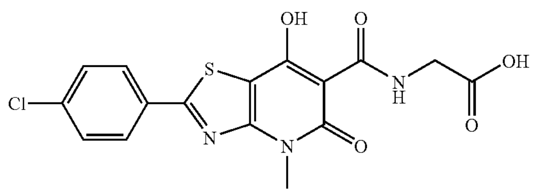 | N-((2-(4-chlorophenyl)-7-hydroxy-4-methyl-5-oxo-4,5-dihydro[1,3]thiazolo[4,5-b]pyridin-6-yl)carbonyl)glycine | 10.41-10.54 (1H, m), 8.17 (2H, d, J = 8.4 Hz), 7.68 (2H, d, J = 8.6 Hz), 4.15 (2H, d, J = 5.9 Hz), 3.78 (3H, s). | 2 |
| 2 | 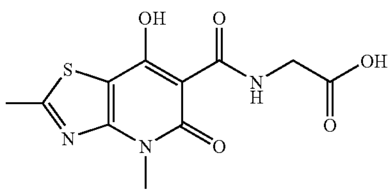 | N-((7-hydroxy-2,4-dimethyl-5-oxo-4,5-dihydro[1,3]thiazolo[4,5-b]pyridin-6-yl)carbonyl)glycine | 10.35-10.59 (1H, m), 4.11 (2H, d, J = 5.5 Hz), 3.69 (3H, s), 2.85 (3H, s). | 1 |
| 3 | 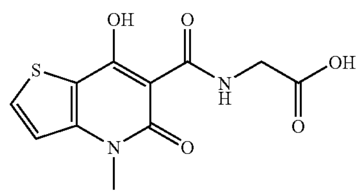 | 2-(7-hydroxy-4-methyl-5-oxo-4,5-dihydrothieno[3,2-b]pyridine-6-carboxamido)acetic acid | 12.89 (1H, s), 10.54 (1H, br. s), 8.26 (1H, d, J = 5.3 Hz), 7.47 (1H, d, J = 5.5 Hz), 4.12 (2H, br. s), 3.64 (3H, s). | 3, 4 |
| 4 | 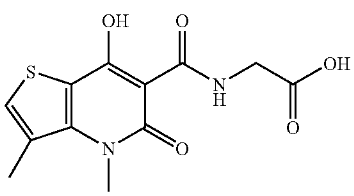 | 2-(7-hydroxy-3,4-dimethyl-5-oxo-4,5-dihydrothieno[3,2-b]pyridine-6-carboxamido)acetic acid | 10.54 (1H, s), 7.86 (1H, s), 4.12 (2H, d, J = 5.5 Hz), 3.83 (3H, s), 2.61 (3H, s). | 3, 5 |
| 5 | 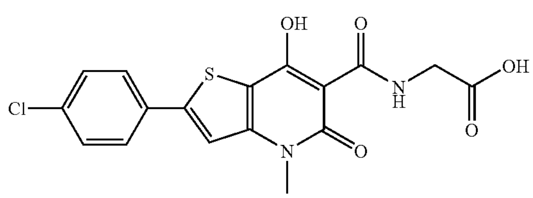 | 2-(2-(4-chlorophenyl)-7-hydroxy-4-methyl-5-oxo-4,5-dihydrothieno[3,2-b]pyridine-6-carboxamido)acetic acid | 12.90 (1H, s), 10.51 (1H, br. t, J = 5.5 Hz), 8.01 (1H, s), 7.92 (2H, d, J = 8.6 Hz), 7.60 (2H, d, J = 8.6 Hz), 4.12 (2H, d, J = 5.7 Hz), 3.68 (3H, s). | 6, 7, 4, 8 |
| 6 | 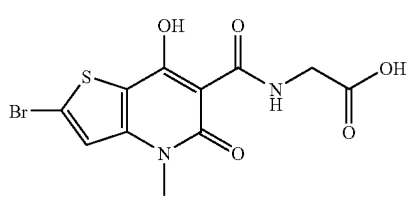 | 2-(2-bromo-7-hydroxy-4-methyl-5-oxo-4,5-dihydrothieno[3,2-b]pyridine-6-carboxamido)acetic acid | 12.93 (1H, br. s), 10.44 (1H, br. s), 8.37 (1H, s), 4.12 (2H, d, J = 5.5 Hz), 3.96 (3H, s). | 6, 7, 5 |
| 7 | 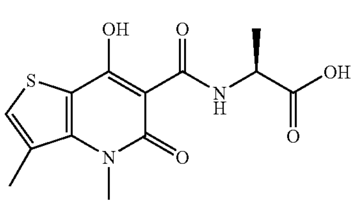 | (S)-2-(7-hydroxy-3,4-dimethyl-5-oxo-4,5-dihydrothieno[3,2-b]pyridine-6-carboxamido)propanoic acid | 13.03 (1H, br. s), 10.70 (1H, br. s), 7.86 (1H, s), 4.51-4.48 (1H, m), 3.82 (3H, s), 2.61 (3H, s), 1.44 (3H, d, J = 7.0 Hz). | 3, 5 |

TABLE 1-continued

The following table lists compounds which were prepared by the methods described above.

| Ex. | Structure | Name | $^1$H NMR (δ ppm) or MS Data | Method |
|---|---|---|---|---|
| 8 | 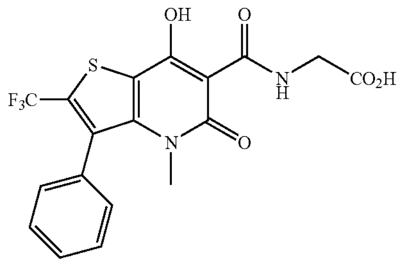 | 2-(7-hydroxy-4-methyl-5-oxo-3-phenyl-2-(trifluoromethyl)-4,5-dihydrothieno[3,2-b]pyridine-6-carboxamido)acetic acid | 12.93 (1H, br. s), 10.44 (1H, br. s), 7.55-7.53 (5H, m), 4.15 (2H, br. s), 3.38 (2H, q, J = 7.4 Hz), 2.99 (3H, s), 1.09 (3H, t, J = 7.4 Hz). Contains 0.5 equivalent Et$_2$O. | 3, 5 |
| 9 | 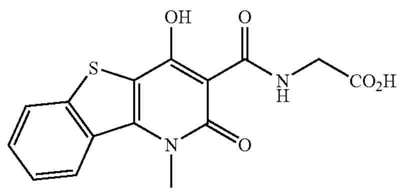 | N-((4-hydroxy-1-methyl-2-oxo-1,2-dihydro[1]benzothieno[3,2-b]pyridin-3-yl)carbonyl)glycine | 12.91 (1H, s), 10.56 (1H, br. s), 8.61 (1H, d, J = 8.3 Hz), 8.20 (1H, d, J = 8.0 Hz), 7.68 (1H, br. t, J = ca. 8.0 Hz), 7.60 (1H, br. t, J = ca. 8.0 Hz), 4.15 (2H, d, J = 5.5 Hz), 4.10 (3H, s). | 6, 7, 4, 8 |
| 10 | 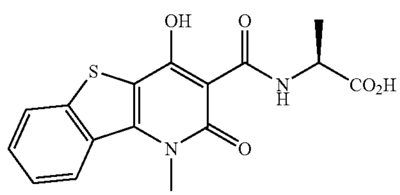 | N-((4-hydroxy-1-methyl-2-oxo-1,2-dihydro[1]benzothieno[3,2-b]pyridin-3-yl)carbonyl)-L-alanine | 13.08 (1H, br. s), 10.73 (1H, d, J = 7.0 Hz), 8.62 (1H, d, J = 8.8 Hz), 8.20 (1H, d, J = 7.8 Hz), 7.68 (br. t, 1H, J = ca. 8.0 Hz), 7.62 (1H, br. t, J = ca. 8.0 Hz), 4.56-4.53 (1H, m), 4.10 (3H, s), 1.47 (3H, d, J = 7.2 Hz). | 6, 7, 4, 8 |
| 11 | 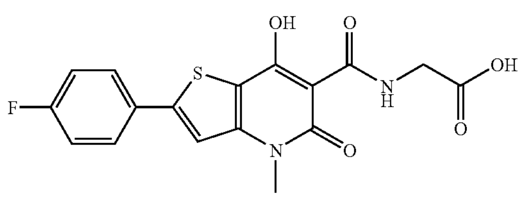 | 2-(2-(4-fluorophenyl)-7-hydroxy-4-methyl-5-oxo-4,5-dihydrothieno[3,2-b]pyridine-6-carboxamido)acetic acid | 12.68 (1H, br. s.), 10.28 (1H, br. s.), 7.85 (1H, s), 7.31 (2H, br. s.), 7.06-7.12 (2H, m), 3.89-3.92 (2H, m), 2.92 (3H, s). | 6, 7, 4, 8 |
| 12 | 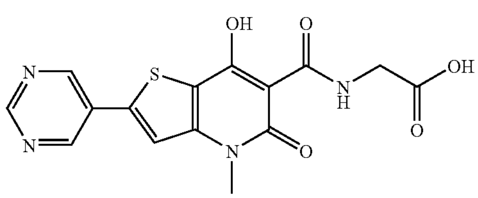 | 2-(7-hydroxy-4-methyl-5-oxo-2-(pyrimidin-5-yl)-4,5-dihydrothieno[3,2-b]pyridine-6-carboxamido)acetic acid | 12.92 (1H, br. s.), 10.49 (1H, br. s.), 9.28 (1H, s), 9.00 (2H, s), 8.28 (1H, s), 4.10-4.17 (2H, m), 3.20 (3H, s). | 6, 7, 4, 8 |
| 13 | 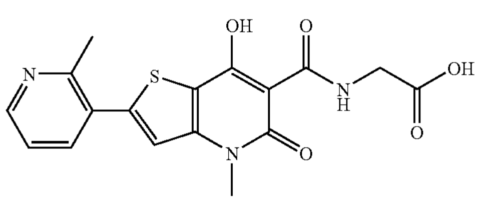 | 2-(7-hydroxy-4-methyl-2-(2-methylpyridin-3-yl)-5-oxo-4,5-dihydrothieno[3,2-b]pyridine-6-carboxamido)acetic acid | 10.46 (1H, br. s), 8.69 (1H, br. s), 8.16 (1H, br. s), 8.02 (1H, br. s), 7.56 (1H, br. s), 4.14 (2H, br. s), 3.07 (3H, br. s), 2.51 (3H, br. s). | 6, 7, 4, 8 |

TABLE 1-continued

The following table lists compounds which were prepared by the methods described above.

| Ex. | Structure | Name | ¹H NMR (δ ppm) or MS Data | Method |
|---|---|---|---|---|
| 14 | 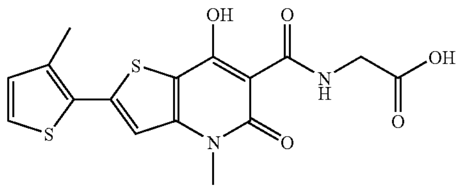 | 2-(7-hydroxy-4-methyl-2-(3-methylthiophen-2-yl)-5-oxo-4,5-dihydrothieno[3,2-b]pyridine-6-carboxamido)acetic acid | 12.92 (1H, br. s), 10.49 (1H, s), 8.22 (1H, s), 7.64-7.63 (1H, m), 7.02-7.06 (1H, m), 4.10-4.14 (2H, m), 3.22 (3H, s), 2.04 (3H, s). | 6, 7, 4, 8 |
| 15 | 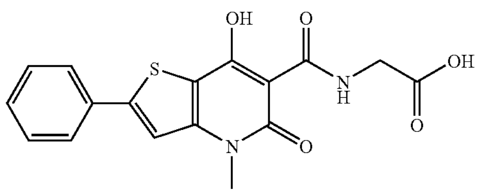 | 2-(7-hydroxy-4-methyl-5-oxo-2-phenyl-4,5-dihydrothieno[3,2-b]pyridine-6-carboxamido)acetic acid | 12.91 (1H, br. s), 10.51 (1H, br. s), 8.06 (1H, br. s), 7.49-7.47 (5H, m), 4.13 (2H, br. s), 3.14 (3H, s). | 6, 7, 4, 8 |
| 16 | 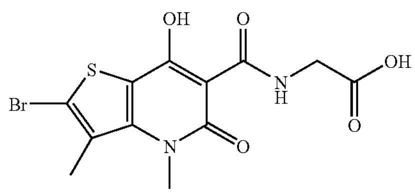 | 2-(2-bromo-7-hydroxy-3,4-dimethyl-5-oxo-4,5-dihydrothieno[3,2-b]pyridine-6-carboxamido)acetic acid | 12.90 (1H, br. s), 10.46 (1H, br. s), 4.12 (2H, br. s), 3.83 (3H, br. s), 2.60 (3H, br. s). | 6, 7, 4 |
| 17 | 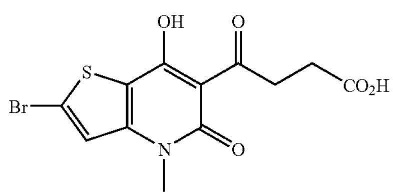 | 4-(2-bromo-7-hydroxy-4-methyl-5-oxo-4,5-dihydrothieno[3,2-b]pyridin-6-yl)-4-oxobutanoic acid | MS (m/z) = 360, 362 (M + H)⁺. | 9 |
| 18 | 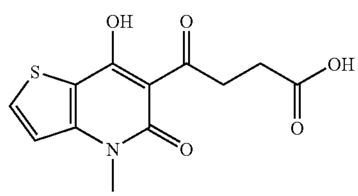 | 4-(7-hydroxy-4-methyl-5-oxo-4,5-dihydrothieno[3,2-b]pyridin-6-yl)-4-oxobutanoic acid | 7.83 (d, J = 5.48 Hz, 1H) 7.03 (d, J = 5.48 Hz, 1H) 3.65 (s, 3H) 3.61 (t, J = 6.36 Hz, 2H). MS (m/z) = 282 (M + H)⁺. | 9 |

Method 10

Preparation of 6-(((Carboxymethyl)carbamoyl)-7-hydroxy-3,4-dimethyl-5-oxo-4,5-dihydrothieno[3,2-b]pyridine-2-carboxylic Acid

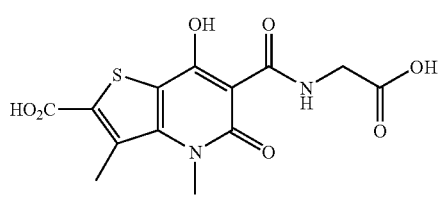

(a) 6-((2-tert-Butoxy-2-oxoethyl)carbamoyl)-7-hydroxy-3,4-dimethyl-5-oxo-4,5-dihydrothieno[3,2-b]pyridine-2-carboxylic acid. The title compound is prepared by palladium catalyzed carbonylation of tert-butyl 2-(2-bromo-7-hydroxy-3,4-dimethyl-5-oxo-4,5-dihydrothieno[3,2-b]pyridine-6-carboxamido)acetate with carbon monoxide in MeOH according to the procedure set forth in Tsuji, J. *Palladium Reagents and catalysts: Innovations in Organic Synthesis* Publisher: (Wiley, Chichester, UK), 340-5 (1995).

(b) 6-(((Carboxymethyl)carbamoyl)-7-hydroxy-3,4-dimethyl-5-oxo-4,5-dihydrothieno[3,2-b]pyridine-2-carboxylic acid. The title compound is prepared by acidic hydrolysis of 6-((2-tert-butoxy-2-oxoethyl)carbamoyl)-7-hydroxy-3,4-dimethyl-5-oxo-4,5-dihydrothieno[3,2-b]pyridine-2-carboxylic acid to remove the tert-butyl ester according to a procedure analogous to Method 5(b) followed by saponification to remove the methyl ester according to a procedure analogous to that described in Method 4(b).

TABLE 2

The following table lists compounds which are prepared by the methods described above.

| Ex. | Structure | Name | MW | Method |
|---|---|---|---|---|
| 19 | 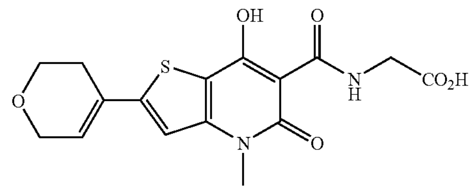 | 2-(2-(3,6-dihydro-2H-pyran-4-yl)-7-hydroxy-4-methyl-5-oxo-4,5-dihydrothieno[3,2-b]pyridine-6-carboxamido)acetic acid | 364 | 6, 7, 4, 8 |
| 20 | 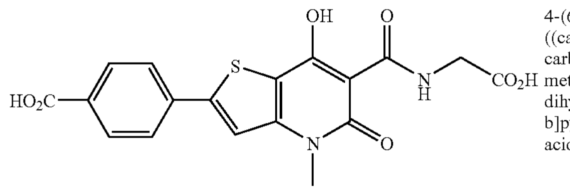 | 4-(6-((carboxymethyl)carbamoyl)-7-hydroxy-4-methyl-5-oxo-4,5-dihydrothieno[3,2-b]pyridin-2-yl)benzoic acid | 402 | 6, 7, 4, 8 |
| 21 | 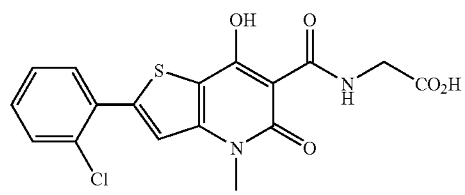 | 2-(2-(2-chlorophenyl)-7-hydroxy-4-methyl-5-oxo-4,5-dihydrothieno[3,2-b]pyridine-6-carboxamido)acetic acid | 392 | 6, 7, 4, 8 |
| 22 | 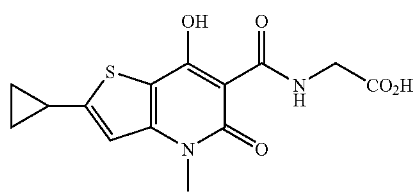 | 2-(2-cyclopropyl-7-hydroxy-4-methyl-5-oxo-4,5-dihydrothieno[3,2-b]pyridine-6-carboxamido)acetic acid | 322 | 6, 7, 4, 8 |
| 23 | 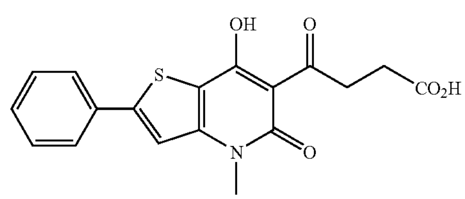 | 4-(7-hydroxy-4-methyl-5-oxo-2-phenyl-4,5-dihydrothieno[3,2-b]pyridin-6-yl)-4-oxobutanoic acid | 357 | 6, 7, 8, 9 |
| 24 | 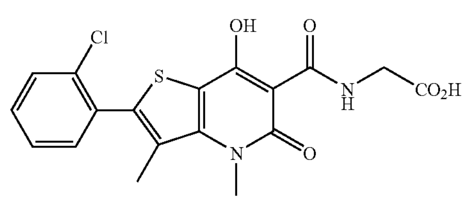 | 2-(2-(2-chlorophenyl)-7-hydroxy-3,4-dimethyl-5-oxo-4,5-dihydrothieno[3,2-b]pyridine-6-carboxamido)acetic acid | 406 | 3, 5, 6, 7, 8 |
| 25 | 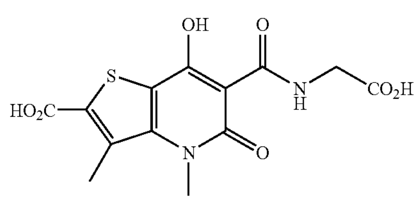 | 6-((carboxymethyl)carbamoyl)-7-hydroxy-3,4-dimethyl-5-oxo-4,5-dihydrothieno[3,2-b]pyridine-2-carboxylic acid | 340 | 6, 7, 4, 10 |

TABLE 2-continued

The following table lists compounds which are prepared by the methods described above.

| Ex. | Structure | Name | MW | Method |
|---|---|---|---|---|
| 26 | 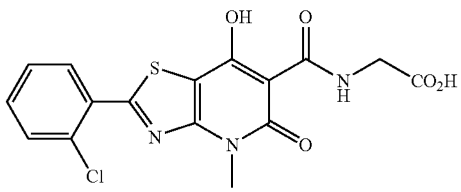 | 2-(2-(2-chlorophenyl)-7-hydroxy-4-methyl-5-oxo-4,5-dihydrothiazolo[4,5-b]pyridine-6-carboxamido)acetic acid | 393 | 2 |
| 27 | 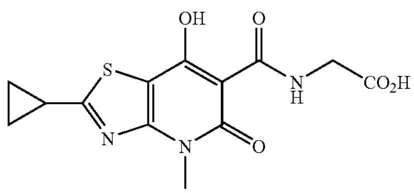 | 2-(2-cyclopropyl-7-hydroxy-4-methyl-5-oxo-4,5-dihydrothiazolo[4,5-b]pyridine-6-carboxamido)acetic acid | 323 | 2 |
| 28 | 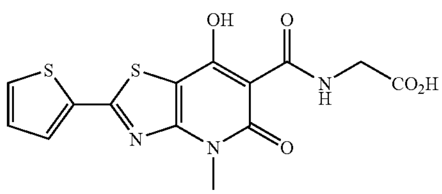 | 2-(7-hydroxy-4-methyl-5-oxo-2-(thiophen-2-yl)-4,5-dihydrothiazolo[4,5-b]pyridine-6-carboxamido)acetic acid | 365 | 2 |
| 29 | 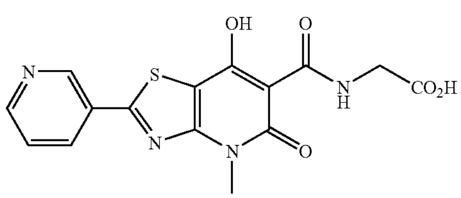 | 2-(7-hydroxy-4-methyl-5-oxo-2-(pyridin-3-yl)-4,5-dihydrothiazolo[4,5-b]pyridine-6-carboxamido)acetic acid | 360 | 2 |
| 30 | 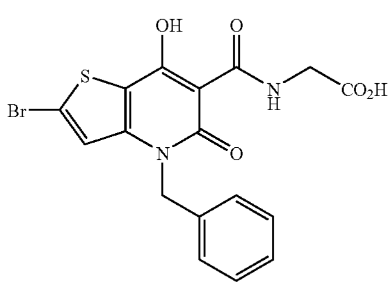 | 2-(4-benzyl-2-bromo-7-hydroxy-5-oxo-4,5-dihydrothieno[3,2-b]pyridine-6-carboxamido)acetic acid | 437 | 6, 7, 4 |
| 31 | 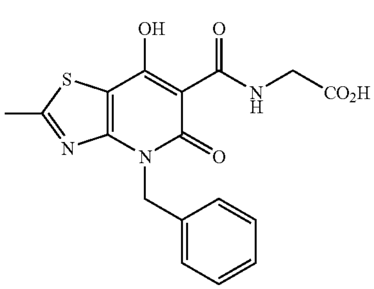 | 2-(4-benzyl-7-hydroxy-2-methyl-5-oxo-4,5-dihydrothiazolo[4,5-b]pyridine-6-carboxamido)acetic acid | 373 | 1 |

The following are examples of methods that may be used to quantitate HIF PHD activity and the inhibition of HIF PHD activity by compounds of the present invention.

Expression, Purification and Europium Labeling of VCB and Design of an Eu-VCB Based TR-FRET Assay for the Detection of Hydroxyprolyl HIF1α Peptides The VCB complex is defined as the Von Hippel-Lindau protein (pVHL), elongin B and elongin C heterotrimeric complex. VCB specifically binds to hydroxyproline residues of HIF1α, initiating polyubiquitinylation of HIF1α and its subsequent proteolytic destruction. In the absence of prolyl hydroxylase activity, VCB does not bind unmodified HIF1α. The VCB complex was expressed in *E. coli* and purified from the soluble fraction. The amino acid sequences of the three protein components are as follows:

```
VHL (Amino Acids 54-213)
                                             (SEQ ID NO: 1)
MHHHHHHEAGRPRPVLRSVNSREPSQVIFCNRSPRVVLPVWLNFDGEPQPY

PTLPPGTGRRIHSYRGHLWLFRDAGTHDGLLVNQTELFVPSLNVDGQPIFA

NITLPVYTLKERCLQVVRSLVKPENYRRLDIVRSLYEDLEDHPNVQKDLER

LTQERIAHQRMGD

ElonginB
                                             (SEQ ID NO: 2)
MDVFLMIRRHKTTIFTDAKESSTVFELKRIVEGILKRPPDEQRLYKDDQLL

DDGKTLGECGFTSQTARPQAPATVGLAFRADDTFEALCIEPFSSPPELPDV

MKPQDSGSSANEQAVQ*

ElonginC (Amino Acids 17-112)
                                             (SEQ ID NO: 5)
MYVKLISSDGHEFIVKREHALTSGTIKAMLSGPGQFAENETNEVNFREIPS

HVLSKVCMYFTYKVRYTNSSTEIPEFPIAPEIALELLMAANFLDC
```

The N-terminus of VHL contains a six histidine affinity tag for purification purposes.

A VCB-based assay allows a highly sensitive and direct measurement of enzymatic product formation (HIF1α protein or fragments thereof containing a hydroxylated proline residue) and is suitable for high throughput screening.

For expression in *E. coli*, VHL 54-213 was cloned into pAMG21 (Plux promoter) between the NdeI-XhoI site. Immediately downstream of this is the ElonginC gene cloned into the XhoI site to SacII. There is a 13 bp spacer between the stop codon of VHL and the initiating codon of ElonginC. The expression plasmid pAMG21 is a 6118 base pair plasmid that was derived from the expression vector pCFM1656 (ATCC #69576), which in turn can be derived from the expression vector system described in U.S. Pat. No. 4,710,473. This design allows for chemical rather than thermal induction of protein expression by substitution of the promoter region, replacing a synthetic bacteriophage lambda pl promoter with a DNA segment containing the LuxR gene and the LuxPR promoter, and affords regulation of expression by the plasmid-encoded LuxR protein, thereby allowing any *E. coli* strain to serve as host.

ElonginB was cloned into pTA2 (PACYC184.1 based vector) under the control of a Lac promoter. Competent *E. coli* cells were transformed with the pAMG21-VHL-ElonginC construct. These *E. coli* cells were rendered competent again prior to transformation with the pTA2-elonginB construct to produce the final *E. coli* strain containing both plasmid constructs. Induction of protein expression was initiated by the addition of IPTG and N-(3-oxo-hexanoyl)-homoserine lactone (HSL) at 30° C.

Bacterial cells were lysed by a microfluidizer in aqueous buffer of pH 8.0 and the soluble fraction was separated by centrifugation. The soluble *E. coli* fraction was subjected to Nickel-NTA chelating chromatography to utilize the six histidine affinity tag located on the pVHL construct. The pooled fractions from the nickel column were applied to a Superdex 200 size exclusion chromatography (SEC) column. The protein eluted as a monomer on SEC, indicating that the three protein components formed a complex in solution. The fractions from the SEC column were pooled and applied to a Q Sepharose anion exchange column for final purification. The purified complex was visualized by SDS-PAGE and the identities of the three protein components were confirmed by N-terminal amino acid sequencing.

Purified VCB was exchanged into 50 mM sodium carbonate buffer pH 9.2 and labeled with a europium chelate overnight. LANCE™ europium chelate (PerkinElmer, Inc; Eu-W1024 ITC chelate; catalog number is AD0013) was used to label the lysine residues of the VCB complex. The chelate contains an isothiocyanate reactive group that specifically labels proteins on lysine residues (there are fifteen lysine residues in the VCB protein complex). The resulting europylated VCB was purified by desalting columns and quantitated by standard means. The labeling yield was determined to be 6.6 europium groups per one VCB complex.

Two peptides were produced by SynPep, Inc.: a hydroxyproline modified peptide and an unmodified control peptide. VCB was expected to specifically bind to the hydroxyproline modified peptide (a mimic of enzymatic hydroxylation by prolyl hydroxylase). VCB was not expected to bind to the unmodified peptide. Both peptides were produced with a biotin group at the N-terminus to allow for binding by the streptavidin-labeled fluorescent acceptor allophycocyanin (streptavidin APC; Prozyme, Inc.).

The sequence of the custom synthesized HIF1α peptides (amino acids 556-575, with methionine residues replaced with alanine residues to prevent oxidation) were as follows:

```
                                             (SEQ ID NO: 4)
(unmodified)  Biotin-DLDLEALAPYIPADDDFQLR-CONH2

(SEQ ID NO: 5)
(modified)    Biotin-DLDLEALA[hyP]YIPADDDFQLR-CONH2
```

The peptides were purchased from SynPep as lyophilized solids and were suspended in DMSO for experimental use. The peptides were quantitated according to their absorbance at 280 nm.

Experiments were conducted in 96 well Costar polystyrene plates. Biotinylated peptides and europylated VCB were suspended in the following buffer: 100 mM HEPES 7.5, 0.1 M NaCl, 0.1% BSA and 0.05% Tween 20. The reagents were allowed to reach equilibrium by shaking for 1 hour before the plates were read on the Discovery Instrument (Packard). The data output is the ratio of the 665 nm and 620 nm emission signal resulting from the 320 nm excitation.

As shown in FIG. 1, the specific interaction of europylated VCB with the hydroxyproline modified HIF1α peptide coupled to streptavidin APC generated a fluorescence signal detectable over the background signal. These results demonstrate a fluorescence signal generated by the specific interaction of Eu-VCB with hyp-HIF1α peptide. Each bar represents the data from a single well of a 96 well assay plate. The signal to background ratio was calculated from data from a control plate (unmodified peptide). Eu-VCB concentration was titrated across rows (nM) and streptavidin APC concentrations were titrated down columns. The peptide concentration was fixed at 100 nM.

Detection of Enzymatically Converted Hydroxyprolyl HIF-1α by HIF PHD2 and Inhibition of HIF PHD2 Activity Binding of the P564-HIF1α peptide to VCB was validated utilizing the homogeneous time-resolved FRET (TR-FRET) technology. A 17 amino acid (17aa) peptide with an N-terminally labeled biotin molecule corresponding to amino acid sequences 558 to 574 of the HIF1α protein was synthesized in-house (DLEMLAPYIPMDDDFQL (SEQ ID NO: 6)). A second 17aa peptide containing a hydroxylated proline at position 564 was chemically generated to mimic the PHD enzyme converted product form of the protein that is recognized by VCB. The assay was performed in a final volume of 100 μL in buffer containing 50 mM Tris-HCl (pH 8), 100 mM NaCl, 0.05% heat inactivated FBS, 0.05% Tween-20, and 0.5% $NaN_3$. The optimal signal over background and the linear range of detection was determined by titrating the hydroxylated or unhydroxylated peptide at varied concentrations between 0 and 1 μM with a titration of VCB-Eu at varying concentrations between 0 and 50 nM with 50 nM of streptavidin APC. The binding reagents were allowed to reach equilibrium by shaking for 1 hour before it was read on the Discovery Instrument (Packard). The data output is the ratio of the 665 nm and 620 nm emission signal resulting from the 320 nm excitation.

HIF PHD2 activity was detected by P564-HIF1α peptide and VCB binding in the TR-FRET format. HIF PHD2 was assayed at various concentrations between 0 and 400 nM with 3 μM HIF1α peptide in buffer containing 50 mM Tris-HCl (pH 7.5), 100 mM NaCl, 0.05% Tween 20, 2 mM 2-oxoglutarate (2-OG), 2 mM ascorbic acid and 100 μM $FeCl_2$ in a final volume of 100 μL. The time-course was determined by periodically transferring 2.5 μL of the reaction into 250 μL of 10×TR-FRET buffer containing 500 mM HEPES (pH 7.5), 1 M NaCl, 1% BSA, and 0.5% Tween-20 to terminate the enzyme reaction. 15 nM HIF-1α peptide from the terminated reaction was added to 35 nM streptavidin-APC and 10 nM VCB-Eu to a final volume of 100 μL in 10×TR-FRET buffer. The TR-FRET reagents were placed on a shaker for 1 hour before detection on the Discovery platform.

Figure 2B:
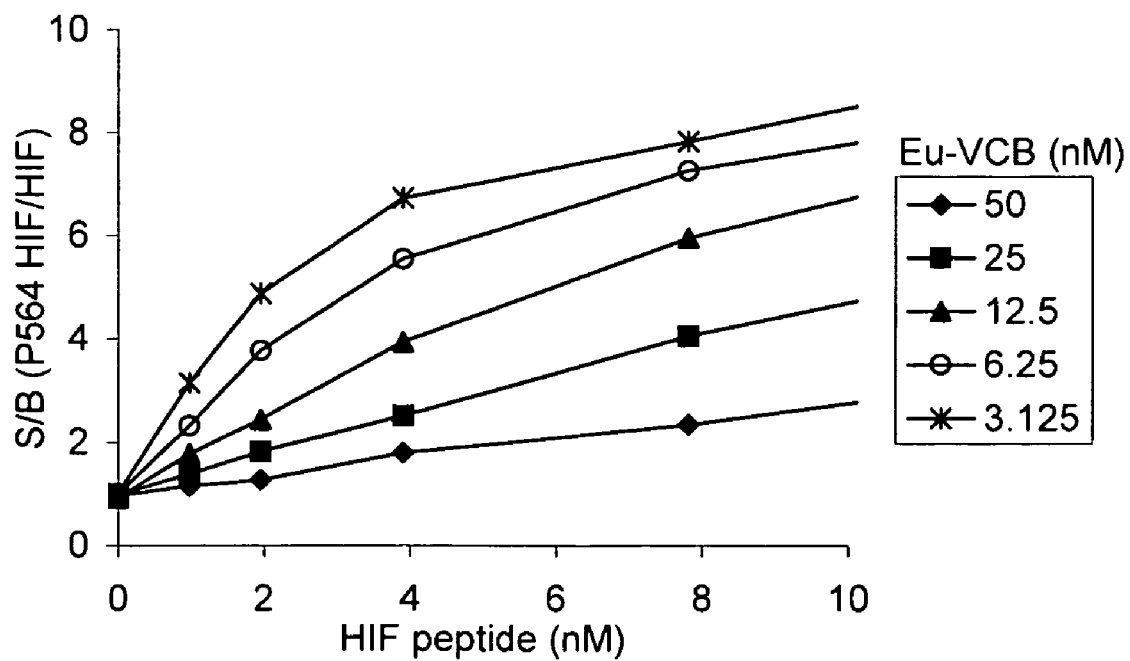

As demonstrated in FIGS. 2A and 2B, there was a dose dependent increase in TR-FRET signal resulting from binding of the hydroxylated-P564-HIF1α peptide to VCB-Eu compared to the unhydroxylated form of the peptide resulting in a 14 fold signal over noise ratio at 125 nM HIF1α peptide. VCB binding to the APC bound peptide permits a FRET transfer between the Eu and APC. The signal was linear to 2 nM peptide with 3.125 nM VCB, but increases to 62.5 nM peptide with 50 nM VCB resulting in a larger linear range.

Figure 3A:
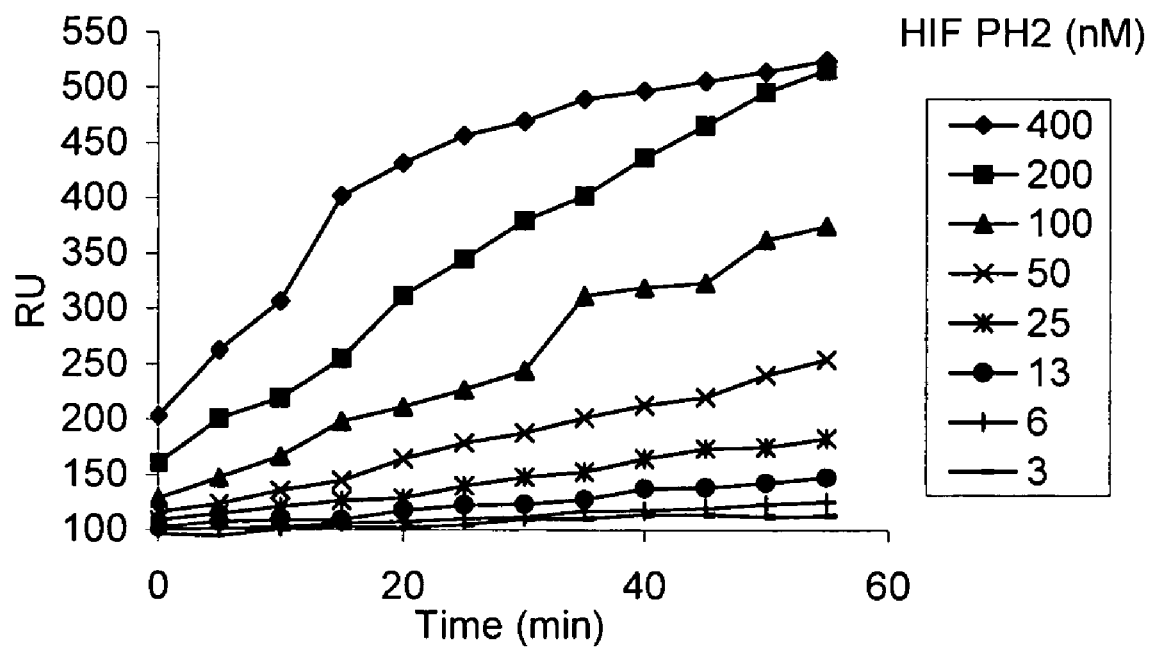
FIGS. 3A and 3B are graphs illustrating VCB binding and TR-FRET detection for determining HIF PHD2 hydroxylation of a HIF1α peptide.
Figure 3B:
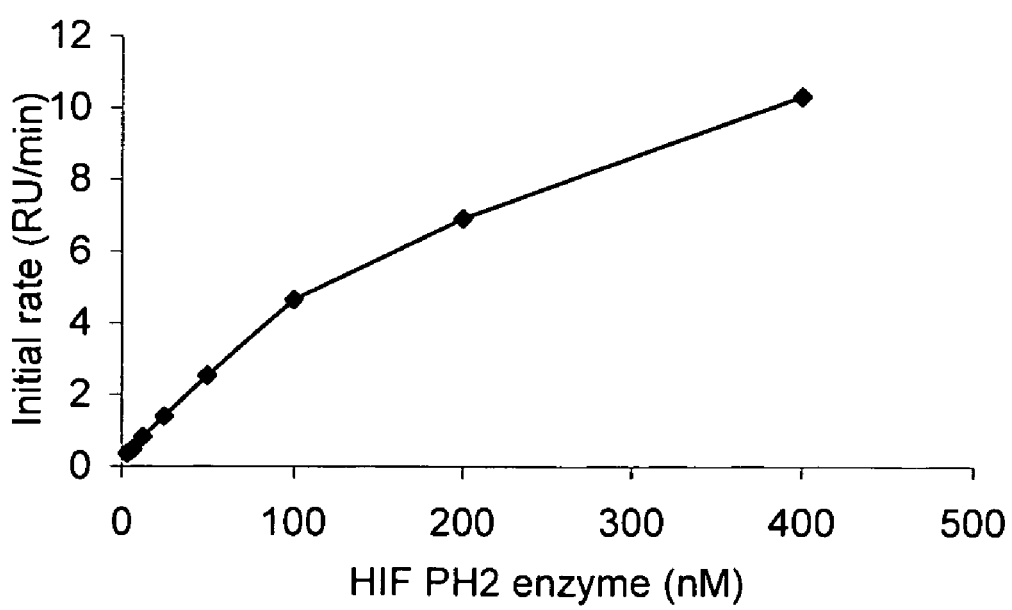

TR-FRET detection utilizing Eu-labeled VCB is a practical system for determining HIF PHD2 catalytic activity. HIF PHD2 hydroxylation of the HIF1α peptide results in the increase affinity of VCB to the peptide and hence and increased FRET signal. As shown in FIGS. 3A and 3B, activity was verified with a fairly linear and an increasing TR-FRET signal over time. There was a dose dependant increase in initial rates with increasing HIF PHD2 enzyme concentration up to 400 nM. The initial rates were linear to 100 nM enzyme.

Inhibition of HIF PHD2 activity was quantified utilizing the TR-FRET technology. HIF PHD2 catalyzes a hydroxyl modification on the proline residue of the P564-HIF1α peptide substrate (Biotin-DLEMLAPYIPMDDDFQL (SEQ ID NO: 7)) resulting in recognition and binding of the europylated Von Hippel-Lindau protein (pVHL), elongin B and elongin C heterotrimeric (VCB-Eu) complex.

The PHD2 inhibition assay was executed by addition of freshly dissolved $FeCl_2$ to 178.57 μM (100 μM final concentration) in PHD2 Reaction Buffer containing 30 mM MES, pH 6, 10 mM NaCl, 0.25% Brij-35, 0.01% BSA, and 1% DMSO. 28 μL of the iron solution and 2 μL of inhibitor compounds serially diluted in 100% DMSO (5% DMSO final) were added to black polypropylene 96-well microtiter plates. To that, 10 μL of 10 nM PHD2 (2 nM final) was added to all wells of the plate except for the 8 wells of column 12 (LO control), and allowed to incubate at room temperature on the shaker for one hour. Column 6 was the HI control containing PHD2 enzyme and 5% DMSO vehicle, but no inhibitor compound. To initiate the PHD2 enzymatic reaction, 10 μL of a solution containing 500 nM P564-HIF1α peptide (100 nM final), 10 mM ascorbic acid (2 mM final), and 1.25 μM 2-oxoglutarate (α-ketoglutarate; 0.25 μM final) in PHD2 Reaction Buffer was added to all wells of the plate and allowed to incubate on the shaker at room temperature for one hour.

The reaction was terminated by addition of 25 μL TR-FRET Buffer (50 mM TRIS-HCl, pH 9, 100 mM NaCl, 0.05% BSA, and 0.5% Tween-20) containing 150 mM succinate (product inhibitor; 50 mM final), 75 nM streptavidin-APC (25 nM final), and 7.5 nM VCB-Eu (2.5 nM final). The TR-FRET detection reagents were placed on a shaker for 1 hour to reach binding equilibrium before reading on the Discovery platform (PerkinElmer). Europium is excited at 315 nm and phosphoresces at 615 nm with a large Stoke's shift. APC, in turn, emits at 655 nm upon excitation at 615 nm. The TR-FRET signal is measured as the ratio of the APC 655 nm signal divided by the internal europium reference 615 nm emission signal.

The POC (percentage of control) was determined by comparing the signal from hydroxylated peptide substrate in the enzyme reaction containing inhibitor compound with that from PHD2 enzyme with DMSO vehicle alone (HI control), and no enzyme (LO control). POC was calculated using the formula: % control (POC)=(cpd−average LO)/(average HI−average LO)*100. Data (consisting of POC and inhibitor concentration in 1M) was fitted to a 4-parameter equation $(y=A+((B-A)/(1+((x/C)^D)))$, where A is the minimum y (POC) value, B is the maximum y (POC), C is the x (cpd concentration) at the point of inflection and D is the slope factor) using a Levenburg-Marquardt non-linear regression algorithm.

In certain embodiments, compounds of the present invention exhibit a HIF PHD inhibitory activity $IC_{50}$ value of 40 μM or less. In additional embodiments, compounds of the present invention exhibit a HIF PHD inhibitory activity $IC_{50}$ value of 10 μM or less and in further embodiments, compounds of the present invention exhibit a HIP PHD inhibitory activity $IC_{50}$ value of 5 mM or less.

The following table includes PHD2 $IC_{50}$ values obtained using the procedures set forth herein for various Examples compounds described herein.

| Table of PHD2 IC$_{50}$ values of Example Compounds | | |
|---|---|---|
| Example | Structure | PHD2 IC$_{50}$ (μM) |
| 1 | 2-(4-chlorophenyl)-7-hydroxy-4-methyl-5-oxo-4,5-dihydrothiazolo[4,5-b]pyridine-6-carboxamide glycine derivative | 0.047 |
| 2 | 7-hydroxy-2,4-dimethyl-5-oxo-4,5-dihydrothiazolo[4,5-b]pyridine-6-carboxamide glycine derivative | 0.020 |
| 3 | 7-hydroxy-4-methyl-5-oxo-4,5-dihydrothieno[3,2-b]pyridine-6-carboxamide glycine derivative | 0.075 |
| 4 | 7-hydroxy-3,4-dimethyl-5-oxo-4,5-dihydrothieno[3,2-b]pyridine-6-carboxamide glycine derivative | 0.024 |
| 5 | 2-(4-chlorophenyl)-7-hydroxy-4-methyl-5-oxo-4,5-dihydrothieno[3,2-b]pyridine-6-carboxamide glycine derivative | 0.097 |
| 6 | 2-bromo-7-hydroxy-4-methyl-5-oxo-4,5-dihydrothieno[3,2-b]pyridine-6-carboxamide glycine derivative | 0.0073 |
| 7 | 7-hydroxy-3,4-dimethyl-5-oxo-4,5-dihydrothieno[3,2-b]pyridine-6-carboxamide alanine derivative | 0.122 |

-continued

Table of PHD2 IC$_{50}$ values of Example Compounds

| Example | Structure | PHD2 IC$_{50}$ ($\mu$M) |
|---|---|---|
| 8 | 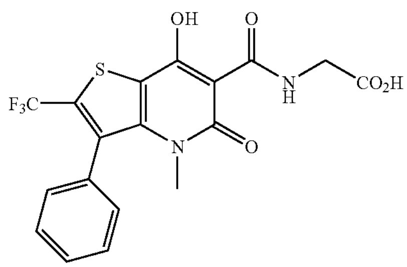 | 0.018 |
| 9 | 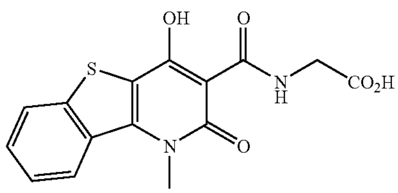 | 0.015 |
| 10 | 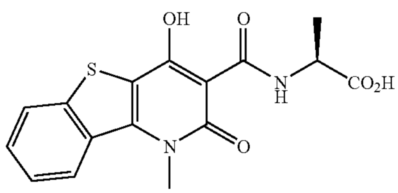 | 0.109 |
| 11 | 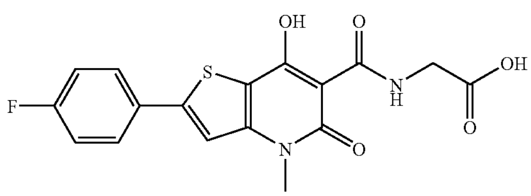 | 0.015 |
| 12 | 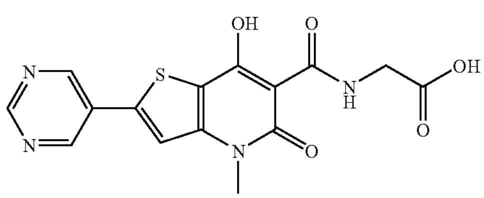 | 0.0083 |
| 13 | 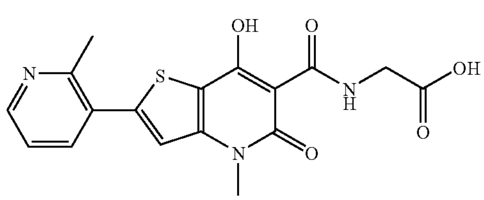 | 0.016 |
| 14 | 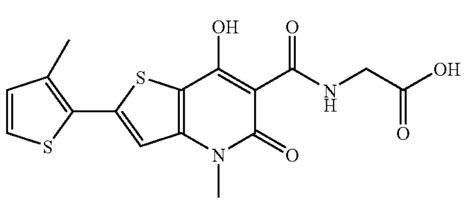 | 0.078 |

Table of PHD2 IC$_{50}$ values of Example Compounds

| Example | Structure | PHD2 IC$_{50}$ (μM) |
|---------|-----------|---------------------|
| 15 | (7-hydroxy-4-methyl-5-oxo-2-phenyl-4,5-dihydrothieno[3,2-b]pyridine-6-carbonyl)glycine | 0.021 |
| 16 | (2-bromo-7-hydroxy-3,4-dimethyl-5-oxo-4,5-dihydrothieno[3,2-b]pyridine-6-carbonyl)glycine | 0.020 |
| 17 | 4-(2-bromo-7-hydroxy-4-methyl-5-oxo-4,5-dihydrothieno[3,2-b]pyridin-6-yl)-4-oxobutanoic acid | 0.064 |
| 18 | 4-(7-hydroxy-4-methyl-5-oxo-4,5-dihydrothieno[3,2-b]pyridin-6-yl)-4-oxobutanoic acid | 0.003 |

Collagen Prolyl Hydroxylase I and II Activity Determined by Radiometric HPLC Measurement of 2-Oxoglutarate Conversion to Succinic Acid IC$_{50}$ values were obtained for the Example compounds with respect to Collagen Prolyl Hydroxylase I (CPH1) and Collagen Prolyl Hydroxylase II (CPH2) using the assay methods described below. Surprisingly, replacement of an amide N in the side chain of the molecule with a C atom greatly enhanced the selectivity of the Example compounds for PHD2 with respect to CPH1 and CPH2.

Assay conditions were established in separate studies to define dependence on dithiothreitol (DTT), ascorbate, and catalase, and to define reaction linearity and K$_m$ values for 2-oxoglutarate (2-OG; PerkinElmer LAS, Shelton, Conn. or Moravek Biochemicals, Brea, Calif.), FeSO$_4$, and (Pro-Pro-Gly)$_{10}$ peptide (PPG$_{10}$; Peptides International, Louisville, Ky.). Linearity was evident to at least 40% conversion but reactions did not typically exceed 30% conversion of 2-OG to succinic acid (SA). Product inhibition was not evident. Compounds were dissolved and serially diluted in 100% DMSO for potency determination. Assay Buffer consisted of Tris-HCl, pH 7.5, 0.2 mM DTT, and 0.5 mg/ml catalase. PPG$_{10}$ peptide was dissolved in 0.25% acetic acid and denatured by boiling for 5 minutes then placed on ice for 5 minutes. The denatured PPG$_{10}$ was then pre-mixed with 1 M ascorbate, prepared in water, and the mixture diluted with Assay Buffer to yield a working solution of 5× peptide and ascorbate. FeSO$_4$ was freshly dissolved in water and diluted to a 2.8× concentration in Assay Buffer. Enzyme stocks were diluted to a 5× concentration in Assay Buffer. Example compounds plus FeSO$_4$ solution were mixed, followed by addition of 5× enzyme solutions. After 10 minutes gentle mixing at room temperature, the 5× peptide solution was added. After another 10 minutes gentle mixing at room temperature, a 5× stock of 2-OG was added to initiate the reaction. Final concentrations in the assay were: 50 mM Tris-HCl, pH 7.5, 0.2 mM DTT, 0.5 mg/mL catalase, 10 μM FeSO$_4$, 100 μM PPG$_{10}$, 50 μM 5-[$^{14}$C]-2-oxoglutarate (23-37 cpm/pmol), 1 mM ascorbate, and 4% DMSO. Reactions were gently mixed at room temperature for 1 hour and terminated by addition of an equal volume of 0.02 N $H_2SO_4$. Unless otherwise indicated, all reagents were obtained from Sigma and were the highest grade available.

A portion of each terminated reaction was auto-injected into a Polypore H column (PerkinElmer, Waltham, Mass.) at a rate of 0.3 mL/min with 0.01 $NH_2SO_4$ as the mobile phase. The HPLC method employed exploits the difference in pKa of the 2-OG and SA carboxylates to chromatographically separate substrate from product at low pH on ion-exchange resin, as described by Cunliffe, et al (Biochem J., 240, 617-619 (1986)) and Kaule and Gunzler (Anal. Biochem., 184, 291-297 (1990)). An Agilent 1100 HPLC System with dual quaternary pumps, column switching valve, and dual columns was used to resolve product from substrate. The Agilent 1100 Multiple Wavelength Detector indicated UV absorption of the substrate and product peaks at 210 nm and a Beta-RAM Model 2 radiation detector with In-Flow 2:1 scintillation cocktail (IN/US Systems Inc.) enabled quantitation of the 2 radioactive peaks. Laura Lite software (IN/US, Tampa, Fla.) was used to collect and analyze radiometric data. AUC measurements were converted to percent turnover of 2-OG. To standardize across studies, 2-OG conversion was normalized to percent of control (POC) values using reactions that lacked enzyme or inhibitor as low and high controls, respectively. POC data was fitted to the 4-parameter logistic model (A+((B−A)/(1+((x/C)^D)))) using ActivityBase (IDBS, Alameda Calif.) where A is the minimum POC value, B is the maximum POC value, D is the slope factor, and C is compound concentration at the inflection point ($IC_{50}$, micromolar).

Cloning and Expression of CPH1 and CPH2 Enzymes

The Baculovirus Expression Vector System (BEVS) from Invitrogen was used to express collagen prolyl 4-hydroxylase (CPH) in *Trichoplusia ni* insect cells. Active collagen prolyl 4-hydroxylase is an oligomeric protein that exists as an $\alpha_2\beta_2$ tetramer. The alpha subunits incorporated into the tetramer can be either collagen prolyl 4-hydroxylase α1 (GenBank reference sequence NM_000917) or collagen prolyl 4-hydroxylase α2 (GenBank reference sequence NM_004199). The beta subunit, collagen prolyl 4-hydroxylase 0 (GenBank reference sequence NM_000918), is common to both forms of the tetramer. The genes encoding the three subunits, α1, α2 and β, were cloned individually into separate pFastBac1 shuttle vectors (Invitrogen) in their precursor forms, which include the native human secretion signal sequences. For the purpose of identifying expressed protein, the α subunit genes included a caspase-3 cleavable six-histidine metal affinity sequence at the 5' end of the gene. In the expressed protein, the metal affinity tag (MAHHHHHHDEVD) (SEQ ID NO: 8) was positioned at the α subunit N-terminus upstream of the secretion signal sequence. For the purpose of identification and purification, the β subunit gene was designed to encode a six-histidine metal affinity tag positioned downstream of the secretion signal peptide so that the metal affinity tag would remain after cleavage and secretion into the endoplasmic reticulum. These recombinant pFastBac1 shuttle vectors were each used to generate baculovirus capable of expressing their respective subunit polypeptides. The active, tetrameric form of the enzyme was generated by co-expressing either CPH-α1 and CPH-β or CPH-α2 and CPH-β baculovirus at 27° C. Cells were harvested 48 hours post-infection by centrifugation.

Protein Sequences

The sequences before the slash symbol (/) were removed in vivo upon secretion into the endoplasmic reticulum. In the following paragraphs, SS stands for secretion signal sequence.

CPH-α1 (MAH$_6$DEVD)-SS-CPHα1)
(SEQ ID NO: 9)
MAHHHHHHDEVDIWYILIIGILLPQSLA/HPGFFTSIGQMTDLIHTEKDLV

TSLKDYIKAEEDKLEQIKKWAEKLDRLTSTATKDPEGFVGHPVNAFKLMKR

LNTEWSELENLVLKDMSDGFISNLTIQRQYFPNDEDQVGAAKALLRLQDTY

NLDTDTISKGNLPGVKHKSFLTAEDCFELGKVAYTEADYYHTELWMEQALR

QLDEGEISTIDKVSVLDYLSYAVYQQGDLDKALLLTKKLLELDPEHQRANG

NLKYFEYIMAKEKDVNKSASDDQSDQKTTPKKKGVAVDYLPERQKYEMLCR

GEGIKMTPRRQKKLFCRYHDGNRNPKFILAPAKQEDEWDKPRIIRFHDIIS

DAEIEIVKDLAKPRLSRATVHDPETGKLTTAQYRVSKSAWLSGYENPVVSR

INMRIQDLTGLDVSTAEELQVANYGVGGQYEPHFDFARKDEPDAFKELGTG

NRIATWLFYMSDVSAGGATVFPEVGASVWPKKGTAVFWYNLFASGEGDYST

RHAACPVLVGNKWVSNKWLHERGQEFRRPCTLSELE

CPH-a2 (MAH6DEVD-SS-CPHa2)
(SEQ ID NO: 10)
MAHHHHHHDEVDKLWVSALLMAWFGVLSCVQA/EFFTSIGHMTDLIYAEKE

LVQSLKEYILVEEAKLSKIKSWANKMEALTSKSAADAEGYLAHPVNAYKLV

KRLNTDWPALEDLVLQDSAAGFIANLSVQRQFFPTDEDEIGAAKALMRLQD

TYRLDPGTISRGELPGTKYQAMLSVDDCFGMGRSAYNEGDYYHTVLWMEQV

LKQLDAGEEATTTKSQVLDYLSYAVFQLGDLHRALELTRRLLSLDPSHERA

GGNLRYFEQLLEEEREKTLTNQTEAELATPEGIYERPVDYLPERDVYESLC

RGEGVKLTPRRQKRLFCRYHHGNRAPQLLIAPFKEEDEWDSPHIVRYYDVM

SDEEIERIKEIAKPKLARATVRDPKTGVLTVASYRVSKSSWLEEDDDPVVA

RVNRRMQHITGLTVKTAELLQVANYGVGGQYEPHFDFSRRPFDSGLKTEGN

RLATFLNYMSDVEAGGATVFPDLGAAIWPKKGTAVFWYNLLRSGEGDYRTR

HAACPVLVGCKWVSNKWFHERGQEFLRPCGSTEVD

CPHβ (SS-H$_6$-CPHβ)
(SEQ ID NO: 11)
MLRRALLCLAVAALVRA/HHHHHHDAPEEEDHVLVLRKSNFAEALAAHKYL

LVEFYAPWCGHCKALAPEYAKAAGKLKAEGSEIRLAKVDATEESDLAQQYG

VRGYPTIKFFRNGDTASPKEYTAGREADDIVNWLKKRTGPAATTLPDGAAA

ESLVESSEVAVIGFFKDVESDSAKQFLQAAEAIDDIPFGITSNSDVFSKYQ

LDKDGVVLFKKFDEGRNNFEGEVTKENLLDFIKHNQLPLVIEFTEQTAPKI

FGGEIKTHILLFLPKSVSDYDGKLSNFKTAAESFKGKILFIFIDSDHTDNQ

RILEFFGLKKEECPAVRLITLEEEMTKYKPESEELTAERITEFCHRFLEGK

```
IKPHLMSQELPEDWDKQPVKVLVGKNFEDVAFDEKKNVFVEFYAPWCGHCK

QLAPIWDKLGETYKDHENIVIAKMDSTANEVEAVKVHSFPTLKFFPASADR

TVIDYNGERTLDGFKKFLESGGQDGAGDDDDLEDLEEAEEPDMEEDDDQKA

VKDEL
```

Purification and Characterization of CPH Enzymes

T.ni cells were resuspended in 25 mM Tris (pH 7.8), 0.15M NaCl, 10% glycerol, 0.1% Triton X-100, and Complete "Free" protease inhibitor cocktail (Roche) and were lysed by a microfluidizer. Lysate was cleared by centrifugation and filtered through a 0.45 μm cellulose acetate membrane before application to a Ni-NTA column at 2 mL/min. The column was washed with 25 mM imidazole and protein was eluted with a buffer containing; 20 mM Tris 7.8, 0.15 M NaCl, 10% glycerol, 0.1% CHAPS and 250 mM imidazole. Peak fractions were pooled and applied to a Superdex 200 XK 26/60 column (GE Biosciences) equilibrated with; 20 mM Tris (pH 7.8), 0.15M NaCl, 10% glycerol and 0.1% CHAPS. Protein identity was confirmed by Edman sequencing and α2β2 heterodimer formation was detected by light scattering. Protein concentration was determined according to the calculated molar extinction coefficient at 280 nm, and enzyme was typically snap frozen in liquid nitrogen and stored at −80° C.

The following table includes PHD2, CPH1, and CPH2 $IC_{50}$ values obtained using the procedures set forth herein for four of the Example compounds described herein. As shown in the following table, replacement of the N atom with a C atom in the side chain results in a significant and surprising increase in selectivity of a compound for PHD2 with respect to both CPH1 and CPH2 in the compounds of the invention while retaining significant PHD2 activity. For example, the PHD2/CPH1 selectivity with respect to Example 6 increases from 9.6:1 to greater than 625:1 and the PHD2/CPH2 selectivity increases from 4.1:1 to 59.1:1 by replacing the amide N atom with a C atom to produce Example 17. For example, the PHD2/CPH1 selectivity with respect to Example 3 increases from 13.2:1 to greater than 13, 333:1 and the PHD2/CPH2 selectivity increases from 4.6:1 to 11, 433:1 by replacing the amide N atom with a C atom to produce Example 18. Therefore, in some embodiments, the invention provides a compound of any of the embodiments where X is —($CR_bR_c$)— in which the selectivity of the compound for PHD2 with respect to CPH1 is greater than 5, greater than 8, greater than 10, greater than 15, greater than 20, greater than 100, greater than 500, or is even higher. The selectivity for these purposes, can be determined by dividing the CPH1 $IC_{50}$ value of the compound by the PHD2 $IC_{50}$ value of the compound where the $IC_{50}$ values are determined using the methods presented herein.

Table of PHD2, CPH1 and CPH2 $IC_{50}$ values of Example and Comparative Compounds

| Structure | Compound | PHD2 $IC_{50}$ (μM) | CPH1 $IC_{50}$ (μM) | CPH2 $IC_{50}$ (μM) |
|---|---|---|---|---|
| 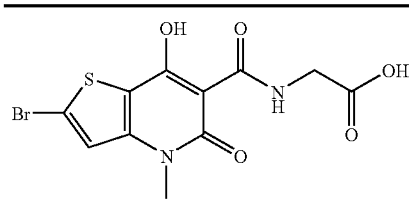 | Example 6 | 0.0073 | 0.070 | 0.030 |
| 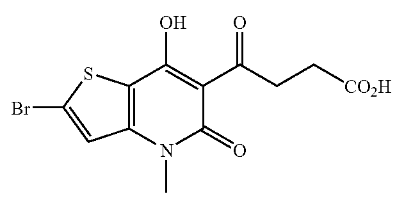 | Example 17 | 0.064 | >40 | 3.78 |
| 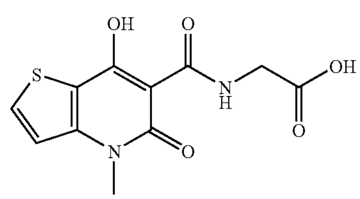 | Example 3 | 0.075 | 0.992 | 0.345 |
| 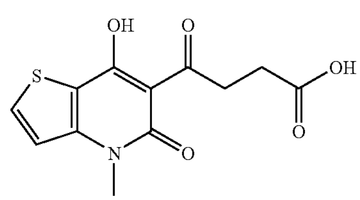 | Example 18 | 0.003 | >40 | 34.3 |

All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A composition of matter, comprising at least one compound of Formula I:

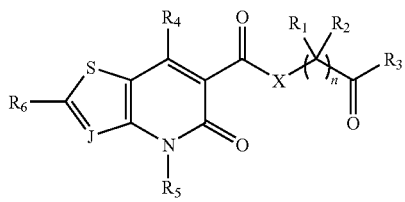

a pharmaceutically acceptable salt thereof, a tautomer thereof, or a pharmaceutically acceptable salt of the tautomer; or a solvate thereof, a chelate thereof, a non-covalent complex thereof, a prodrug thereof, or a mixture of any of the foregoing, wherein:

J is selected from $CR_7$ or N;

n is 1 to 6;

$R_1$ and $R_2$ are independently selected in each instance from H, lower alkyl, substituted lower alkyl, lower haloalkyl, or substituted lower haloalkyl, or $R_1$ and $R_2$ can join together to form a 3 to 6 membered ring or a substituted 3 to 6 membered ring;

X is —$(CR_bR_c)$—, wherein $R_b$ and $R_c$ are independently selected from H, lower alkyl, substituted lower alkyl, lower haloalkyl, or substituted lower haloalkyl, or $R_b$ and $R_c$ can join together to form a 3 to 6 membered ring or a substituted 3 to 6 membered ring;

$R_3$ is selected from OH, SH, $NH_2$, lower alkyl, substituted lower alkyl, lower alkoxy, substituted lower alkoxy, or sulfanyl;

$R_4$ is selected from H, OH, lower alkoxy, SH, $NH_2$, $NHSO_2R_8$, or sulfonyl;

$R_5$ is selected from H, lower alkyl, or substituted lower alkyl;

$R_6$ and $R_7$ are independently selected from H, F, Cl, Br, I, alkyl, substituted alkyl, haloalkyl, perhaloalkyl, alkenyl, substituted alkenyl, alkynyl, substituted alkynyl, $NR_dR_e$, $C(O)R_8$, $C(O)OR_9$, $OR_9$, $SR_9$, $SO_2R_9$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, or —Y—$R_{10}$; or, $R_6$ and $R_7$ may join to form an optionally substituted 5 or 6 membered ring when J is $CR_7$, wherein:

Y is selected from —$N(R_{11})$—Z— or —Z—$N(R_{11})$—;

Z is selected from C(O), $SO_2$, alkylene, substituted alkylene, alkenylene, substituted alkenylene, alkynylene, or substituted alkynylene;

$R_8$ is selected from H, alkyl, substituted alkyl, alkenyl, substituted alkenyl, alkynyl, substituted alkynyl heterocyclyl, substituted heterocyclyl, aryl, substituted aryl, heteroaryl, or substituted heteroaryl;

$R_9$ is selected from H, alkyl, substituted alkyl, alkenyl, substituted alkenyl, alkynyl, or substituted alkynyl;

$R_{10}$ is selected from H, heterocyclyl, substituted heterocyclyl, aryl, substituted aryl, heteroaryl, or substituted heteroaryl;

$R_{11}$ is selected from H, lower alkyl, or substituted lower alkyl; and $R_d$ and $R_e$ are independently selected from H, lower alkyl, substituted lower alkyl, lower haloalkyl, or substituted lower haloalkyl, or $R_d$ and $R_e$ can join together to form a 3 to 6 membered ring or a substituted 3 to 6 membered ring.

2. The composition of matter according to claim 1, wherein J is $CR_7$.

3. The composition of matter according to claim 1, wherein J is N.

4. The composition of matter according to claim 1, wherein $R_3$ is OH.

5. The composition of matter according to claim 1, wherein $R_4$ is OH.

6. The composition of matter according to claim 1, wherein $R_b$ and $R_c$ are both H.

7. The composition of matter according to claim 1, wherein at least one of $R_6$ or $R_7$ is a substituted or unsubstituted aryl, a substituted or unsubstituted heteroaryl, a substituted or unsubstituted cycloalkyl, or a substituted or unsubstituted heterocyclyl group.

8. The composition of matter according to claim 7, wherein at least one of $R_6$ or $R_7$ is a heterocyclyl group.

9. The composition of matter according to claim 7, wherein at least one of $R_6$ or $R_7$ is a heteroaryl group.

10. The composition of matter according to claim 7, wherein at least one of $R_6$ or $R_7$ is a phenyl or substituted phenyl group.

11. The composition of matter according to claim 1, wherein at least one of $R_6$ or $R_7$ is chosen from a halo or a moiety substituted with at least one halo.

12. The composition of matter according to claim 1, wherein n is 1.

13. The composition of matter according to claim 1, wherein $R_1$ and $R_2$ are independently chosen from H and lower alkyl.

14. The composition of matter according to claim 13, wherein $R_1$ and $R_2$ are independently chosen from H and methyl.

15. The composition of matter according to claim 13, wherein $R_1$ and $R_2$ are both H.

16. The composition of matter according to claim 1, wherein J is $CR_7$, n is 1; $R_1$ is H or lower alkyl; $R_2$ is H; $R_3$ is OH; $R_4$ is OH; and $R_b$ and $R_c$ are both H.

17. The composition of matter according to claim 1, wherein J is N, n is 1; $R_1$ is H or lower alkyl; $R_2$ is H; $R_3$ is OH; $R_4$ is OH; and $R_b$ and $R_c$ are both H.

18. The composition of matter according to claim 1, wherein $R_5$ is H.

19. The composition of matter according to claim 1, wherein $R_5$ is lower alkyl.

20. The composition of matter according to claim 1, wherein $R_5$ is methyl.

21. The composition of matter according to claim 1, wherein $R_5$ is a substituted lower alkyl selected from an arylalkyl, a heteroarylalkyl, a heterocyclylalkyl, a cycloalkylalkyl, a hydroxyalkyl, an alkoxyalkyl, or a haloalkyl.

22. The composition of matter according to claim 1, wherein J is $CR_7$ and $R_6$ and $R_7$, together with the carbon atoms to which they are attached, join to form a 6-membered carbocyclic aromatic ring that may be optionally substituted with up to three substituents.

23. The composition of matter according to claim 1, wherein the compound is 4-(2-bromo-7-hydroxy-4-methyl-5-oxo-4,5-dihydrothieno[3,2-b]pyridin-6-yl)-4-oxobutanoic acid or is a salt thereof, a tautomer thereof, or a salt of the tautomer.

24. The composition of matter according to claim 1, wherein the compound is 4-(7-hydroxy-4-methyl-5-oxo-2-phenyl-4,5-dihydrothieno[3,2-b]pyridin-6-yl)-4-oxobutanoic acid or is a salt thereof, a tautomer thereof, or a salt of the tautomer.

25. A pharmaceutical formulation, comprising a therapeutically effective amount of the composition of matter according to claim 1 and at least one pharmaceutically acceptable excipient.

26. The pharmaceutical formulation of claim 25, wherein the composition of matter is present in an amount effective for the treatment of at least one disease selected from ischemia, anemia, wound healing, auto-transplantation, allo-transplantation, xeno-transplantation, systemic high blood pressure, thalassemia, diabetes, cancer, or an inflammatory disorder.

27. A composition of matter, comprising at least one compound of Formula I:

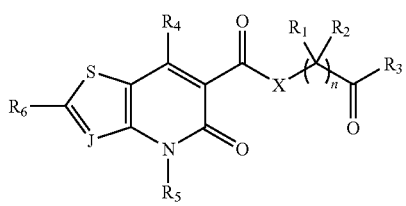

a pharmaceutically acceptable salt thereof, a tautomer thereof, or a pharmaceutically acceptable salt of the tautomer; or a solvate thereof, a chelate thereof, a non-covalent complex thereof, a prodrug thereof, or a mixture of any of the foregoing, wherein:

J is selected from $CR_7$ or N;

n is 1 to 6;

$R_1$ and $R_2$ are independently selected in each instance from H, lower alkyl, substituted lower alkyl, lower haloalkyl, or substituted lower haloalkyl, or $R_1$ and $R_2$ can join together to form a 3 to 6 membered ring or a substituted 3 to 6 membered ring;

X is selected from —$NR_a$—, —O—, —S—, or —($CR_bR_c$)—, wherein $R_a$ is selected from H or lower alkyl, and $R_b$ and $R_c$ are independently selected from H, lower alkyl, substituted lower alkyl, lower haloalkyl, or substituted lower haloalkyl, or $R_b$ and $R_c$ can join together to form a 3 to 6 membered ring or a substituted 3 to 6 membered ring;

$R_3$ is selected from OH, SH, $NH_2$, lower alkyl, substituted lower alkyl, lower alkoxy, substituted lower alkoxy, or sulfanyl;

$R_4$ is selected from H, OH, lower alkoxy, SH, $NH_2$, $NHSO_2R_8$, or sulfonyl;

$R_5$ is selected from H, lower alkyl, or substituted lower alkyl;

$R_6$ and $R_7$ are independently selected from H, F, Cl, Br, I, alkyl, substituted alkyl, haloalkyl, perhaloalkyl, alkenyl, substituted alkenyl, alkynyl, substituted alkynyl, $NR_dR_e$, $C(O)R_8$, $C(O)OR_9$, $OR_9$, $SR_9$, $SO_2R_9$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, or —Y—$R_{10}$; or, $R_6$ and $R_7$ may join to form an optionally substituted 5 or 6 membered ring when J is $CR_7$, wherein:

Y is selected from —N($R_{11}$)—Z— or —Z—N($R_{11}$)—;

Z is selected from C(O), $SO_2$, alkylene, substituted alkylene, alkenylene, substituted alkenylene, alkynylene, or substituted alkynylene;

$R_8$ is selected from H, alkyl, substituted alkyl, alkenyl, substituted alkenyl, alkynyl, substituted alkynyl heterocyclyl, substituted heterocyclyl, aryl, substituted aryl, heteroaryl, or substituted heteroaryl;

$R_9$ is selected from H, alkyl, substituted alkyl, alkenyl, substituted alkenyl, alkynyl, or substituted alkynyl;

$R_{10}$ is selected from H, heterocyclyl, substituted heterocyclyl, aryl, substituted aryl, heteroaryl, or substituted heteroaryl;

$R_{11}$ is selected from H, lower alkyl, or substituted lower alkyl; and $R_d$ and $R_e$ are independently selected from H, lower alkyl, substituted lower alkyl, lower haloalkyl, or substituted lower haloalkyl, or $R_d$ and $R_e$ can join together to form a 3 to 6 membered ring or a substituted 3 to 6 membered ring, wherein $R_1$ and $R_2$ are not both H if X is —$NR_a$—; $R_a$ is H; and n is 1.

28. The composition of matter according to claim 27, wherein J is $CR_7$.

29. The composition of matter according to claim 27, wherein J is N.

30. The composition of matter according to claim 27, wherein $R_3$ is OH.

31. The composition of matter according to claim 27, wherein $R_4$ is OH.

32. The composition of matter according to claim 27, wherein X is —$NR_a$—.

33. The composition of matter according to claim 27, wherein X is —NH—.

34. The composition of matter according to claim 27, wherein at least one of $R_6$ or $R_7$ is a substituted or unsubstituted aryl, a substituted or unsubstituted heteroaryl, a substituted or unsubstituted cycloalkyl, or a substituted or unsubstituted heterocyclyl group.

35. The composition of matter according to claim 34, wherein at least one of $R_6$ or $R_7$ is a heterocyclyl group.

36. The composition of matter according to claim 34, wherein at least one of $R_6$ or $R_7$ is a heteroaryl group.

37. The composition of matter according to claim 34, wherein at least one of $R_6$ or $R_7$ is a phenyl or substituted phenyl group.

38. The composition of matter according to claim 27, wherein at least one of $R_6$ or $R_7$ is chosen from a halo or a moiety substituted with at least one halo.

39. The composition of matter according to claim 27, wherein n is 1.

40. The composition of matter according to claim 27, wherein $R_1$ and $R_2$ are independently chosen from H and lower alkyl.

41. The composition of matter according to claim 40, wherein $R_1$ and $R_2$ are independently chosen from H and methyl.

42. The composition of matter according to claim 40, wherein $R_1$ and $R_2$ are both H.

43. The composition of matter according to claim 27, wherein J is $CR_7$, n is 1; $R_1$ is H or lower alkyl; $R_2$ is H; $R_3$ is OH; $R_4$ is OH; X is —$NR_a$— wherein $R_a$ is H, or X is —($CR_bR_c$)— wherein $R_b$ and $R_c$ are both H.

44. The composition of matter according to claim 27, wherein J is N, n is 1; $R_1$ is H or lower alkyl; $R_2$ is H; $R_3$ is OH; $R_4$ is OH; X is —$NR_a$— wherein $R_a$ is H, or X is —($CR_b R_c$)— wherein $R_b$ and $R_c$ are both H.

45. The composition of matter according to claim 27, wherein $R_5$ is H.

46. The composition of matter according to claim 27, wherein $R_5$ is lower alkyl.

47. The composition of matter according to claim 27, wherein $R_5$ is methyl.

48. The composition of matter according to claim 27, wherein $R_5$ is a substituted lower alkyl selected from an arylalkyl, a heteroarylalkyl, a heterocyclylalkyl, a cycloalkylalkyl, a hydroxyalkyl, an alkoxyalkyl, or a haloalkyl.

49. The composition of matter according to claim 27, wherein J is $CR_7$ and $R_6$ and $R_7$, together with the carbon atoms to which they are attached, join to form a 6-membered carbocyclic aromatic ring that may be optionally substituted with up to three substituents.

50. The composition of matter according to claim 27, wherein the compound is selected from one of the following compounds or is a salt thereof, a tautomer thereof, or a salt of the tautomer:
N-((2-(4-chlorophenyl)-7-hydroxy-4-methyl-5-oxo-4,5-dihydro[1,3]thiazolo[4,5-b]pyridin-6-yl)carbonyl)glycine;
N-((7-hydroxy-2,4-dimethyl-5-oxo-4,5-dihydro[1,3]thiazolo[4,5-b]pyridin-6-yl)carbonyl)glycine;
2-(7-hydroxy-4-methyl-5-oxo-4,5-dihydrothieno[3,2-b]pyridine-6-carboxamido)acetic acid;
2-(7-hydroxy-3,4-dimethyl-5-oxo-4,5-dihydrothieno[3,2-b]pyridine-6-carboxamido)acetic acid;
2-(2-(4-chlorophenyl)-7-hydroxy-4-methyl-5-oxo-4,5-dihydrothieno[3,2-b]pyridine-6-carboxamido)acetic acid;
2-(2-bromo-7-hydroxy-4-methyl-5-oxo-4,5-dihydrothieno[3,2-b]pyridine-6-carboxamido)acetic acid;
(S)-2-(7-hydroxy-3,4-dimethyl-5-oxo-4,5-dihydrothieno[3,2-b]pyridine-6-carboxamido)propanoic acid;
2-(7-hydroxy-4-methyl-5-oxo-3-phenyl-2-(trifluoromethyl)-4,5-dihydrothieno[3,2-b]pyridine-6-carboxamido)acetic acid;
N-((4-hydroxy-1-methyl-2-oxo-1,2-dihydro[1]benzothieno[3,2-b]pyridin-3-yl)carbonyl)glycine;
N-((4-hydroxy-1-methyl-2-oxo-1,2-dihydro[1]benzothieno[3,2-b]pyridin-3-yl)carbonyl)-L-alanine;
2-(2-(4-fluorophenyl)-7-hydroxy-4-methyl-5-oxo-4,5-dihydrothieno[3,2-b]pyridine-6-carboxamido)acetic acid;
2-(7-hydroxy-4-methyl-5-oxo-2-(pyrimidin-5-yl)-4,5-dihydrothieno[3,2-b]pyridine-6-carboxamido)acetic acid;
2-(7-hydroxy-4-methyl-2-(2-methylpyridin-3-yl)-5-oxo-4,5-dihydrothieno[3,2-b]pyridine-6-carboxamido)acetic acid;
2-(7-hydroxy-4-methyl-2-(3-methylthiophen-2-yl)-5-oxo-4,5-dihydrothieno[3,2-b]pyridine-6-carboxamido) acetic acid;
2-(7-hydroxy-4-methyl-5-oxo-2-phenyl-4,5-dihydrothieno[3,2-b]pyridine-6-carboxamido)acetic acid;
2-(2-bromo-7-hydroxy-3,4-dimethyl-5-oxo-4,5-dihydrothieno[3,2-b]pyridine-6-carboxamido)acetic acid; or
4-(2-bromo-7-hydroxy-4-methyl-5-oxo-4,5-dihydrothieno[3,2-b]pyridin-6-yl)-4-oxobutanoic acid.

51. The composition of matter according to claim 27, wherein the compound is selected from one of the following compounds or is a salt thereof, a tautomer thereof, or a salt of the tautomer:
2-(2-(3,6-dihydro-2H-pyran-4-yl)-7-hydroxy-4-methyl-5-oxo-4,5-dihydrothieno[3,2-b]pyridine-6-carboxamido)acetic acid;
4-(6-((carboxymethyl)carbamoyl)-7-hydroxy-4-methyl-5-oxo-4,5-dihydrothieno[3,2-b]pyridin-2-yl)benzoic acid;
2-(2-(2-chlorophenyl)-7-hydroxy-4-methyl-5-oxo-4,5-dihydrothieno[3,2-b]pyridine-6-carboxamido)acetic acid;
2-(2-cyclopropyl-7-hydroxy-4-methyl-5-oxo-4,5-dihydrothieno[3,2-b]pyridine-6-carboxamido)acetic acid;
2-(2-(2-chlorophenyl)-7-hydroxy-3,4-dimethyl-5-oxo-4,5-dihydrothieno[3,2-b]pyridine-6-carboxamido)acetic acid;
6-((carboxymethyl)carbamoyl)-7-hydroxy-3,4-dimethyl-5-oxo-4,5-dihydrothieno[3,2-b]pyridine-2-carboxylic acid;
2-(2-(2-chlorophenyl)-7-hydroxy-4-methyl-5-oxo-4,5-dihydrothiazolo[4,5-b]pyridine-6-carboxamido)acetic acid;
2-(2-cyclopropyl-7-hydroxy-4-methyl-5-oxo-4,5-dihydrothiazolo[4,5-b]pyridine-6-carboxamido)acetic acid;
2-(7-hydroxy-4-methyl-5-oxo-2-(thiophen-2-yl)-4,5-dihydrothiazolo[4,5-b]pyridine-6-carboxamido)acetic acid;
2-(7-hydroxy-4-methyl-5-oxo-2-(pyridin-3-yl)-4,5-dihydrothiazolo[4,5-b]pyridine-6-carboxamido)acetic acid;
2-(4-benzyl-2-bromo-7-hydroxy-5-oxo-4,5-dihydrothieno[3,2-b]pyridine-6-carboxamido)acetic acid;
2-(4-benzyl-7-hydroxy-2-methyl-5-oxo-4,5-dihydrothiazolo[4,5-b]pyridine-6-carboxamido)acetic acid; or
4-(7-hydroxy-4-methyl-5-oxo-2-phenyl-4,5-dihydrothieno[3,2-b]pyridin-6-yl)-4-oxobutanoic acid.

52. A pharmaceutical formulation, comprising a therapeutically effective amount of the composition of matter according to claim 27 and at least one pharmaceutically acceptable excipient.

53. The pharmaceutical formulation of claim 52, wherein the composition of matter is present in an amount effective for the treatment of at least one disease selected from ischemia, anemia, wound healing, auto-transplantation, allo-transplantation, xeno-transplantation, systemic high blood pressure, thalassemia, diabetes, cancer, or an inflammatory disorder.

54. A composition of matter, comprising at least one compound of Formula I:

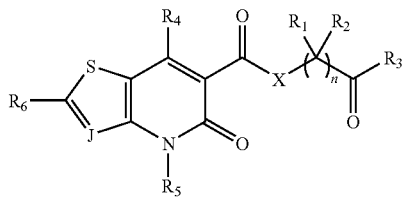

a pharmaceutically acceptable salt thereof, a tautomer thereof, or a pharmaceutically acceptable salt of the tautomer; or a solvate thereof, a chelate thereof, a non-covalent complex thereof, a prodrug thereof, or a mixture of any of the foregoing, wherein:

J is selected from $CR_7$ or N;
n is 1;
$R_1$ and $R_2$ are both H;
X is —$NR_a$—, wherein $R_a$ is selected from H or lower alkyl;
$R_3$ is selected from OH, SH, $NH_2$, lower alkyl, substituted lower alkyl, lower alkoxy, substituted lower alkoxy, or sulfanyl;
$R_4$ is selected from H, OH, lower alkoxy, SH, $NH_2$, $NHSO_2R_8$, or sulfonyl;
$R_5$ is selected from H, lower alkyl, or substituted lower alkyl;
$R_6$ and $R_7$ are independently selected from H, F, Cl, Br, I, alkyl, substituted alkyl, haloalkyl, perhaloalkyl, alkenyl, substituted alkenyl, alkynyl, substituted alkynyl, $NR_dR_e$, $C(O)R_8$, $C(O)OR_9$, $OR_9$, $SR_9$, $SO_2R_9$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, or —Y—$R_{10}$; or, $R_6$ and $R_7$ may join to form an optionally substituted 5 or 6 membered ring when J is $CR_7$, wherein:
Y is selected from —$N(R_{11})$—Z— or —Z—$N(R_{11})$—;
Z is selected from C(O), $SO_2$, alkylene, substituted alkylene, alkenylene, substituted alkenylene, alkynylene, or substituted alkynylene;
$R_8$ is selected from H, alkyl, substituted alkyl, alkenyl, substituted alkenyl, alkynyl, substituted alkynyl heterocyclyl, substituted heterocyclyl, aryl, substituted aryl, heteroaryl, or substituted heteroaryl;
$R_9$ is selected from H, alkyl, substituted alkyl, alkenyl, substituted alkenyl, alkynyl, or substituted alkynyl;
$R_{10}$ is selected from H, heterocyclyl, substituted heterocyclyl, aryl, substituted aryl, heteroaryl, or substituted heteroaryl;
$R_{11}$ is selected from H, lower alkyl, or substituted lower alkyl; and
$R_d$ and $R_e$ are independently selected from H, lower alkyl, substituted lower alkyl, lower haloalkyl, or substituted lower haloalkyl, or $R_d$ and $R_e$ can join together to form a 3 to 6 membered ring or a substituted 3 to 6 membered ring.

55. The composition of matter according to claim 54, wherein $R_3$ is OH.

56. The composition of matter according to claim 54, wherein $R_4$ is OH.

57. The composition of matter according to claim 54, wherein at least one of $R_6$ or $R_7$ is a substituted or unsubstituted aryl, a substituted or unsubstituted heteroaryl, a substituted or unsubstituted cycloalkyl, or a substituted or unsubstituted heterocyclyl group.

58. The composition of matter according to claim 57, wherein at least one of $R_6$ or $R_7$ is a heterocyclyl group.

59. The composition of matter according to claim 57, wherein at least one of $R_6$ or $R_7$ is a heteroaryl group.

60. The composition of matter according to claim 57, wherein at least one of $R_6$ or $R_7$ is a phenyl or substituted phenyl group.

61. The composition of matter according to claim 54, wherein at least one of $R_6$ or $R_7$ is chosen from a halo or a moiety substituted with at least one halo.

62. The composition of matter according to claim 54, wherein J is $CR_7$, $R_3$ is OH; and $R_4$ is OH.

63. The composition of matter according to claim 54 wherein J is N; $R_3$ is OH; and $R_4$ is OH.

64. The composition of matter according to claim 54, wherein $R_5$ is H.

65. The composition of matter according to claim 54, wherein $R_5$ is lower alkyl.

66. The composition of matter according to claim 54, wherein $R_5$ is methyl.

67. The composition of matter according to claim 54, wherein $R_5$ is a substituted lower alkyl selected from an arylalkyl, a heteroarylalkyl, a heterocyclylalkyl, a cycloalkylalkyl, a hydroxyalkyl, an alkoxyalkyl, or a haloalkyl.

68. The composition of matter according to claim 54, wherein J is $CR_7$ and $R_6$ and $R_7$, together with the carbon atoms to which they are attached, join to form a 6-membered carbocyclic aromatic ring that may be optionally substituted with up to three substituents.

69. The composition of matter according to claim 54, wherein the compound is selected from one of the following compounds or is a salt thereof, a tautomer thereof, or a salt of the tautomer:
N-((2-(4-chlorophenyl)-7-hydroxy-4-methyl-5-oxo-4,5-dihydro[1,3]thiazolo[4,5-b]pyridin-6-yl)carbonyl)glycine;
N-((7-hydroxy-2,4-dimethyl-5-oxo-4,5-dihydro[1,3]thiazolo[4,5-b]pyridin-6-yl)carbonyl)glycine;
2-(7-hydroxy-4-methyl-5-oxo-4,5-dihydrothieno[3,2-b]pyridine-6-carboxamido)acetic acid;
2-(7-hydroxy-3,4-dimethyl-5-oxo-4,5-dihydrothieno[3,2-b]pyridine-6-carboxamido)acetic acid;
2-(2-(4-chlorophenyl)-7-hydroxy-4-methyl-5-oxo-4,5-dihydrothieno[3,2-b]pyridine-6-carboxamido)acetic acid;
2-(2-bromo-7-hydroxy-4-methyl-5-oxo-4,5-dihydrothieno[3,2-b]pyridine-6-carboxamido)acetic acid;
2-(7-hydroxy-4-methyl-5-oxo-3-phenyl-2-(trifluoromethyl)-4,5-dihydrothieno[3,2-b]pyridine-6-carboxamido)acetic acid;
N-((4-hydroxy-1-methyl-2-oxo-1,2-dihydro[1]benzothieno[3,2-b]pyridin-3-yl)carbonyl)glycine;
2-(2-(4-fluorophenyl)-7-hydroxy-4-methyl-5-oxo-4,5-dihydrothieno[3,2-b]pyridine-6-carboxamido)acetic acid;
2-(7-hydroxy-4-methyl-5-oxo-2-(pyrimidin-5-yl)-4,5-dihydrothieno[3,2-b]pyridine-6-carboxamido)acetic acid;
2-(7-hydroxy-4-methyl-2-(2-methylpyridin-3-yl)-5-oxo-4,5-dihydrothieno[3,2-b]pyridine-6-carboxamido)acetic acid;

2-(7-hydroxy-4-methyl-2-(3-methylthiophen-2-yl)-5-oxo-4,5-dihydrothieno[3,2-b]pyridine-6-carboxamido)acetic acid;

2-(7-hydroxy-4-methyl-5-oxo-2-phenyl-4,5-dihydrothieno[3,2-b]pyridine-6-carboxamido)acetic acid; or 2-(2-bromo-7-hydroxy-3,4-dimethyl-5-oxo-4,5-dihydrothieno[3,2-b]pyridine-6-carboxamido)acetic acid.

70. The composition of matter according to claim 54, wherein the compound is selected from one of the following compounds or is a salt thereof, a tautomer thereof, or a salt of the tautomer:

2-(2-(3,6-dihydro-2H-pyran-4-yl)-7-hydroxy-4-methyl-5-oxo-4,5-dihydrothieno[3,2-b]pyridine-6-carboxamido)acetic acid;

4-(6-((carboxymethyl)carbamoyl)-7-hydroxy-4-methyl-5-oxo-4,5-dihydrothieno[3,2-b]pyridin-2-yl)benzoic acid;

2-(2-(2-chlorophenyl)-7-hydroxy-4-methyl-5-oxo-4,5-dihydrothieno[3,2-b]pyridine-6-carboxamido)acetic acid;

2-(2-cyclopropyl-7-hydroxy-4-methyl-5-oxo-4,5-dihydrothieno[3,2-b]pyridine-6-carboxamido)acetic acid;

2-(2-(2-chlorophenyl)-7-hydroxy-3,4-dimethyl-5-oxo-4,5-dihydrothieno[3,2-b]pyridine-6-carboxamido)acetic acid;

6-((carboxymethyl)carbamoyl)-7-hydroxy-3,4-dimethyl-5-oxo-4,5-dihydrothieno[3,2-b]pyridine-2-carboxylic acid;

2-(2-(2-chlorophenyl)-7-hydroxy-4-methyl-5-oxo-4,5-dihydrothiazolo[4,5-b]pyridine-6-carboxamido)acetic acid;

2-(2-cyclopropyl-7-hydroxy-4-methyl-5-oxo-4,5-dihydrothiazolo[4,5-b]pyridine-6-carboxamido)acetic acid;

2-(7-hydroxy-4-methyl-5-oxo-2-(thiophen-2-yl)-4,5-dihydrothiazolo[4,5-b]pyridine-6-carboxamido)acetic acid;

2-(7-hydroxy-4-methyl-5-oxo-2-(pyridin-3-yl)-4,5-dihydrothiazolo[4,5-b]pyridine-6-carboxamido)acetic acid;

2-(4-benzyl-2-bromo-7-hydroxy-5-oxo-4,5-dihydrothieno[3,2-b]pyridine-6-carboxamido)acetic acid; or 2-(4-benzyl-7-hydroxy-2-methyl-5-oxo-4,5-dihydrothiazolo[4,5-b]pyridine-6-carboxamido)acetic acid.

71. A pharmaceutical formulation, comprising a therapeutically effective amount of the composition of matter according to claim 54 and at least one pharmaceutically acceptable excipient.

72. The pharmaceutical formulation of claim 71, wherein the composition of matter is present in an amount effective for the treatment of at least one disease selected from ischemia, anemia, wound healing, auto-transplantation, allo-transplantation, xeno-transplantation, systemic high blood pressure, thalassemia, diabetes, cancer, or an inflammatory disorder.

73. The composition of matter according to claim 70, wherein J is N.

74. The composition of matter according to claim 54, wherein J is $CR_7$.

* * * * *

```
                       SEQUENCE LISTING

<160> NUMBER OF SEQ ID NOS: 11

<210> SEQ ID NO 1
<211> LENGTH: 166
<212> TYPE: PRT
<213> ORGANISM: Homo sapiens

<400> SEQUENCE: 1

Met His His His His His His Glu Ala Gly Arg Pro Arg Pro Val Leu
1               5                   10                  15

Arg Ser Val Asn Ser Arg Glu Pro Ser Gln Val Ile Phe Cys Asn Arg
                20                  25                  30

Ser Pro Arg Val Val Leu Pro Val Trp Leu Asn Phe Asp Gly Glu Pro
            35                  40                  45

Gln Pro Tyr Pro Thr Leu Pro Pro Gly Thr Gly Arg Arg Ile His Ser
        50                  55                  60

Tyr Arg Gly His Leu Trp Leu Phe Arg Asp Ala Gly Thr His Asp Gly
65                  70                  75                  80

Leu Leu Val Asn Gln Thr Glu Leu Phe Val Pro Ser Leu Asn Val Asp
                85                  90                  95

Gly Gln Pro Ile Phe Ala Asn Ile Thr Leu Pro Val Tyr Thr Leu Lys
            100                 105                 110

Glu Arg Cys Leu Gln Val Val Arg Ser Leu Val Lys Pro Glu Asn Tyr
        115                 120                 125

Arg Arg Leu Asp Ile Val Arg Ser Leu Tyr Glu Asp Leu Glu Asp His
    130                 135                 140

Pro Asn Val Gln Lys Asp Leu Glu Arg Leu Thr Gln Glu Arg Ile Ala
145                 150                 155                 160

His Gln Arg Met Gly Asp
                165

<210> SEQ ID NO 2
<211> LENGTH: 118
<212> TYPE: PRT
<213> ORGANISM: Homo sapiens

<400> SEQUENCE: 2

Met Asp Val Phe Leu Met Ile Arg Arg His Lys Thr Thr Ile Phe Thr
1               5                   10                  15

Asp Ala Lys Glu Ser Ser Thr Val Phe Glu Leu Lys Arg Ile Val Glu
                20                  25                  30

Gly Ile Leu Lys Arg Pro Pro Asp Glu Gln Arg Leu Tyr Lys Asp Asp
            35                  40                  45

Gln Leu Leu Asp Asp Gly Lys Thr Leu Gly Glu Cys Gly Phe Thr Ser
        50                  55                  60

Gln Thr Ala Arg Pro Gln Ala Pro Ala Thr Val Gly Leu Ala Phe Arg
65                  70                  75                  80

Ala Asp Asp Thr Phe Glu Ala Leu Cys Ile Glu Pro Phe Ser Ser Pro
                85                  90                  95
```

```
Pro Glu Leu Pro Asp Val Met Lys Pro Gln Asp Ser Gly Ser Ser Ala
            100                 105                 110

Asn Glu Gln Ala Val Gln
        115

<210> SEQ ID NO 3
<211> LENGTH: 96
<212> TYPE: PRT
<213> ORGANISM: Homo sapiens

<400> SEQUENCE: 3

Met Tyr Val Lys Leu Ile Ser Ser Asp Gly His Glu Phe Ile Val Lys
1               5                   10                  15

Arg Glu His Ala Leu Thr Ser Gly Thr Ile Lys Ala Met Leu Ser Gly
            20                  25                  30

Pro Gly Gln Phe Ala Glu Asn Glu Thr Asn Glu Val Asn Phe Arg Glu
        35                  40                  45

Ile Pro Ser His Val Leu Ser Lys Val Cys Met Tyr Phe Thr Tyr Lys
    50                  55                  60

Val Arg Tyr Thr Asn Ser Ser Thr Glu Ile Pro Glu Phe Pro Ile Ala
65                  70                  75                  80

Pro Glu Ile Ala Leu Glu Leu Leu Met Ala Ala Asn Phe Leu Asp Cys
                85                  90                  95

<210> SEQ ID NO 4
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylation
<220> FEATURE:
<221> NAME/KEY: MISC_FEATURE
<222> LOCATION: (20)..(20)
<223> OTHER INFORMATION: Carboxylation

<400> SEQUENCE: 4

Asp Leu Asp Leu Glu Ala Leu Ala Pro Tyr Ile Pro Ala Asp Asp Asp
1               5                   10                  15

Phe Gln Leu Arg
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylation
<220> FEATURE:
<221> NAME/KEY: MISC_FEATURE
<222> LOCATION: (9)..(9)
<223> OTHER INFORMATION: Xaa at position 9 is hydroxyproline
<220> FEATURE:
<221> NAME/KEY: MISC_FEATURE
<222> LOCATION: (20)..(20)
<223> OTHER INFORMATION: Carboxyamidated
```

-continued

```
<400> SEQUENCE: 5

Asp Leu Asp Leu Glu Ala Leu Ala Xaa Tyr Ile Pro Ala Asp Asp
1               5                   10                  15

Phe Gln Leu Arg
            20

<210> SEQ ID NO 6
<211> LENGTH: 17
<212> TYPE: PRT
<213> ORGANISM: Artificial Sequence
<220> FEATURE:
<223> OTHER INFORMATION: Synthetic peptide

<400> SEQUENCE: 6

Asp Leu Glu Met Leu Ala Pro Tyr Ile Pro Met Asp Asp Phe Gln
1               5                   10                  15

Leu

<210> SEQ ID NO 7
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylation

<400> SEQUENCE: 7

Asp Leu Glu Met Leu Ala Pro Tyr Ile Pro Met Asp Asp Phe Gln
1               5                   10                  15

Leu

<210> SEQ ID NO 8
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Metal affinity tag which includes histidines
      at positions 3 through 8

<400> SEQUENCE: 8

Met Ala His His His His His His Asp Glu Val Asp
1               5                   10

<210> SEQ ID NO 9
<211> LENGTH: 545
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Metal affinity tag which includes histidines
      at positions 3 through 8
<220> FEATURE:
<221> NAME/KEY: MISC_FEATURE
<222> LOCATION: (13)..(28)
<223> OTHER INFORMATION: Secretion signal sequence

<400> SEQUENCE: 9

Met Ala His His His His His His Asp Glu Val Asp Ile Trp Tyr Ile
1               5                   10                  15

Leu Ile Gly Ile Leu Leu Pro Gln Ser Leu Ala His Pro Gly Phe
            20                  25                  30
```

```
Phe Thr Ser Ile Gly Gln Met Thr Asp Leu Ile His Thr Glu Lys Asp
             35                  40                  45

Leu Val Thr Ser Leu Lys Asp Tyr Ile Lys Ala Glu Glu Asp Lys Leu
 50                  55                  60

Glu Gln Ile Lys Lys Trp Ala Glu Lys Leu Asp Arg Leu Thr Ser Thr
 65                  70                  75                  80

Ala Thr Lys Asp Pro Glu Gly Phe Val Gly His Pro Val Asn Ala Phe
                 85                  90                  95

Lys Leu Met Lys Arg Leu Asn Thr Glu Trp Ser Glu Leu Glu Asn Leu
                100                 105                 110

Val Leu Lys Asp Met Ser Asp Gly Phe Ile Ser Asn Leu Thr Ile Gln
            115                 120                 125

Arg Gln Tyr Phe Pro Asn Asp Glu Asp Gln Val Gly Ala Ala Lys Ala
        130                 135                 140

Leu Leu Arg Leu Gln Asp Thr Tyr Asn Leu Asp Thr Asp Thr Ile Ser
145                 150                 155                 160

Lys Gly Asn Leu Pro Gly Val Lys His Lys Ser Phe Leu Thr Ala Glu
                165                 170                 175

Asp Cys Phe Glu Leu Gly Lys Val Ala Tyr Thr Glu Ala Asp Tyr Tyr
            180                 185                 190

His Thr Glu Leu Trp Met Glu Gln Ala Leu Arg Gln Leu Asp Glu Gly
        195                 200                 205

Glu Ile Ser Thr Ile Asp Lys Val Ser Val Leu Asp Tyr Leu Ser Tyr
210                 215                 220

Ala Val Tyr Gln Gln Gly Asp Leu Asp Lys Ala Leu Leu Leu Thr Lys
225                 230                 235                 240

Lys Leu Leu Glu Leu Asp Pro Glu His Gln Arg Ala Asn Gly Asn Leu
                245                 250                 255

Lys Tyr Phe Glu Tyr Ile Met Ala Lys Glu Lys Asp Val Asn Lys Ser
                260                 265                 270

Ala Ser Asp Asp Gln Ser Asp Gln Lys Thr Thr Pro Lys Lys Lys Gly
            275                 280                 285

Val Ala Val Asp Tyr Leu Pro Glu Arg Gln Lys Tyr Glu Met Leu Cys
        290                 295                 300

Arg Gly Glu Gly Ile Lys Met Thr Pro Arg Arg Gln Lys Lys Leu Phe
305                 310                 315                 320

Cys Arg Tyr His Asp Gly Asn Arg Asn Pro Lys Phe Ile Leu Ala Pro
                325                 330                 335

Ala Lys Gln Glu Asp Glu Trp Asp Lys Pro Arg Ile Ile Arg Phe His
            340                 345                 350

Asp Ile Ile Ser Asp Ala Glu Ile Glu Ile Val Lys Asp Leu Ala Lys
        355                 360                 365

Pro Arg Leu Ser Arg Ala Thr Val His Asp Pro Glu Thr Gly Lys Leu
370                 375                 380

Thr Thr Ala Gln Tyr Arg Val Ser Lys Ser Ala Trp Leu Ser Gly Tyr
385                 390                 395                 400

Glu Asn Pro Val Val Ser Arg Ile Asn Met Arg Ile Gln Asp Leu Thr
                405                 410                 415

Gly Leu Asp Val Ser Thr Ala Glu Glu Leu Gln Val Ala Asn Tyr Gly
            420                 425                 430

Val Gly Gly Gln Tyr Glu Pro His Phe Asp Phe Ala Arg Lys Asp Glu
        435                 440                 445

Pro Asp Ala Phe Lys Glu Leu Gly Thr Gly Asn Arg Ile Ala Thr Trp
450                 455                 460
```

```
Leu Phe Tyr Met Ser Asp Val Ser Ala Gly Ala Thr Val Phe Pro
465                 470                 475                 480

Glu Val Gly Ala Ser Val Trp Pro Lys Lys Gly Thr Ala Val Phe Trp
            485                 490                 495

Tyr Asn Leu Phe Ala Ser Gly Glu Gly Asp Tyr Ser Thr Arg His Ala
                500                 505                 510

Ala Cys Pro Val Leu Val Gly Asn Lys Trp Val Ser Asn Lys Trp Leu
            515                 520                 525

His Glu Arg Gly Gln Glu Phe Arg Arg Pro Cys Thr Leu Ser Glu Leu
530                 535                 540

Glu
545

<210> SEQ ID NO 10
<211> LENGTH: 544
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Metal affinity tag which includes histidines
      at positions 3 through 8
<220> FEATURE:
<221> NAME/KEY: MISC_FEATURE
<222> LOCATION: (13)..(32)
<223> OTHER INFORMATION: Secretion signal sequence

<400> SEQUENCE: 10

Met Ala His His His His His His Asp Glu Val Asp Lys Leu Trp Val
1               5                   10                  15

Ser Ala Leu Leu Met Ala Trp Phe Gly Val Leu Ser Cys Val Gln Ala
                20                  25                  30

Glu Phe Phe Thr Ser Ile Gly His Met Thr Asp Leu Ile Tyr Ala Glu
                35                  40                  45

Lys Glu Leu Val Gln Ser Leu Lys Glu Tyr Ile Leu Val Glu Glu Ala
            50                  55                  60

Lys Leu Ser Lys Ile Lys Ser Trp Ala Asn Lys Met Glu Ala Leu Thr
65                  70                  75                  80

Ser Lys Ser Ala Ala Asp Ala Glu Gly Tyr Leu Ala His Pro Val Asn
                85                  90                  95

Ala Tyr Lys Leu Val Lys Arg Leu Asn Thr Asp Trp Pro Ala Leu Glu
            100                 105                 110

Asp Leu Val Leu Gln Asp Ser Ala Ala Gly Phe Ile Ala Asn Leu Ser
            115                 120                 125

Val Gln Arg Gln Phe Phe Pro Thr Asp Glu Asp Glu Ile Gly Ala Ala
130                 135                 140

Lys Ala Leu Met Arg Leu Gln Asp Thr Tyr Arg Leu Asp Pro Gly Thr
145                 150                 155                 160

Ile Ser Arg Gly Glu Leu Pro Gly Thr Lys Tyr Gln Ala Met Leu Ser
                165                 170                 175

Val Asp Asp Cys Phe Gly Met Gly Arg Ser Ala Tyr Asn Glu Gly Asp
            180                 185                 190

Tyr Tyr His Thr Val Leu Trp Met Glu Gln Val Leu Lys Gln Leu Asp
            195                 200                 205

Ala Gly Glu Glu Ala Thr Thr Thr Lys Ser Gln Val Leu Asp Tyr Leu
210                 215                 220

Ser Tyr Ala Val Phe Gln Leu Gly Asp Leu His Arg Ala Leu Glu Leu
225                 230                 235                 240
```

-continued

```
        Thr Arg Arg Leu Leu Ser Leu Asp Pro Ser His Glu Arg Ala Gly Gly
                        245                 250                 255

Asn Leu Arg Tyr Phe Glu Gln Leu Glu Glu Arg Glu Lys Thr
            260                 265                 270

Leu Thr Asn Gln Thr Glu Ala Glu Leu Ala Thr Pro Glu Gly Ile Tyr
                    275                 280                 285

Glu Arg Pro Val Asp Tyr Leu Pro Glu Arg Asp Val Tyr Glu Ser Leu
                290                 295                 300

Cys Arg Gly Glu Gly Val Lys Leu Thr Pro Arg Arg Gln Lys Arg Leu
        305                 310                 315                 320

Phe Cys Arg Tyr His His Gly Asn Arg Ala Pro Gln Leu Leu Ile Ala
                        325                 330                 335

Pro Phe Lys Glu Glu Asp Glu Trp Asp Ser Pro His Ile Val Arg Tyr
                    340                 345                 350

Tyr Asp Val Met Ser Asp Glu Glu Ile Glu Arg Ile Lys Glu Ile Ala
                355                 360                 365

Lys Pro Lys Leu Ala Arg Ala Thr Val Arg Asp Pro Lys Thr Gly Val
                370                 375                 380

Leu Thr Val Ala Ser Tyr Arg Val Ser Lys Ser Ser Trp Leu Glu Glu
        385                 390                 395                 400

Asp Asp Pro Val Val Ala Arg Val Asn Arg Arg Met Gln His Ile
                        405                 410                 415

Thr Gly Leu Thr Val Lys Thr Ala Glu Leu Leu Gln Val Ala Asn Tyr
                    420                 425                 430

Gly Val Gly Gly Gln Tyr Glu Pro His Phe Asp Phe Ser Arg Arg Pro
                435                 440                 445

Phe Asp Ser Gly Leu Lys Thr Glu Gly Asn Arg Leu Ala Thr Phe Leu
            450                 455                 460

Asn Tyr Met Ser Asp Val Glu Ala Gly Gly Ala Thr Val Phe Pro Asp
        465                 470                 475                 480

Leu Gly Ala Ala Ile Trp Pro Lys Lys Gly Thr Ala Val Phe Trp Tyr
                        485                 490                 495

Asn Leu Leu Arg Ser Gly Glu Gly Asp Tyr Arg Thr Arg His Ala Ala
                    500                 505                 510

Cys Pro Val Leu Val Gly Cys Lys Trp Val Ser Asn Lys Trp Phe His
                515                 520                 525

Glu Arg Gly Gln Glu Phe Leu Arg Pro Cys Gly Ser Thr Glu Val Asp
            530                 535                 540

<210> SEQ ID NO 11
<211> LENGTH: 514
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: Secretion signal sequence
<220> FEATURE:
<221> NAME/KEY: MISC_FEATURE
<222> LOCATION: (18)..(23)
<223> OTHER INFORMATION: Six-histidine metal affinity tag

<400> SEQUENCE: 11

Met Leu Arg Arg Ala Leu Leu Cys Leu Ala Val Ala Ala Leu Val Arg
        1               5                   10                  15

Ala His His His His His His Asp Ala Pro Glu Glu Glu Asp His Val
                        20                  25                  30
```

```
Leu Val Leu Arg Lys Ser Asn Phe Ala Glu Ala Leu Ala Ala His Lys
         35                  40                  45

Tyr Leu Leu Val Glu Phe Tyr Ala Pro Trp Cys Gly His Cys Lys Ala
 50                  55                  60

Leu Ala Pro Glu Tyr Ala Lys Ala Ala Gly Lys Leu Lys Ala Glu Gly
 65                  70                  75                  80

Ser Glu Ile Arg Leu Ala Lys Val Asp Ala Thr Glu Glu Ser Asp Leu
                 85                  90                  95

Ala Gln Gln Tyr Gly Val Arg Gly Tyr Pro Thr Ile Lys Phe Phe Arg
            100                 105                 110

Asn Gly Asp Thr Ala Ser Pro Lys Glu Tyr Thr Ala Gly Arg Glu Ala
            115                 120                 125

Asp Asp Ile Val Asn Trp Leu Lys Lys Arg Thr Gly Pro Ala Ala Thr
130                 135                 140

Thr Leu Pro Asp Gly Ala Ala Ala Glu Ser Leu Val Glu Ser Ser Glu
145                 150                 155                 160

Val Ala Val Ile Gly Phe Phe Lys Asp Val Glu Ser Asp Ser Ala Lys
                165                 170                 175

Gln Phe Leu Gln Ala Ala Glu Ala Ile Asp Asp Ile Pro Phe Gly Ile
            180                 185                 190

Thr Ser Asn Ser Asp Val Phe Ser Lys Tyr Gln Leu Asp Lys Asp Gly
            195                 200                 205

Val Val Leu Phe Lys Lys Phe Asp Glu Gly Arg Asn Asn Phe Glu Gly
210                 215                 220

Glu Val Thr Lys Glu Asn Leu Leu Asp Phe Ile Lys His Asn Gln Leu
225                 230                 235                 240

Pro Leu Val Ile Glu Phe Thr Glu Gln Thr Ala Pro Lys Ile Phe Gly
                245                 250                 255

Gly Glu Ile Lys Thr His Ile Leu Leu Phe Leu Pro Lys Ser Val Ser
            260                 265                 270

Asp Tyr Asp Gly Lys Leu Ser Asn Phe Lys Thr Ala Ala Glu Ser Phe
            275                 280                 285

Lys Gly Lys Ile Leu Phe Ile Phe Ile Asp Ser Asp His Thr Asp Asn
290                 295                 300

Gln Arg Ile Leu Glu Phe Phe Gly Leu Lys Lys Glu Glu Cys Pro Ala
305                 310                 315                 320

Val Arg Leu Ile Thr Leu Glu Glu Met Thr Lys Tyr Lys Pro Glu
                325                 330                 335

Ser Glu Glu Leu Thr Ala Glu Arg Ile Thr Glu Phe Cys His Arg Phe
            340                 345                 350

Leu Glu Gly Lys Ile Lys Pro His Leu Met Ser Gln Glu Leu Pro Glu
            355                 360                 365

Asp Trp Asp Lys Gln Pro Val Lys Val Leu Val Gly Lys Asn Phe Glu
370                 375                 380

Asp Val Ala Phe Asp Glu Lys Lys Asn Val Phe Val Glu Phe Tyr Ala
385                 390                 395                 400

Pro Trp Cys Gly His Cys Lys Gln Leu Ala Pro Ile Trp Asp Lys Leu
                405                 410                 415

Gly Glu Thr Tyr Lys Asp His Glu Asn Ile Val Ile Ala Lys Met Asp
            420                 425                 430

Ser Thr Ala Asn Glu Val Glu Ala Val Lys Val His Ser Phe Pro Thr
            435                 440                 445

Leu Lys Phe Phe Pro Ala Ser Ala Asp Arg Thr Val Ile Asp Tyr Asn
450                 455                 460
```

```
Gly Glu Arg Thr Leu Asp Gly Phe Lys Lys Phe Leu Glu Ser Gly Gly
465                 470                 475                 480

Gln Asp Gly Ala Gly Asp Asp Asp Leu Glu Asp Leu Glu Glu Ala
                485             490             495

Glu Glu Pro Asp Met Glu Glu Asp Asp Gln Lys Ala Val Lys Asp
            500             505             510

Glu Leu
```